US012134388B2

(12) United States Patent
Barcia et al.

(10) Patent No.: US 12,134,388 B2
(45) Date of Patent: Nov. 5, 2024

(54) APPARATUS FOR COMMUNICATIVELY CONNECTING A CAR SEAT TO RETRIEVE HEALTH DATA

(71) Applicant: Volvo Car Corporation, Gothenburg (SE)

(72) Inventors: Peter Barcia, Summerville, SC (US); Anthony Raimondi, North Charleston, SC (US); Ronald J Roselli, Summerville, SC (US); Kyle Caroncino, Mount Pleasant, SC (US); Derek Boesch, Summerville, SC (US); Giovanni Spiritoso, Summerville, SC (US)

(73) Assignee: VOLVO CAR CORPORATION, Gothenburg (SE)

( * ) Notice: Subject to any disclaimer, the term of this patent is extended or adjusted under 35 U.S.C. 154(b) by 5 days.

(21) Appl. No.: 17/982,117

(22) Filed: Nov. 7, 2022

(65) Prior Publication Data
US 2024/0149883 A1    May 9, 2024

(51) Int. Cl.
*B60W 40/08*    (2012.01)
*A61B 5/0205*    (2006.01)
(Continued)

(52) U.S. Cl.
CPC ......... *B60W 40/08* (2013.01); *A61B 5/02055* (2013.01); *A61B 5/02438* (2013.01); *B60N 2/002* (2013.01); *B60W 50/14* (2013.01); *G06V 20/593* (2022.01); *G16H 30/20* (2018.01); *H04N 5/33* (2013.01); *B60W 2050/146* (2013.01);
(Continued)

(58) Field of Classification Search
CPC ................. B60W 40/08; B60W 50/14; B60W 2050/146; B60W 2420/403; B60W 2540/221; B60W 2540/223; B60W 2556/45; A61B 5/02055; A61B 5/02438;
(Continued)

(56) References Cited

U.S. PATENT DOCUMENTS 9,443,411 B2    9/2016  Schoenberg
9,848,814 B2   12/2017  Benson et al.
(Continued)

FOREIGN PATENT DOCUMENTS

WO    2017030522 A1    2/2017
WO    2022015719 A1    1/2022

*Primary Examiner* — Ryan W Sherwin
(74) *Attorney, Agent, or Firm* — Raj S. Dave; Dave Law Group LLC

(57) ABSTRACT

An embodiment relates to a system comprising a sensor, an image sensor, a display, a connector, a communication module, and a processor. The processor is configured to detect a vehicle seat in the vehicle, establish a secured connection with the vehicle seat through the connector; receive a first data from the sensor and a second data from the image sensor through the connector, the first data and the second data being indicative of information gathered regarding at least one parameter related to at least one of a condition of the vehicle seat, a health and wellness of an occupant of the vehicle, and the connector being configured to facilitate gathering of the information, to encode the first data and the second data into a secure data message using a protocol, and to transmit the first data and the second data in real time via the communication module to various devices.

19 Claims, 21 Drawing Sheets

(51) Int. Cl.
- *A61B 5/024* (2006.01)
- *B60N 2/00* (2006.01)
- *B60W 50/14* (2020.01)
- *G06V 20/59* (2022.01)
- *G16H 30/20* (2018.01)
- *H04N 5/33* (2023.01)

(52) U.S. Cl.
CPC . *B60W 2420/403* (2013.01); *B60W 2540/221* (2020.02); *B60W 2540/223* (2020.02); *B60W 2556/45* (2020.02)

(58) Field of Classification Search
CPC ...... B60N 2/002; G06V 20/593; G16H 30/20; H04N 5/33
See application file for complete search history.

(56) References Cited

U.S. PATENT DOCUMENTS

| | | | |
|---|---|---|---|
| 10,486,590 B2 | 11/2019 | Kirsch et al. | |
| 10,812,593 B2 | 10/2020 | Haidar et al. | |
| 2002/0140215 A1* | 10/2002 | Breed | B60R 11/0241 280/735 |
| 2008/0021730 A1* | 1/2008 | Holla | G16H 80/00 705/2 |
| 2012/0232749 A1* | 9/2012 | Schoenberg | B60R 21/01526 340/457 |
| 2013/0198737 A1* | 8/2013 | Ricci | B60R 25/01 717/174 |
| 2013/0201013 A1* | 8/2013 | Schoenberg | B60N 2/2869 340/438 |
| 2013/0314536 A1* | 11/2013 | Frank | B60H 1/00742 348/148 |
| 2016/0200250 A1* | 7/2016 | Westmoreland | B60Q 9/00 340/457.1 |
| 2016/0354027 A1* | 12/2016 | Benson | A61B 5/7282 |
| 2017/0242428 A1* | 8/2017 | Pal | B60K 35/10 |
| 2018/0126872 A1* | 5/2018 | Folino | G08B 21/24 |
| 2018/0281627 A1* | 10/2018 | Ali | B60N 2/2812 |
| 2019/0061772 A1* | 2/2019 | Prinz | B60K 28/06 |
| 2019/0215672 A1* | 7/2019 | Orris | B60H 1/00978 |
| 2019/0279447 A1 | 9/2019 | Ricci | |
| 2020/0383580 A1* | 12/2020 | Shouldice | A61B 5/02416 |
| 2022/0007950 A1* | 1/2022 | Lev | A61B 5/7267 |

\* cited by examiner

EXAMPLE FOR TYPE OF ENCODING OF THE MEDICAL DATA

| MESSAGE HEADER | CONTENT/INFORMATION |
| --- | --- |
| EVENT TYPE/ EMERGENCY TYPE | EMG-TYP \| HEALTH EMERGENCY \| HIGH URGENCY \| CHOKING |
| OCCUPANT INFORMATION | OCP- INF \| JOHN^DOE \| AGE \| WEIGHT \| GENDER \| HEIGHT \|ADDRESS |
| HEALTH PARAMETERS | HLT-PMT \| HEART RATE \| BP \| TEMP\| |
| VEHICLE DETAILS | VEH-DTL \| VEHICLE ID\| VEHICLE LOCATION |
| OCCUPANT SEATING DETAILS | OCP-SDT \| RIGHT SIDE PASSENGER SEAT IN A CHILD CAR SEAT |
| OCCUPANT PRE-HEALTH CONDITION DETAILS | OCP-PHC \| DIABETES |
| OCCUPANT ALLERGY DETAILS | OCP-ALD \| NIL |
| EMERGENCY CONTACT DETAILS | EMG-CNT \|ROE^MARIE\|SPO\| (216) 555-0123\|EC\| |
| OTHER OCCUPANTS OF THE VEHICLE | OTR-DTL \| JAMES^DOE |

FIG. 4

EXAMPLE MESSAGE TO VEHICLE INFOTAINMENT SYSTEM

| MESSAGE HEADER | CONTENT/INFORMATION |
|---|---|
| OCCUPANT INFORMATION | JOHN^DOE \| AGE \| WEIGHT \| GENDER \| HEIGHT \|ADDRESS |
| VEHICLE LOCATION | X : Y \| LOCATION NAME \| NEARBY LANDMARK |
| VEHICLE DETAILS | VOLVO^CAR \| CAR NUMBER \| CAR COLOR \| CAR OWNER |
| EVENT TYPE/ EMERGENCY TYPE | HEALTH EMERGENCY \| LOW URGENCY\| FEVER 100°F |

FIG. 6A

EXAMPLE MESSAGE TO HOSPITALS/ EMERGENCY CARE

| MESSAGE HEADER | CONTENT/INFORMATION |
|---|---|
| EVENT TYPE/ EMERGENCY TYPE | HEALTH EMERGENCY \| HIGH URGENCY \| CHOKING |
| OCCUPANT INFORMATION | JOHN^DOE \| AGE \| WEIGHT \| GENDER \| HEIGHT \|ADDRESS |
| HEALTH PARAMETERS | HEART RATE \| BP \| TEMP\| |
| VEHICLE DETAILS | VEHICLE ID\| VEHICLE LOCATION |
| OCCUPANT SEATING DETAILS | RIGHT SIDE PASSENGER SEAT IN A CHILD CAR SEAT |
| OCCUPANT PRE-HEALTH CONDITION DETAILS | DIABETES |
| OCCUPANT ALLERGY DETAILS | NIL |
| EMERGENCY CONTACT DETAILS | \|ROE^MARIE\|SPO\|(216) 555-0123\|EC\| |
| OTHER OCCUPANTS OF THE VEHICLE | JAMES^DOE |

FIG. 6B

APPARATUS FOR COMMUNICATIVELY CONNECTING A CAR SEAT TO RETRIEVE HEALTH DATA

FIELD OF THE INVENTION

The present disclosure relates generally to the vehicle communication field. More specifically, the present disclosure relates to systems and methods for communicating medical data through a protocol by establishing secure communication with the vehicle seat.

BACKGROUND

The connected vehicle infrastructure provides a platform for collecting and utilizing vehicle data that can be used advantageously in a wide variety of applications. Such applications are not limited to vehicle control and infotainment, but may also involve vehicle safety. One such safety issue is the availability of situational awareness.

The problem in today's cars is that there is no way to know if a child, rear facing, or an occupant seated in a vehicle is having a medical issue, such as choking, high fever, and low vital signs.

Therefore, there is a need for a system and method that can communicate a health issue securedly in real-time and provide suggestions when an emergency, for example a health emergency, is detected.

SUMMARY

The following presents a summary to provide a basic understanding of one or more embodiments described herein. This summary is not intended to identify key or critical elements or delineate any scope of the different embodiments and/or any scope of the claims. The sole purpose of the summary is to present some concepts in a simplified form as a prelude to the more detailed description presented herein.

An embodiment relates to a system, wherein the system is configured to be a component of a vehicle. The system comprises a sensor, an image sensor, a display, a connector, a communication module, and a processor. The processor is configured to detect a vehicle seat in the vehicle; establish a secured connection with the vehicle seat through the connector; receive a first data from the sensor and a second data from the image sensor through the connector, the first data and the second data being indicative of an information gathered regarding at least one parameter related to at least one of a condition of the vehicle seat, a health and wellness of an occupant of the vehicle, and the connector being configured to facilitate gathering of the information; encode the first data and the second data by identifying protected health information for transmission of a secure data message using a protocol; and transmit the first data and the second data in real time via the communication module to an application installed in a central server thereon, the application being configured to facilitate receipt of the first data and the second data from the central server.

An embodiment relates to method comprising detecting a vehicle seat in a vehicle; establishing a secure connection with the vehicle seat through a connector; receive a first data from a sensor and a second data from an image sensor through a connector, the first data and the second data being indicative of an information gathered regarding at least one parameter related to at least one of a condition of the vehicle seat, a health and wellness of an occupant of the vehicle, and the connector being configured to facilitate gathering of the information; encoding the first data and the second data by identifying protected health information for transmission of a secure data message using a protocol; and transmitting the first data and the second data in real time via the communication module to an application installed in a central server thereon, the application being configured to facilitate receipt of the first data and the second data from the central server.

An embodiment relates to a non-transitory computer storage medium storing a sequence of instructions, which when executed by a processor, causes detecting a vehicle seat in a vehicle; establishing a secure connection with the vehicle seat through a connector; receive a first data from a sensor and a second data from an image sensor through a connector, the first data and the second data being indicative of information gathered regarding at least one parameter related to at least one of a condition of the vehicle seat, a health and wellness of an occupant of the vehicle, and the connector being configured to facilitate gathering of the information; encoding the first data and the second data by identifying protected health information for transmission of a secure data message using a protocol; and transmitting the first data and the second data in real time via the communication module to an application installed in a central server thereon, the application being configured to facilitate receipt of the first data and the second data from the central server.

An embodiment relates to a system. The system is configured to be a component of a vehicle. The system comprises a sensor, an image sensor, a display, a connector, a communication module; a processor. The processor is configured to detect a vehicle seat in the vehicle; establish a secured connection with the vehicle seat through the connector; receive a first data from the sensor, a second data from the image sensor and a third data from a wearable device through the connector, the first data, the second data and the third data being indicative of an information gathered regarding at least one parameter related to at least one of a condition of the vehicle seat, a health and wellness of an occupant, and the connector being configured to facilitate gathering of the information; encode the first data, the second data and the third data by identifying protected health information for transmission of a secure data message using a protocol; and transmit the first data, second data and the third data in real time via the communication module to an application installed in a central server thereon, the application being configured to facilitate receipt of the first data, second data and the third data from the central server.

An embodiment relates to a method comprising detecting a vehicle seat in a vehicle; establishing a secure connection with the vehicle seat through a connector; receive a first data from a sensor, a second data from an image sensor and a third data from a wearable device through a connector, the first data, the second data and the third data being indicative of an information gathered regarding at least one parameter related to at least one of a condition of the vehicle seat, a health and wellness of a patient, and the connector being configured to facilitate gathering of the information; encoding the first data, the second data and the third data by identifying protected health information for transmission of a secure data message using a protocol; and transmitting the first data, second data and the third data in real time via communication module to an application installed in a central server, thereon, the application being configured to facilitate receipt of the first data, second data and the third data from the central server.

An embodiment relates to a non-transitory computer storage medium storing a sequence of instructions, which when executed by a processor, causes detecting a vehicle seat in a vehicle; establishing a secure connection with the vehicle seat through the connector; receive a first data from a sensor, a second data from an image sensor and a third data from a wearable device through a connector, the first data, the second data and the third data being indicative of an information gathered regarding at least one parameter related to at least one of a condition of the vehicle seat, a health and wellness of a patient, and the connector being configured to facilitate gathering of the information; encoding the first data, the second data and the third data by identifying protected health information for transmission of a secure data message using a protocol; and transmitting the first data, second data and the third data in real time via a communication module to an application installed in a central server thereon, the application being configured to facilitate receipt of the first data, second data and the third data from the central server.

An embodiment relates to a system, configured to receive a software application installation package over a computer network; and install the software application onto a computing hardware associated with a vehicle. The software application comprises set of instructions executable by the computing hardware and stored in a non-transitory storage medium that, when executed, cause the computing hardware to implement operations comprising detecting a vehicle seat in the vehicle, establishing a secure connection with the vehicle seat through a connector, receive a first data from a sensor and a second data from an image sensor through the connector, the first data and the second data being indicative of an information gathered regarding at least one parameter related to at least one of a condition of the vehicle seat, a health and wellness of an occupant of the vehicle, and the connector being configured to facilitate gathering of the information, encoding the first data and the second data by identifying protected health information for transmission of a secure data message using a protocol, and transmitting the first data and the second data in real time via a communication module to an application installed in a central server thereon, the application being configured to facilitate receipt of the first data and the second data from the central server.

An embodiment relates to a system, configured to receive a software application installation package over a computer network, and install the software application onto a computing hardware associated with a vehicle. The software application comprises set of instructions executable by the computing hardware and stored in a non-transitory storage medium that, when executed, cause the computing hardware to implement operations comprising detecting a vehicle seat in the vehicle, establishing a secure connection with the vehicle seat through a connector, receive a first data from a sensor, a second data from an image sensor and a third data from a wearable device through the connector, the first data, the second data and the third data being indicative of an information gathered regarding at least one parameter related to at least one of a condition of the vehicle seat, a health and wellness of a patient, and the connector being configured to facilitate gathering of the information, encoding the first data, the second data and the third data by identifying protected health information for transmission of a secure data message using a protocol, and transmitting the first data, the second data and the third data in real time via a communication module to an application installed in a central server thereon, the application being configured to facilitate receipt of the first data, the second data and the third data from the central server.

BRIEF DESCRIPTION OF THE FIGURES

These and other aspects of the present invention will now be described in more detail, with reference to the appended drawings showing exemplary embodiments of the present invention, in which:

FIG. 4 shows an example emergency message and content of the message in the encoded format

FIG. 6A shows an example emergency message and content of the message that may be used for broadcasting or communicating with the vehicle infotainment system according to an embodiment.

FIG. 6B shows an example emergency message and content of the message that may be used for broadcasting or communicating with an emergency contact or a medical care facility according to an embodiment.

Figure 1:
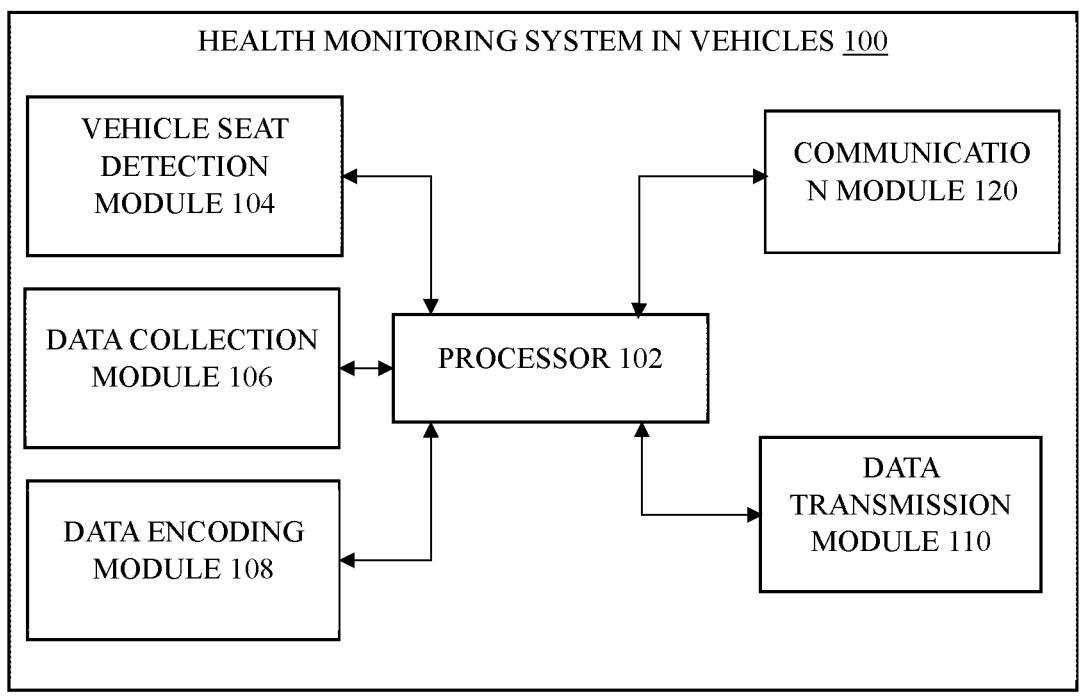
FIG. 1 shows a block diagram of various components of a system for communicating health data in one embodiment.

Other features of the present embodiments will be apparent from the accompanying drawings and the detailed description that follows.

DETAILED DESCRIPTION

For simplicity and clarity of illustration, the figures illustrate the general manner of construction. The description and figures may omit the descriptions and details of well-known features and techniques to avoid unnecessarily obscuring the present disclosure. The figures exaggerate the dimensions of some of the elements relative to other elements to help improve understanding of embodiments of the present disclosure. The same reference numeral in different figures denotes the same elements.

Although the herein detailed description contains many specifics for the purpose of illustration, a person of ordinary skill in the art will appreciate that many variations and alterations to the details are considered to be included herein.

Accordingly, the embodiments herein are without any loss of generality to, and without imposing limitations upon, any claims set forth. The terminology used herein is for the purpose of describing particular embodiments only and is not limiting. Unless defined otherwise, all technical and scientific terms used herein have the same meaning as commonly understood by one with ordinary skill in the art to which this disclosure belongs.

As used herein, the articles "a" and "an" used herein refer to one or to more than one (i.e., to at least one) of the grammatical object of the article. By way of example, "an element" means one element or more than one element. Moreover, usage of articles "a" and "an" in the subject specification and annexed drawings construe to mean "one or more" unless specified otherwise or clear from context to mean a singular form.

As used herein, the terms "example" and/or "exemplary" mean serving as an example, instance, or illustration. For the avoidance of doubt, such examples do not limit the herein described subject matter. In addition, any aspect or design described herein as an "example" and/or "exemplary" is not necessarily preferred or advantageous over other aspects or designs, nor does it preclude equivalent exemplary structures and techniques known to those of ordinary skill in the art.

As used herein, the terms "first," "second," "third," and the like in the description and in the claims, if any, distinguish between similar elements and do not necessarily describe a particular sequence or chronological order. The terms are interchangeable under appropriate circumstances such that the embodiments herein are, for example, capable of operation in sequences other than those illustrated or otherwise described herein. Furthermore, the terms "include," "have," and any variations thereof, cover a non-exclusive inclusion such that a process, method, system, article, device, or apparatus that comprises a list of elements is not necessarily limiting to those elements, but may include other elements not expressly listed or inherent to such process, method, system, article, device, or apparatus.

As used herein, the terms "left," "right," "front," "back," "top," "bottom," "over," "under" and the like in the description and in the claims, if any, are for descriptive purposes and not necessarily for describing permanent relative positions. The terms so used are interchangeable under appropriate circumstances such that the embodiments of the apparatus, methods, and/or articles of manufacture described herein are, for example, capable of operation in other orientations than those illustrated or otherwise described herein.

No element act, or instruction used herein is critical or essential unless explicitly described as such. Furthermore, the term "set" includes items (e.g., related items, unrelated items, a combination of related items and unrelated items, etc.) and may be interchangeable with "one or more". Where only one item is intended, the term "one" or similar language is used. Also, the terms "has," "have," "having," or the like are open-ended terms. Further, the phrase "based on" means "based, at least in part, on" unless explicitly stated otherwise.

As used herein, the terms "system," "device," "unit," and/or "module" refer to a different component, component portion, or component of the various levels of the order. However, other expressions that achieve the same purpose may replace the terms.

As used herein, the terms "couple," "coupled," "couples," "coupling," and the like refer to connecting two or more elements mechanically, electrically, and/or otherwise. Two or more electrical elements may be electrically coupled together, but not mechanically or otherwise coupled together. Coupling may be for any length of time, e.g., permanent, or semi-permanent or only for an instant. "Electrical coupling" includes electrical coupling of all types. The absence of the word "removably," "removable," and the like, near the word "coupled" and the like does not mean that the coupling, etc. in question is or is not removable.

As used herein, the term "or" means an inclusive "or" rather than an exclusive "or." That is, unless specified otherwise, or clear from context, "X employs A or B" means any of the natural inclusive permutations. That is, if X employs A; X employs B; or X employs both A and B, then "X employs A or B" is satisfied under any of the foregoing instances.

As used herein, two or more elements or modules are "integral" or "integrated" if they operate functionally together. Two or more elements are "non-integral" if each element can operate functionally independently.

As used herein, the term "real-time" refers to operations conducted as soon as practically possible upon occurrence of a triggering event. A triggering event can include receipt of data necessary to execute a task or to otherwise process information. Because of delays inherent in transmission and/or in computing speeds, the term "real-time" encompasses operations that occur in "near" real-time or somewhat delayed from a triggering event. In a number of embodiments, "real-time" can mean real-time less a time delay for processing (e.g., determining) and/or transmitting data. The particular time delay can vary depending on the type and/or amount of the data, the processing speeds of the hardware, the transmission capability of the communication hardware, the transmission distance, etc. However, in many embodiments, the time delay can be less than approximately one second, two seconds, five seconds, or ten seconds.

As used herein, the term "approximately" can mean within a specified or unspecified range of the specified or unspecified stated value. In some embodiments, "approximately" can mean within plus or minus ten percent of the stated value. In other embodiments, "approximately" can mean within plus or minus five percent of the stated value.

In further embodiments, "approximately" can mean within plus or minus three percent of the stated value. In yet other embodiments, "approximately" can mean within plus or minus one percent of the stated value.

Other specific forms may embody the present invention without departing from its spirit or characteristics. The described embodiments are in all respects illustrative and not restrictive. Therefore, the appended claims rather than the description herein indicate the scope of the invention. All variations which come within the meaning and range of equivalency of the claims are within their scope.

As used herein, the term "component" broadly construes hardware, firmware, and/or a combination of hardware, firmware, and software.

Digital electronic circuitry, or in computer software, firmware, or hardware, including the structures disclosed in this specification and their structural equivalents, or in combinations of one or more of them may realize the implementations and all of the functional operations described in this specification. Implementations may be as one or more computer program products i.e., one or more modules of computer program instructions encoded on a computer-readable medium for execution by, or to control the operation of, data processing apparatus. The computer-readable medium may be a machine-readable storage device, a machine-readable storage substrate, a memory device, a composition of matter affecting a machine-readable propagated signal, or a combination of one or more of them. The term "computing system" encompasses all apparatus, devices, and machines for processing data, including by way of example, a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal (e.g., a machine-generated electrical, optical, or electromagnetic signal) that encodes information for transmission to a suitable receiver apparatus.

The actual specialized control hardware or software code used to implement these systems and/or methods is not limiting to the implementations. Thus, any software and any hardware can implement the systems and/or methods based on the description herein without reference to specific software code.

A computer program (also known as a program, software, software application, script, or code) is written in any appropriate form of programming language, including compiled or interpreted languages. Any appropriate form, including a standalone program or a module, component, subroutine, or other unit suitable for use in a computing environment may deploy it. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may execute on one computer or on multiple computers that are located at one site or distributed across multiple sites and interconnected by a communication network.

One or more programmable processors, executing one or more computer programs to perform functions by operating on input data and generating output, perform the processes and logic flows described in this specification. The processes and logic flows may also be performed by, and apparatus may also be implemented as, special purpose logic circuitry, for example, without limitation, a Field Programmable Gate Array (FPGA), an Application Specific Integrated Circuit (ASIC), Application Specific Standard Products (ASSPs), System-On-a-Chip (SOC) systems, Complex Programmable Logic Devices (CPLDs), etc.

Processors suitable for the execution of a computer program include, by way of example, both general and special purpose microprocessors, and any one or more processors of any appropriate kind of a digital computer. A processor will receive instructions and data from a read-only memory or a random-access memory or both. Elements of a computer can include a processor for performing instructions and one or more memory devices for storing instructions and data. A computer will also include, or is operatively coupled to receive data, transfer data or both, to/from one or more mass storage devices for storing data e.g., magnetic disks, magneto optical disks, optical disks, or solid-state disks. However, a computer need not have such devices. Moreover, another device, e.g., a mobile telephone, a personal digital assistant (PDA), a mobile audio player, a Global Positioning System (GPS) receiver, etc. may embed a computer. Computer-readable media suitable for storing computer program instructions and data include all forms of non-volatile memory, media and memory devices, including, by way of example, semiconductor memory devices (e.g., Erasable Programmable Read-Only Memory (EPROM), Electronically Erasable Programmable Read-Only Memory (EEPROM), and flash memory devices), magnetic disks (e.g., internal hard disks or removable disks), magneto optical disks (e.g. Compact Disc Read-Only Memory (CD ROM) disks, Digital Versatile Disk-Read-Only Memory (DVD-ROM) disks) and solid-state disks. Special purpose logic circuitry may supplement or incorporate the processor and the memory.

To provide for interaction with a user, a computer may have a display device, e.g., a Cathode Ray Tube (CRT) or Liquid Crystal Display (LCD) monitor, for displaying information to the user, and a keyboard and a pointing device, e.g., a mouse or a trackball, by which the user may provide input to the computer. Other kinds of devices provide for interaction with a user as well. For example, feedback to the user may be any appropriate form of sensory feedback, e.g., visual feedback, auditory feedback, or tactile feedback; and a computer may receive input from the user in any appropriate form, including acoustic, speech, or tactile input.

A computing system that includes a back-end component, e.g., a data server, or that includes a middleware component, e.g., an application server, or that includes a front-end component, e.g., a client computer having a graphical user interface or a Web browser through which a user may interact with an implementation, or any appropriate combination of one or more such back-end, middleware, or front-end components, may realize implementations described herein. Any appropriate form or medium of digital data communication, e.g., a communication network may interconnect the components of the system. Examples of communication networks include a Local Area Network (LAN) and a Wide Area Network (WAN), e.g., Intranet and Internet.

The computing system may include clients and servers. A client and server are remote from each other and typically interact through a communication network. The relationship of the client and server arises by virtue of computer programs running on the respective computers and having a client-server relationship to each other.

Embodiments of the present invention may comprise or utilize a special purpose or general purpose computer including computer hardware. Embodiments within the scope of the present invention may also include physical and other computer-readable media for carrying or storing computer-executable instructions and/or data structures. Such computer-readable media can be any media accessible by a general purpose or special purpose computer system. Computer-readable media that store computer-executable instructions are physical storage media. Computer-readable media that carry computer-executable instructions are transmission media. Thus, by way of example and not limitation, embodiments of the invention can comprise at least two distinct kinds of computer-readable media: physical computer-readable storage media and transmission computer-readable media.

Although the present embodiments described herein are with reference to specific example embodiments it will be evident that various modifications and changes may be made to these embodiments without departing from the broader spirit and scope of the various embodiments. For example, hardware circuitry (e.g., Complementary Metal Oxide Semiconductor (CMOS) based logic circuitry), firmware, software (e.g., embodied in a non-transitory machine-readable medium), or any combination of hardware, firmware, and software may enable and operate the various devices, units, and modules described herein. For example, transistors, logic gates, and electrical circuits (e.g., Application Specific Integrated Circuit (ASIC) and/or Digital Signal Processor (DSP) circuit) may embody the various electrical structures and methods.

In addition, a non-transitory machine-readable medium and/or a system may embody the various operations, processes, and methods disclosed herein. Accordingly, the specification and drawings are illustrative rather than restrictive.

Physical computer-readable storage media includes RAM, ROM, EEPROM, CD-ROM or other optical disk storage (such as CDs, DVDs, etc.), magnetic disk storage or other magnetic storage devices, solid-state disks or any other medium. They store desired program code in the form of computer-executable instructions or data structures which can be accessed by a general purpose or special purpose computer.

As used herein, the term "network" refers to one or more data links that enable the transport of electronic data between computer systems and/or modules and/or other electronic devices. When a network or another communications connection (either hardwired, wireless, or a combination of hardwired or wireless) transfers or provides information to a computer, the computer properly views the connection as a transmission medium. A general purpose or special purpose computer access transmission media that can include a network and/or data links which carry desired program code in the form of computer-executable instructions or data structures. The scope of computer-readable media includes combinations of the above, that enable the transport of electronic data between computer systems and/or modules and/or other electronic devices.

Further, upon reaching various computer system components, program code in the form of computer-executable instructions or data structures can be transferred automatically from transmission computer-readable media to physical computer-readable storage media (or vice versa). For example, computer-executable instructions or data structures received over a network or data link can be buffered in RAM within a Network Interface Module (NIC), and then eventually transferred to computer system RAM and/or to less volatile computer-readable physical storage media at a computer system. Thus, computer system components that also (or even primarily) utilize transmission media may include computer-readable physical storage media.

Computer-executable instructions comprise, for example, instructions and data which cause a general purpose computer, special purpose computer, or special purpose processing device to perform a certain function or group of functions. The computer-executable instructions may be, for example, binary, intermediate format instructions such as assembly language, or even source code. Although the subject matter herein described is in a language specific to structural features and/or methodological acts, the described features or acts described do not limit the subject matter defined in the claims. Rather, the herein described features and acts are example forms of implementing the claims.

While this specification contains many specifics, these do not construe as limitations on the scope of the disclosure or of the claims, but as descriptions of features specific to particular implementations. A single implementation may implement certain features described in this specification in the context of separate implementations. Conversely, multiple implementations separately or in any suitable sub-combination may implement various features described herein in the context of a single implementation. Moreover, although features described herein as acting in certain combinations and even initially claimed as such, one or more features from a claimed combination may in some cases be excised from the combination, and the claimed combination may be directed to a sub-combination or variation of a sub-combination.

Similarly, while operations depicted herein in the drawings in a particular order to achieve desired results, this should not be understood as requiring that such operations be performed in the particular order shown or in sequential order or that all illustrated operations be performed, to achieve desirable results. In certain circumstances, multitasking and parallel processing may be advantageous. Moreover, the separation of various system components in the implementations should not be understood as requiring such separation in all implementations, and it should be understood that the described program components and systems may be integrated together in a single software product or packaged into multiple software products.

Even though particular combinations of features are recited in the claims and/or disclosed in the specification, these combinations are not intended to limit the disclosure of possible implementations. Other implementations are within the scope of the claims. For example, the actions recited in the claims may be performed in a different order and still achieve desirable results. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

Further, a computer system including one or more processors and computer-readable media such as computer memory may practice the methods. In particular, one or more processors execute computer-executable instructions, stored in the computer memory, to perform various functions such as the acts recited in the embodiments.

Those skilled in the art will appreciate that the invention may be practiced in network computing environments with many types of computer system configurations including personal computers, desktop computers, laptop computers, message processors, hand-held devices, multiprocessor systems, microprocessor-based or programmable consumer electronics, network PCs, minicomputers, mainframe computers, mobile telephones, PDAs, pagers, routers, switches, etc. Distributed system environments where local and remote computer systems, which are linked (either by hardwired data links, wireless data links, or by a combination of hardwired and wireless data links) through a network, both perform tasks may also practice the invention. In a distributed system environment, program modules may be located in both local and remote memory storage devices.

Computer readable program instructions described herein are downloadable to respective computing/processing devices from a computer readable storage medium and/or to an external computer or external storage device via a network, for example, the Internet, a local area network, a wide area network and/or a wireless network. The network can comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the one or more embodiments described herein can be assembler instructions, instruction-set-architecture (ISA) instructions, machine instructions, machine dependent instructions, microcode, firmware instructions, state-setting data, configuration data for integrated circuitry, and/or source code and/or object code written in any combination of one or more programming languages, including an object oriented programming language such as Smalltalk, C++ or the like, and/or procedural programming languages, such as the "C" programming language and/or similar programming languages. The computer readable program instructions can execute entirely on a computer, partly on a computer, as a stand-alone software package, partly on a computer and/or partly on a remote computer or entirely on the remote computer and/or server. In the latter scenario, the remote computer can be connected to a computer through any type of network, including a local area network (LAN) and/or a wide area network (WAN), and/or the connection can be made to an external computer (for example, through the Internet using an Internet Service Provider). In one or more embodiments, electronic circuitry including, for example, programmable logic circuitry, field-programmable gate arrays (FPGA), and/or programmable logic arrays (PLA) can execute the computer readable program instructions by utilizing state information of the computer readable program instructions to personalize the electronic circuitry, in order to perform aspects of the one or more embodiments described herein.

Aspects of the one or more embodiments described herein are described with reference to flowchart illustrations and/or block diagrams of methods, apparatus (systems), and computer program products according to one or more embodiments described herein. Each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer and/or other programmable data processing apparatus to produce a machine, such that the instructions, which execute via the processor of the computer or other programmable data processing apparatus, can create means for implementing the functions/acts specified in the flowchart and/or block diagram block or blocks. These computer readable program instructions can also be stored in a computer readable storage medium that can direct a computer, a programmable data processing apparatus and/or other devices to function in a particular manner, such that the computer readable storage medium having instructions stored therein can comprise an article of manufacture including instructions which can implement aspects of the function/act specified in the flowchart and/or block diagram block or blocks. The computer readable program instructions can also be loaded onto a computer, other programmable data processing apparatus and/or other device to cause a series of operational acts to be performed on the computer, other programmable apparatus and/or other device to produce a computer implemented process, such that the instructions which execute on the computer, other programmable apparatus and/or other device implement the functions/acts specified in the flowchart and/or block diagram block or blocks.

The flowcharts and block diagrams in the figures illustrate the architecture, functionality and/or operation of possible implementations of systems, computer-implementable methods and/or computer program products according to one or more embodiments described herein. In this regard, each block in the flowchart or block diagrams can represent a module, segment and/or portion of instructions, which comprises one or more executable instructions for implementing the specified logical function(s). In one or more alternative implementations, the functions noted in the blocks can occur out of the order noted in the Figures. For example, two blocks shown in succession can be executed substantially concurrently, and/or the blocks can sometimes be executed in the reverse order, depending upon the functionality involved. It will also be noted that each block of the block diagrams and/or flowchart illustration, and/or combinations of blocks in the block diagrams and/or flowchart illustration, can be implemented by special purpose hardware-based systems that can perform the specified functions and/or acts and/or carry out one or more combinations of special purpose hardware and/or computer instructions.

While the subject matter described herein is in the general context of computer-executable instructions of a computer program product that runs on a computer and/or computers, those skilled in the art will recognize that the one or more embodiments herein also can be implemented in combination with one or more other program modules. Program modules include routines, programs, components, data structures, and/or the like that perform particular tasks and/or implement particular abstract data types. Moreover, other computer system configurations, including single-processor and/or multiprocessor computer systems, mini-computing devices, mainframe computers, as well as computers, hand-held computing devices (e.g., PDA, phone), microprocessor-based or programmable consumer and/or industrial electronics and/or the like can practice the herein described computer-implemented methods. Distributed computing environments, in which remote processing devices linked through a communications network perform tasks, can also practice the illustrated aspects. However, stand-alone computers can practice one or more, if not all aspects of the one or more embodiments described herein. In a distributed computing environment, program modules can be located in both local and remote memory storage devices.

As used in this application, the terms "component," "system," "platform," "interface," and/or the like, can refer to and/or can include a computer-related entity or an entity related to an operational machine with one or more specific functionalities. The entities described herein can be either hardware, a combination of hardware and software, software, or software in execution. For example, a component can be, but is not limited to being, a process running on a processor, a processor, an object, an executable, a thread of execution, a program and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system and/or across a network such as the Internet with other systems via the signal). As another example, a component can be an apparatus with specific functionality provided by mechanical parts operated by electric or electronic circuitry, which is operated by a software and/or firmware application executed by a processor. In such a case, the processor can be internal and/or external to the apparatus and can execute at least a part of the software and/or firmware application. As yet another example, a component can be an apparatus that provides specific functionality through electronic components without mechanical parts, where the electronic components can include a processor and/or other means to execute software and/or firmware that confers at least in part the functionality of the electronic components. In an aspect, a component can emulate an electronic component via a virtual machine, e.g., within a cloud computing system.

As it is employed in the subject specification, the term "processor" can refer to any computing processing unit and/or device comprising, but not limited to, single-core processors; single-processors with software multithread execution capability; multi-core processors; multi-core processors with software multithread execution capability; multi-core processors with hardware multithread technology; parallel platforms; and/or parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, and/or any combination thereof designed to perform the functions described herein. Further, processors can exploit nano-scale architectures such as, but not limited to, molecular based transistors, switches and/or gates, in order to optimize space usage and/or to enhance performance of related equipment. A combination of computing processing units can implement a processor.

Herein, terms such as "store," "storage," "data store," data storage," "database," and any other information storage component relevant to operation and functionality of a component refer to "memory components," entities embodied in a "memory," or components comprising a memory. Memory and/or memory components described herein can be either volatile memory or nonvolatile memory or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, and/or nonvolatile random access memory (RAM) (e.g., ferroelectric RAM (FeRAM). Volatile memory can include RAM, which can function as external cache memory, for example. By way of illustration and not limitation, RAM can be available in many forms such as synchronous RAM (SRAM), dynamic RAM (DRAM), synchronous DRAM (SDRAM), double data rate SDRAM (DDR SDRAM), enhanced SDRAM (ESDRAM), Synch link DRAM (SLDRAM), direct Rambus RAM (DRRAM), direct Rambus dynamic RAM (DRDRAM) and/or Rambus dynamic RAM (RDRAM). Additionally, the described memory components of systems and/or computer-implemented methods herein include, without being limited to including, these and/or any other suitable types of memory.

The embodiments described herein include mere examples of systems and computer-implemented methods. It is, of course, not possible to describe every conceivable combination of components and/or computer-implemented methods for purposes of describing the one or more embodiments, but one of ordinary skill in the art can recognize that many further combinations and/or permutations of the one or more embodiments are possible. Furthermore, to the extent that the terms "includes," "has," "possesses," and the like are used in the detailed description, claims, appendices and/or drawings such terms are intended to be inclusive in a manner similar to the term "comprising" as "comprising" is interpreted when employed as a transitional word in a claim.

As defined herein, "approximately" may mean within a specified or unspecified range of the specified or unspecified stated value. In some embodiments, "approximately" may mean within plus or minus ten percent of the stated value. In other embodiments, "approximately" may mean within plus or minus five percent of the stated value. In further embodiments, "approximately" may mean within plus or minus three percent of the stated value. In yet other embodiments, "approximately" may mean within plus or minus one percent of the stated value.

As used herein, the term component is intended to be broadly construed as hardware, firmware, and/or a combination of hardware and software.

Implementations and all of the functional operations described in this specification is realized in digital electronic circuitry, or in computer software, firmware, or hardware, including the structures disclosed in this specification and their structural equivalents, or in combinations of one or more of them. Implementations is realized as one or more computer program products i.e., one or more modules of computer program instructions encoded on a computer-readable medium for execution by, or to control the operation of, data processing apparatus. The computer-readable medium is a machine-readable storage device, a machine-readable storage substrate, a memory device, a composition of matter affecting a machine-readable propagated signal, or a combination of one or more of them. The term "computing system" encompasses all apparatus, devices, and machines for processing data, including by way of example, a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal (e.g., a machine-generated electrical, optical, or electromagnetic signal) that is generated to encode information for transmission to a suitable receiver apparatus.

The actual specialized control hardware or software code used to implement these systems and/or methods is not limited to the implementations. Thus, the operation and behavior of the systems and/or methods described herein without reference to specific software code, it being understood that any software and any hardware is designed to implement the systems and/or methods based on the description herein.

A computer program (also known as a program, software, software application, script, or code) is written in any appropriate form of programming language, including compiled or interpreted languages, and it is deployed in any appropriate form, including as a standalone program or as a module, component, subroutine, or other unit suitable for use in a computing environment. A computer program does not necessarily correspond to a file in a file system. A program is stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program is deployed to be executed on one computer or on multiple computers that are located at one site or distributed across multiple sites and interconnected by a communication network.

The processes and logic flows described in this specification are performed by one or more programmable processors executing one or more computer programs to perform functions by operating on input data and generating output. The processes and logic flows may also be performed by, and apparatus may also be implemented as, special purpose logic circuitry, for example, without limitation, a Field Programmable Gate Array (FPGA), an Application Specific Integrated Circuit (ASIC), Application Specific Standard Products (ASSPs), System-On-a-Chip (SOC) systems, Complex Programmable Logic Devices (CPLDs), etc.

Processors suitable for the execution of a computer program include, by way of example, both general and special purpose microprocessors, and any one or more processors of any appropriate kind of digital computer. Generally, a processor will receive instructions and data from a read-only memory or a random-access memory or both. Elements of a computer may include a processor for performing instructions and one or more memory devices for storing instructions and data. Generally, a computer will also include, or be operatively coupled to receive data, transfer data or both, to/from one or more mass storage devices for storing data e.g., magnetic disks, magneto optical disks, optical disks, or solid-state disks. However, a computer need not have such devices. Moreover, a computer is embedded in another device, e.g., a mobile telephone, a personal digital assistant (PDA), a mobile audio player, a Global Positioning System (GPS) receiver, etc. Computer-readable media suitable for storing computer program instructions and data include all forms of non-volatile memory, media and memory devices, including, by way of example, semiconductor memory devices (e.g., Erasable Programmable Read-Only Memory (EPROM), Electronically Erasable Programmable Read-Only Memory (EEPROM), and flash memory devices), magnetic disks (e.g., internal hard disks or removable disks), magneto optical disks (e.g. Compact Disc Read-Only Memory (CD-ROM) disks, Digital Versatile Disk-Read-Only Memory (DVD-ROM) disks) and solid-state disks. The processor and the memory are supplemented by, or incorporated in, special purpose logic circuitry.

To provide for interaction with a user, implementations are realized on a computer having a display device, e.g., a Cathode Ray Tube (CRT) or Liquid Crystal Display (LCD) monitor, for displaying information to the user, and a keyboard and a pointing device, e.g., a mouse or a trackball, by which the user may provide input to the computer. Other kinds of devices is used to provide for interaction with a user as well; for example, feedback provided to the user is any appropriate form of sensory feedback, e.g., visual feedback, auditory feedback, or tactile feedback; and input from the user is received in any appropriate form, including acoustic, speech, or tactile input.

Implementations is realized in a computing system that includes a back-end component, e.g., a data server, or that includes a middleware component, e.g., an application server, or that includes a front-end component, e.g., a client computer having a graphical user interface or a Web browser through which a user may interact with an implementation, or any appropriate combination of one or more such back-end, middleware, or front-end components. The components of the system are interconnected by any appropriate form or medium of digital data communication, e.g., a communication network. Examples of communication networks include a Local Area Network (LAN) and a Wide Area Network (WAN), e.g., Intranet and Internet.

The computing system may include clients and servers. A client and server are generally remote from each other and typically interact through a communication network. The relationship of the client and server arises by virtue of computer programs running on the respective computers and having a client-server relationship to each other.

Embodiments of the present invention may comprise or utilize a special purpose or general purpose computer including computer hardware. Embodiments within the scope of the present invention may also include physical and other computer-readable media for carrying or storing computer-executable instructions and/or data structures. Such computer-readable media is any media that is accessed by a general purpose or special purpose computer system. Computer-readable media that store computer-executable instructions are physical storage media. Computer-readable media that carry computer-executable instructions are transmission media. Thus, by way of example and not limitation, embodiments of the invention may comprise at least two distinctly different kinds of computer-readable media: physical computer-readable storage media and transmission computer-readable media.

Although the present embodiments have been described with reference to specific example embodiments, it will be evident that various modifications and changes is made to these embodiments without departing from the broader spirit and scope of the various embodiments. For example, the various devices, units, and modules described herein is enabled and operated using hardware circuitry (e.g., Complementary Metal Oxide Semiconductor (CMOS) based logic circuitry), firmware, software (e.g., embodied in a non-transitory machine-readable medium), or any combination of hardware, firmware, and software. For example, the various electrical structures and methods is embodied using transistors, logic gates, and electrical circuits (e.g., Application Specific Integrated Circuit (ASIC) and/or Digital Signal Processor (DSP) circuit).

In addition, it will be appreciated that the various operations, processes, and methods disclosed herein is embodied in a non-transitory machine-readable medium and/or a system. Accordingly, the specification and drawings are to be regarded in an illustrative rather than a restrictive sense.

Physical computer-readable storage media includes RAM, ROM, EEPROM, CD-ROM or other optical disk storage (such as CDs, DVDs, etc.), magnetic disk storage or other magnetic storage devices, solid-state disks or any other medium which is used to store desired program code means in the form of computer-executable instructions or data structures and which is accessed by a general purpose or special purpose computer.

Further, upon reaching various computer system components, program code means in the form of computer-executable instructions or data structures is transferred automatically from transmission computer-readable media to physical computer-readable storage media (or vice versa). For example, computer-executable instructions or data structures received over a network or data link is buffered in Random Access Memory (RAM) within a network interface module (NIC), and then eventually transferred to computer system RAM and/or to less volatile computer-readable physical storage media at a computer system. Thus, computer-readable physical storage media is included in computer system components that also (or even primarily) utilize transmission media.

Computer-executable instructions comprise, for example, instructions and data which cause a general purpose computer, special purpose computer, or special purpose processing device to perform a certain function or group of functions. The computer-executable instructions are, for example, binary, intermediate format instructions such as assembly language, or even source code. Although the subject matter has been described in language specific to structural features and/or methodological acts, it is to be understood that the subject matter defined in the claims is not necessarily limited to the described features or acts described. Rather, the described features and acts are disclosed as example forms of implementing the claims.

While this specification contains many specifics, these should not be construed as limitations on the scope of the disclosure or of what is claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable sub-combination. Moreover, although features are described as acting in certain combinations and even initially claimed as such, one or more features from a claimed combination may in some cases be excised from the combination, and the claimed combination is directed to a sub-combination or variation of a sub-combination.

Similarly, while operations are depicted in the drawings in a particular order to achieve desired results, this should not be understood as requiring that such operations be performed in the particular order shown or in sequential order or that all illustrated operations be performed, to achieve desirable results. In certain circumstances, multitasking and parallel processing is advantageous. Moreover, the separation of various system components in the implementations should not be understood as requiring such separation in all implementations, and it should be understood that the described program components and systems may generally be integrated together in a single software product or packaged into multiple software products.

Even though particular combinations of features are recited in the claims and/or disclosed in the specification, these combinations are not intended to limit the disclosure of possible implementations. Other implementations are within the scope of the following claims. For example, the actions recited in the claims is performed in a different order and still achieve desirable results. In fact, many of these features is combined in ways not specifically recited in the claims and/or disclosed in the specification. Although each dependent claim listed below may directly depend on only one claim, the disclosure of possible implementations includes each dependent claim in combination with every other claim in the claim set.

Further, the methods are practiced by a computer system including one or more processors and computer-readable media such as computer memory. In particular, the computer memory may store computer-executable instructions that when executed by one or more processors cause various functions to be performed such as the acts recited in the embodiments.

The disclosure provides illustration and description but is not intended to be exhaustive or to limit the implementations to the precise form disclosed. Modifications and variations are possible in light of the above disclosure or is acquired from practice of the implementations.

Those skilled in the art will appreciate that the invention is practiced in network computing environments with many types of computer system configurations including personal computers, desktop computers, laptop computers, message processors, hand-held devices, multiprocessor systems, microprocessor-based or programmable consumer electronics, network PCs, minicomputers, mainframe computers, mobile telephones, PDAs, pagers, routers, switches, etc. The invention may also be practiced in distributed system environments where local and remote computer systems, which are linked (either by hardwired data links, wireless data links, or by a combination of hardwired and wireless data links) through a network, both perform tasks. In a distributed system environment, program modules are located in both local and remote memory storage devices.

As used herein, the term "Cryptographic protocol" is also known as security protocol or encryption protocol. It is an abstract or concrete protocol that performs a security-related function and applies cryptographic methods often as sequences of cryptographic primitives. A protocol describes how the algorithms should be used. A sufficiently detailed protocol includes details about data structures and representations, at which point it is used to implement multiple, interoperable versions of a program.

Cryptographic protocols are widely used for secure application-level data transport. A cryptographic protocol usually incorporates at least some of these aspects: key agreement or establishment, entity authentication, symmetric encryption, and message authentication material construction, secured application-level data transport, non-repudiation methods, secret sharing methods, and secure multi-party computation.

As used herein, the term "IoT" stands for Internet of Things which describes the network of physical objects "things" or objects that are embedded with sensors, software, and other technologies for the purpose of connecting and exchanging data with other devices and systems over the internet.

As used herein "Machine learning" refers to algorithms that give a computer the ability to learn without being explicitly programmed, including algorithms that learn from and make predictions about data. Machine learning algorithms include, but are not limited to, decision tree learning, artificial neural networks (ANN) (also referred to herein as a "neural net"), deep learning neural network, support vector machines, rules-based machine learning, random forest, etc. For the purposes of clarity, algorithms such as linear regression or logistic regression may also be used as part of a machine learning process. However, it is understood that using linear regression or another algorithm as part of a machine learning process is distinct from performing a statistical analysis such as regression with a spreadsheet program. The machine learning process may continually learn and adjust the classifier as new data becomes available and does not rely on explicit or rules-based programming. The ANN is featured with a feedback loop to adjust the system output dynamically as it learns from the new data as it becomes available. In machine learning, backpropagation and feedback loops are used to train the AI/ML model improving the model's accuracy and performance over time.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All variations which come within the meaning and range of equivalency of the claims are to be embraced within their scope.

As defined herein, "approximately" can mean within a specified or unspecified range of the specified or unspecified stated value. In some embodiments, "approximately" can mean within plus or minus ten percent of the stated value. In other embodiments, "approximately" can mean within plus or minus five percent of the stated value. In further embodiments, "approximately" can mean within plus or minus three percent of the stated value. In yet other embodiments, "approximately" can mean within plus or minus one percent of the stated value.

As used herein, the term component is intended to be broadly construed as hardware, firmware, and/or a combination of hardware and software.

Implementations and all of the functional operations described in this specification may be realized in digital electronic circuitry, or in computer software, firmware, or hardware, including the structures disclosed in this specification and their structural equivalents, or in combinations of one or more of them. Implementations may be realized as one or more computer program products i.e., one or more modules of computer program instructions encoded on a computer-readable medium for execution by, or to control the operation of, data processing apparatus. The computer-readable medium may be a machine-readable storage device, a machine-readable storage substrate, a memory device, a composition of matter affecting a machine-readable propagated signal, or a combination of one or more of them. The term "computing system" encompasses all apparatus, devices, and machines for processing data, including by way of example, a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal (e.g., a machine-generated electrical, optical, or electromagnetic signal) that is generated to encode information for transmission to a suitable receiver apparatus.

The actual specialized control hardware or software code used to implement these systems and/or methods is not limited to the implementations. Thus, the operation and behavior of the systems and/or methods described herein without reference to specific software code, it being understood that any software and any hardware can be designed to implement the systems and/or methods based on the description herein.

A computer program (also known as a program, software, software application, script, or code) may be written in any appropriate form of programming language, including compiled or interpreted languages, and it may be deployed in any appropriate form, including as a standalone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry, for example, without limitation, a Field Programmable Gate Array (FPGA), an Application Specific Integrated Circuit (ASIC), Application Specific Standard Products (ASSPs), System-On-a-Chip (SOC) systems, Complex Programmable Logic Devices (CPLDs), etc.

Processors suitable for the execution of a computer program include, by way of example, both general and special purpose microprocessors, and any one or more processors of any appropriate kind of digital computer. Generally, a processor will receive instructions and data from a read-only memory or a random-access memory or both. Elements of a computer can include a processor for performing instructions and one or more memory devices for storing instructions and data. Generally, a computer will also include, or be operatively coupled to receive data, transfer data or both, to/from one or more mass storage devices for storing data e.g., magnetic disks, magneto optical disks, optical disks, or solid-state disks. However, a computer need not have such devices. Moreover, a computer may be embedded in another device, e.g., a mobile telephone, a personal digital assistant (PDA), a mobile audio player, a Global Positioning System (GPS) receiver, etc. Computer-readable media suitable for storing computer program instructions and data include all forms of non-volatile memory, media and memory devices, including, by way of example, semiconductor memory devices (e.g., Erasable Programmable Read-Only Memory (EPROM), Electronically Erasable Programmable Read-Only Memory (EEPROM), and flash memory devices), magnetic disks (e.g., internal hard disks or removable disks), magneto optical disks (e.g. Compact Disc Read-Only Memory (CD-ROM) disks, Digital Versatile Disk-Read-Only Memory (DVD-ROM) disks) and solid-state disks. The processor and the memory may be supplemented by, or incorporated in, special purpose logic circuitry.

To provide for interaction with a user, implementations may be realized on a computer having a display device, e.g., a Cathode Ray Tube (CRT) or Liquid Crystal Display (LCD)

monitor, for displaying information to the user, and a keyboard and a pointing device, e.g., a mouse or a trackball, by which the user may provide input to the computer. Other kinds of devices may be used to provide for interaction with a user as well; for example, feedback provided to the user may be any appropriate form of sensory feedback, e.g., visual feedback, auditory feedback, or tactile feedback; and input from the user may be received in any appropriate form, including acoustic, speech, or tactile input.

Implementations may be realized in a computing system that includes a back-end component, e.g., a data server, or that includes a middleware component, e.g., an application server, or that includes a front-end component, e.g., a client computer having a graphical user interface or a Web browser through which a user may interact with an implementation, or any appropriate combination of one or more such back-end, middleware, or front-end components. The components of the system may be interconnected by any appropriate form or medium of digital data communication, e.g., a communication network. Examples of communication networks include a Local Area Network (LAN) and a Wide Area Network (WAN), e.g., Intranet and Internet.

The computing system may include clients and servers. A client and server are generally remote from each other and typically interact through a communication network. The relationship of the client and server arises by virtue of computer programs running on the respective computers and having a client-server relationship to each other.

Embodiments of the present invention may comprise or utilize a special purpose or general purpose computer including computer hardware. Embodiments within the scope of the present invention may also include physical and other computer-readable media for carrying or storing computer-executable instructions and/or data structures. Such computer-readable media can be any media that can be accessed by a general purpose or special purpose computer system. Computer-readable media that store computer-executable instructions are physical storage media. Computer-readable media that carry computer-executable instructions are transmission media. Thus, by way of example and not limitation, embodiments of the invention can comprise at least two distinctly different kinds of computer-readable media: physical computer-readable storage media and transmission computer-readable media.

Although the present embodiments have been described with reference to specific example embodiments, it will be evident that various modifications and changes may be made to these embodiments without departing from the broader spirit and scope of the various embodiments. For example, the various devices, units, and modules described herein may be enabled and operated using hardware circuitry (e.g., Complementary Metal Oxide Semiconductor (CMOS) based logic circuitry), firmware, software (e.g., embodied in a non-transitory machine-readable medium), or any combination of hardware, firmware, and software. For example, the various electrical structures and methods may be embodied using transistors, logic gates, and electrical circuits (e.g., Application Specific Integrated Circuit (ASIC) and/or Digital Signal Processor (DSP) circuit).

In addition, it will be appreciated that the various operations, processes, and methods disclosed herein may be embodied in a non-transitory machine-readable medium and/or a system. Accordingly, the specification and drawings are to be regarded in an illustrative rather than a restrictive sense.

Physical computer-readable storage media includes Random Access Memory (RAM), Read only memory (ROM), Electrically Erasable Programmable Read-only Memory (EEPROM), Compact Disk Read Only Memory (CD-ROM) or other optical disk storage (such as Compact Disks (CDs), Digital Versatile disks (DVDs), etc.), magnetic disk storage or other magnetic storage devices, solid-state disks or any other medium which can be used to store desired program code means in the form of computer-executable instructions or data structures and which can be accessed by a general purpose or special purpose computer.

Further, upon reaching various computer system components, program code means in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (NIC), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general purpose computer, special purpose computer, or special purpose processing device to perform a certain function or group of functions. The computer-executable instructions may be, for example, binary, intermediate format instructions such as assembly language, or even source code. Although the subject matter has been described in language specific to structural features and/or methodological acts, it is to be understood that the subject matter defined in the claims is not necessarily limited to the described features or acts described. Rather, the described features and acts are disclosed as example forms of implementing the claims.

While this specification contains many specifics, these should not be construed as limitations on the scope of the disclosure or of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable sub-combination. Moreover, although features may be described as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings in a particular order to achieve desired results, this should not be understood as requiring that such operations be performed in the particular order shown or in sequential order or that all illustrated operations be performed, to achieve desirable results. In certain circumstances, multitasking and parallel processing may be advantageous. Moreover, the separation of various system components in the implementations should not be understood as requiring such separation in all implementations, and it should be understood that the described program components and systems may generally be integrated together in a single software product or packaged into multiple software products.

Even though particular combinations of features are recited in the claims and/or disclosed in the specification, these combinations are not intended to limit the disclosure of possible implementations. Other implementations are within the scope of the following claims. For example, the actions recited in the claims may be performed in a different order and still achieve desirable results. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

Further, the methods may be practiced by a computer system including one or more processors and computer-readable media such as computer memory. In particular, the computer memory may store computer-executable instructions that when executed by one or more processors cause various functions to be performed such as the acts recited in the embodiments.

The disclosure provides illustration and description but is not intended to be exhaustive or to limit the implementations to the precise form disclosed. Modifications and variations are possible in light of the above disclosure or may be acquired from practice of the implementations.

Those skilled in the art will appreciate that the invention may be practiced in network computing environments with many types of computer system configurations including personal computers, desktop computers, laptop computers, message processors, hand-held devices, multiprocessor systems, microprocessor-based or programmable consumer electronics, network PCs, minicomputers, mainframe computers, mobile telephones, PDAs, pagers, routers, switches, etc. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

The following terms and phrases, unless otherwise indicated, shall be understood to have the following meanings.

As used herein, the term "Cryptographic protocol" is also known as security protocol or encryption protocol. It is an abstract or concrete protocol that performs a security-related function and applies cryptographic methods often as sequences of cryptographic primitives. A protocol describes how the algorithms should be used. A sufficiently detailed protocol includes details about data structures and representations, at which point it can be used to implement multiple, interoperable versions of a program.

Cryptographic protocols are widely used for secure application-level data transport. A cryptographic protocol usually incorporates at least some of these aspects: key agreement or establishment, entity authentication, symmetric encryption, and message authentication material construction, secured application-level data transport, non-repudiation methods, secret sharing methods, and secure multi-party computation.

As used herein, the term "IoT" stands for Internet of Things which describes the network of physical objects "things" or objects that are embedded with sensors, software, and other technologies for the purpose of connecting and exchanging data with other devices and systems over the internet.

As used herein "Machine learning" refers to algorithms that give a computer the ability to learn without being explicitly programmed, including algorithms that learn from and make predictions about data. Machine learning algorithms include, but are not limited to, decision tree learning, artificial neural networks (ANN) (also referred to herein as a "neural net"), deep learning neural network, support vector machines, rules-based machine learning, random forest, etc. For the purposes of clarity, algorithms such as linear regression or logistic regression can also be used as part of a machine learning process. However, it is understood that using linear regression or another algorithm as part of a machine learning process is distinct from performing a statistical analysis such as regression with a spreadsheet program. The machine learning process can continually learn and adjust the classifier as new data becomes available and does not rely on explicit or rules-based programming. The ANN may be featured with a feedback loop to adjust the system output dynamically as it learns from the new data as it becomes available. In machine learning, backpropagation and feedback loops are used to train the AI/ML model improving the model's accuracy and performance over time.

Statistical modeling relies on finding relationships between variables (e.g., mathematical equations) to predict an outcome.

As used herein, the term "Data mining" is a process used to turn raw data into useful information.

As used herein, the term "Data acquisition" is the process of sampling signals that measure real world physical conditions and converting the resulting samples into digital numeric values that can be manipulated by a computer. Data acquisition systems typically convert analog waveforms into digital values for processing. The components of data acquisition systems include sensors to convert physical parameters to electrical signals, signal conditioning circuitry to convert sensor signals into a form that can be converted to digital values, and analog-to-digital converters to convert conditioned sensor signals to digital values. Stand-alone data acquisition systems are often called data loggers.

As used herein, the term "Dashboard" is a type of interface that visualizes particular Key Performance Indicators (KPIs) for a specific goal or process. It is based on data visualization and infographics.

As used herein, a "Database" is a collection of information that is organized so that it can be easily accessed, managed, and updated. Computer databases typically contain aggregations of data records or files.

As used herein, the term "Data set" (or "Dataset") is a collection of data. In the case of tabular data, a data set corresponds to one or more database tables, where every column of a table represents a particular variable, and each row corresponds to a given record of the data set in question. The data set lists values for each of the variables, such as height and weight of an object, for each member of the data set. Each value is known as a datum. Data sets can also consist of a collection of documents or files.

As used herein, a "Sensor" is a device that measures physical input from its environment and converts it into data that can be interpreted by either a human or a machine. Most sensors are electronic (the data is converted into electronic data), but some are simpler, such as a glass thermometer, which presents visual data.

The term "vehicle" as used herein refers to a thing used for transporting people or goods. Automobiles, cars, trucks, buses etc. are examples of vehicles.

The term "electronic control unit" (ECU), also known as an "electronic control module" (ECM), is a system that controls one or more subsystems. An ECU may be installed in a car or other motor vehicle. It may refer to many ECUs, and can include but not limited to, Engine Control Module (ECM), Powertrain Control Module (PCM), Transmission Control Module (TCM), Brake Control Module (BCM) or Electronic Brake Control Module (EBCM), Central Control Module (CCM), Central Timing Module (CTM), General Electronic Module (GEM), Body Control Module (BCM), and Suspension Control Module (SCM). ECUs together are sometimes referred to collectively as the vehicles' computer or vehicles' central computer and may include separate computers. In an example, the electronic control unit can be embedded system in automotive electronics. In another example, the electronic control unit is wirelessly coupled with the automotive electronics.

The term "infotainment system" or "in-vehicle infotainment system" (IVI) as used herein refers to a combination of systems which are used to deliver entertainment and information. In an example, the information may be delivered to the driver and the passengers of a vehicle through audio/video interfaces, control elements like touch screen displays, button panel, voice commands, and more. Some of the main components of an in-vehicle infotainment systems are integrated head-unit, heads-up display, high-end Digital Signal Processors (DSPs), and Graphics Processing Units (GPUs) to support multiple displays, operating systems, Controller Area Network (CAN), Low-Voltage Differential Signaling (LVDS), and other network protocol support (as per the requirement), connectivity modules, automotive sensors integration, digital instrument cluster, etc.

The term "environment" or "surrounding" as used herein refers to surroundings and the space in which a vehicle is navigating. It refers to dynamic surroundings in which a vehicle is navigating which includes other vehicles, obstacles, pedestrians, lane boundaries, traffic signs and signals, speed limits, potholes, snow, water logging etc. The term "communication system" or "communication module" as used herein refers to a system which enables the information exchange between at least two points. The process of transmission and reception of information is called communication. The major elements of communication include, but are not limited to, a transmitter of information, channel or medium of communication and a receiver of information.

The term "communication system" or "communication module" as used herein refers to a system which enables the information exchange between two points. The process of transmission and reception of information is called communication. The major elements of communication include but are not limited to a transmitter of information, channel or medium of communication and a receiver of information.

The term "autonomous mode" as used herein refers to an operating mode which is independent and unsupervised.

The term "autonomous communication" as used herein comprises communication over a period with minimal supervision under different scenarios and is not solely or completely based on pre-coded scenarios or pre-coded rules or a predefined protocol. Autonomous communication, in general, happens in an independent and an unsupervised manner. The term "protocol unit" or "message protocol unit" as used herein defines the rules and sequencing of communication structure between various types of units.

The term "autonomous mode" as used herein refers to an operating mode which is independent and unsupervised.

The term "communication system" or "communication module" as used herein refers to a system which enables the information exchange between two points. The process of transmission and reception of information is called communication. The major elements of communication include but are not limited to a transmitter of information, channel or medium of communication and a receiver of information.

The term "connection" as used herein refers to a communication link. It refers to a communication channel that connects two or more devices for the purpose of data transmission. It may refer to a physical transmission medium such as a wire, or to a logical connection over a multiplexed medium such as a radio channel in telecommunications and computer networking. A channel is used for information transfer of, for example a digital bit stream, from one or several senders to one or several receivers. A channel has a certain capacity for transmitting information, often measured by its bandwidth in Hertz (Hz) or its data rate in bits per second. For example, a Vehicle-to-Vehicle (V2V) communication may wirelessly exchange information about the speed, location and heading of surrounding vehicles.

The term "communication" as used herein refers to the transmission of information and/or data from one point to another. Communication may be by means of electromagnetic waves. It is also a flow of information from one point, known as the source, to another, the receiver. Communication comprises one of the following: transmitting data, instructions, and information or a combination of data, instructions, and information. Communication happens between any two communication systems or communicating units. The term "in communication with" may refer to any coupling, connection, or interaction using electrical signals to exchange information or data, using any system, hardware, software, protocol, or format, regardless of whether the exchange occurs wirelessly or over a wired connection. The term communication includes systems that combine other more specific types of communication, such as V2I (Vehicle-to-Infrastructure), V2I (Vehicle-to-Infrastructure), V2N (Vehicle-to-Network), V2V (Vehicle-to-Vehicle), V2P (Vehicle-to-Pedestrian), V2D (Vehicle-to-Device) and V2G (Vehicle-to-Grid) and Vehicle-to-Everything (V2X) communication. V2X communication is the transmission of information from a vehicle to any entity that may affect the vehicle, and vice versa. The main motivations for developing V2X are occupant safety, road safety, traffic efficiency and energy efficiency. Depending on the underlying technology employed, there are two types of V2X communication technologies: cellular networks and other technologies that support direct device-to-device communication (such as Dedicated Short-Range Communication (DSRC), Port Community System (PCS), Bluetooth®, Wi-Fi®, etc.). Further, the emergency communication apparatus is configured on a computer with the communication function and is connected for bidirectional communication with the on-vehicle emergency report apparatus by a communication line through a radio station and a communication network such as a public telephone network or by satellite communication through a communication satellite. The emergency communication apparatus is adapted to communicate, through the communication network, with communication terminals including a road management office, a police station, a fire department, and a hospital. The emergency communication apparatus can be also connected online with the communication terminals of the persons concerned, associated with the occupant (the driver receiving the service) of the emergency-reporting vehicle.

The term "autonomous vehicle" also referred to as self-driving vehicle, driverless vehicle, robotic vehicle as used herein refers to a vehicle incorporating vehicular automation, that is, a ground vehicle that can sense its environment and move safely with little or no human input. Self-driving vehicles combine a variety of sensors to perceive their surroundings, such as thermographic cameras, Radio Detection and Ranging (radar), Light Detection and Ranging (lidar), Sound Navigation and Ranging (sonar), Global Positioning System (GPS), odometry and inertial measurement unit. Control systems, designed for the purpose, interpret sensor information to identify appropriate navigation paths, as well as obstacles and relevant signage.

The term "rule-based system" as used herein comprises a set of facts of a scenario and a set of rules for how to deal with the set of facts comprising if and then statements, wherein the scenario is predefined in a system.

The term "protocol" as used herein refers to a procedure required to initiate and maintain communication; a formal set of conventions governing the format and relative timing of message exchange between two communications terminals; a set of conventions that govern the interaction of processes, devices, and other components within a system; a set of signaling rules used to convey information or commands between boards connected to the bus; a set of signaling rules used to convey information between agents; a set of semantic and syntactic rules that determine the behavior of entities that interact; a set of rules and formats (semantic and syntactic) that determines the communication behavior of simulation applications; a set of conventions or rules that govern the interactions of processes or applications within a computer system or network; a formal set of conventions governing the format and relative timing of message exchange in a computer system; a set of semantic and syntactic rules that determine the behavior of functional units in achieving meaningful communication; a set of semantic and syntactic rules for exchanging information.

The term "communication protocol" as used herein refers to standardized communication between any two systems. An example communication protocol is of Health Level Seven (HL7). HL7 is a set of international standards used to provide guidance with transferring and sharing data between various healthcare providers. HL7 is a comprehensive framework and related standards for the exchange, integration, sharing, and retrieval of electronic health information.

The term "connection" as used herein refers to a communication link. It refers to a communication channel that connects two or more devices for the purpose of data transmission. It may refer to a physical transmission medium such as a wire, or to a logical connection over a multiplexed medium such as a radio channel in telecommunications and computer networking. A channel is used for information transfer of, for example a digital bit stream, from one or several senders to one or several receivers. A channel has a certain capacity for transmitting information, often measured by its bandwidth in Hertz (Hz) or its data rate in bits per second. For example, a Vehicle-to-Vehicle (V2V) communication may wirelessly exchange information about the speed, location and heading of surrounding vehicles.

The term "alert" or "alert signal" refers to a communication to attract attention. An alert may include visual, tactile, audible alert, and a combination of these alerts to warn drivers or occupants. These alerts allow, drivers or occupants, the ability to act and respond quickly to avoid or navigate through the emergency situation.

The term, "biophysical measurement" as used herein refers to measurement of physical changes that take place over a period of time related to a specific indicator that can be measured using an accepted measurement procedure. This provides statistically reliable data that can form the basis for measuring impact and change. Biophysical sensors monitor metabolites, pH, electrolytes, heart rate, arterial oxygenation, sweat rate, and skin temperature, etc., from biophysical signals. It may refer to any signal in living beings that can be continually measured and monitored. The term may also be referred to as bio-signal and is often used to refer to bioelectrical signals, but it may refer to both electrical and non-electrical signals. It may refer to time-varying signals, although spatial parameter variations are sometimes subsumed as well.

The term, "physiological characteristic" as used herein refers to a characteristic relating to physiology that is indicative of a healthy or normal functioning human. Example physiological characteristics include, but not limited to, heart rate, blood pressure, respiration, body temperature, etc.

The term, "bio signal" is any signal in human beings that can be continually measured or monitored. Example bio signals include electrocardiogram (ECG), electroencephalogram (EEG), electromyogram (EMG), electrooculogram (EOG), galvanic skin response, magnetoencephalography (MEG), etc.

As used herein, a "bio-sensor" or "biosensor" is an analytical device, used for the detection of a chemical substance, that combines a biological component with a physicochemical detector. The sensitive biological element, e.g., tissue, microorganisms, organelles, cell receptors, enzymes, antibodies, nucleic acids, etc., is a biologically derived material or biomimetic component that interacts with, binds with, or recognizes the analyte under study. The biosensor may include pulse oximeter, heart rate sensor, ECG sensor, skin sensors, temperature sensor, blood pressure sensor, impedance sensor etc. In an embodiment, the biosensor includes a biometric device. The biometric device uses automated methods of verifying or recognizing the identity of a living person based on a physiological or behavioral characteristic. These characteristics include fingerprints, facial images, iris, and voice recognition. Information generated or received by the sensors and biosensor may be communicated to the on-board computer or the mobile device for use in autonomous vehicle operation.

The term "rule-based system" as used herein comprises a set of facts of a scenario and a set of rules for how to deal with the set of facts comprising if and then statements, wherein the scenario is predefined in a system.

The term "occupant" as used herein, refers to a passenger in the vehicle and it includes the driver. Passenger and occupant are interchangeably used and refer to a person in the vehicle during a ride.

The term "nearby vehicle" as used herein refers to surrounding vehicles of the user's vehicle and is within reach of at least a communication range of the user's vehicle wherein the communication range is defined as the maximum distance where communication can exist between two antennas, one of which is user's vehicle antenna in a wireless network.

The term "electronic health record system" or "EHR system" refers to electronic record of health-related information on an individual that can be created, gathered, managed, and consulted by authorized clinicians and staff within one health care organization. Health records from the EHR system are usually procured using third-party software suites.

The term "application server" refers to a server that hosts applications or software that delivers a business application through a communication protocol. An application server framework is a service layer model. It includes software components available to a software developer through an application programming interface. It is system software that resides between the operating system (OS) on one side, the external resources such as a database management system (DBMS), communications and Internet services on another side, and the users' applications on the third side.

The term "feature" as used herein in relation to machine learning and pattern recognition, represents or refers to an individual measurable property or characteristic of a phenomenon. Features are usually numeric, but structural features such as strings and graphs are used in syntactic pattern recognition. The concept of "feature" is related to that of explanatory variables used in statistical techniques such as linear regression.

The term "syntactic pattern recognition" or "structural pattern recognition" refers to a form of pattern recognition, in which each object can be represented by a variable-cardinality set of symbolic, nominal features. This allows for representing pattern structures, considering more complex interrelationships between attributes than is possible in the case of flat, numerical feature vectors of fixed dimensionality, that are used in statistical classification. Syntactic pattern recognition can be used instead of statistical pattern recognition if there is clear structure in the patterns. One way to present such a structure is by means of a string of symbols from a formal language. In this case the differences in the structures of the classes are encoded as different grammars. An example of this would be diagnosis of the heart with ECG measurements. ECG waveforms can be approximated with diagonal and vertical line segments. If normal and unhealthy waveforms can be described as formal grammars, measured ECG signal can be classified as healthy or unhealthy by first describing it in terms of the basic line segments and then trying to parse the descriptions according to the grammars.

The term "occupant" as used herein, refers to a passenger in the vehicle and it includes the driver. Passenger and occupant are used interchangeably and refer to a person in the vehicle during a ride.

The term "image sensor" as used herein, refers to a device for recording visual images in the form of photographs, film, or video signals. Image sensor may be a camera and may refer to an infrared camera or a thermographic camera. A thermographic camera is a device that creates an image using infrared (IR) radiation, similar to a normal camera that forms an image using visible light. An infrared camera (also known as a thermal imager) detects and measures the infrared energy of objects. An infrared camera converts infrared data into an electronic image from which surface temperature of the object may be measured.

The term "vehicle seat" as used herein refers to a thing made or used for a person to sit on while traveling in a vehicle. The vehicle seat may be removable. The vehicle seat as referred to herein may be a child car seat that is a removable seat designed to hold a child while riding in the vehicle and the child removable seat usually attaches to a standard seat with hooks or straps.

The term "connector" as used herein refers to a connector that connects geographically separated points. For example, a connector may be a communication connector that transmits information signals. The heart of a communications connector is the transmission medium, which may be a wired or wireless connection. Wired connectors may be optical fibers, coaxial conductors, or twisted wire pairs. Wireless connections may be a Bluetooth connection, Wi-Fi connection or a near field communication connection The term "secure connection" as used herein refers to an encrypted connection that has one or more security protocols to ensure the security of data flowing between two or more nodes. When a connection easily listened to by anyone with the knowledge on how to listen in, or an unencrypted connection is even prone to threats by malicious software and rogue and unexpected events is not encrypted or is not a secured connection.

The term "data" as used herein refers to facts and information. The facts and information may be related to an occupant or a vehicle.

The term "signal" as used herein refers to an electrical or electromagnetic current that is used for carrying data from one device or network to another. A signal is a function that conveys information about a phenomenon. Any quantity that can vary over space or time can be used as a signal to share messages between observers. A start signal, a stop signal, an acknowledgement signal are examples of signal. The term start signal refers to a signal that prepares a device to receive data or to perform a function. In asynchronous serial communication, start signals are used at the beginning of a character that prepares the receiving device for the reception of the code elements. The term acknowledgement signal refers to a signal that is passed between communicating processes, computers, or devices to signify acknowledgment, or receipt of message, as part of a communications protocol The term "predictive diagnostics" as used herein refers to prediction of trends by analyzing the data and predicting trends over the history of the data on the basis of the change in data over a period. For Example, vehicle-specific predictions of components and system conditions in order to optimize the performance of the vehicle, based on status data from the connected vehicle. Sensors continuously monitor the condition of components and systems and transmit the information to the control unit.

A "wearable device," as used herein can include, but is not limited to, a computing device component (e.g., a processor) with circuitry that can be worn or attached to a user. In other words, a wearable device is a computer that is subsumed into the personal space of a user. Wearable devices can include a display and can include various sensors for sensing and determining various parameters of a user. For example, location, motion, and physiological parameters, among others. Some wearable devices have user input and output functionality. Exemplary wearable devices can include, but are not limited to, watches, glasses, clothing, gloves, hats, shirts, jewelry, rings, earrings, necklaces, armbands, leashes, collars, shoes, earbuds, headphones, and personal wellness devices.

The term "cyber security" as used herein refers to application of technologies, processes, and controls to protect systems, networks, programs, devices, and data from cyber-attacks.

The term "cyber security module" as used herein refers to a module comprising application of technologies, processes, and controls to protect systems, networks, programs, devices and data from cyber-attacks and threats. It aims to reduce the risk of cyber-attacks and protect against the unauthorized exploitation of systems, networks, and technologies. It includes, but is not limited to, critical infrastructure security, application security, network security, cloud security, Internet of Things (IoT) security.

The term "encrypt" used herein refers to securing digital data using one or more mathematical techniques, along with a password or "key" used to decrypt the information. It refers to converting information or data into a code, especially to prevent unauthorized access. It may also refer to concealing information or data by converting it into a code. It may also be referred to as cipher, code, encipher, encode. A simple example is representing alphabets with numbers— say, 'A' is '01', 'B' is '02', and so on. For example, a message like "HELLO" will be encrypted as "0805121215," and this value will be transmitted over the network to the recipient(s).

The term "decrypt" used herein refers to the process of converting an encrypted message back to its original format. It is generally a reverse process of encryption. It decodes the encrypted information so that only an authorized user can decrypt the data because decryption requires a secret key or password. This term could be used to describe a method of unencrypting the data manually or unencrypting the data using the proper codes or keys.

The term "cyber security threat" used herein refers to any possible malicious attack that seeks to unlawfully access data, disrupt digital operations, or damage information. A malicious act includes but is not limited to damage data, steal data, or disrupt digital life in general. Cyber threats include, but are not limited to, malware, spyware, phishing attacks, ransomware, zero-day exploits, trojans, advanced persistent threats, wiper attacks, data manipulation, data destruction, rogue software, malvertising, unpatched software, computer viruses, man-in-the-middle attacks, data breaches, Denial of Service (DoS) attacks, and other attack vectors.

The term "hash value" used herein can be thought of as fingerprints for files. The contents of a file are processed through a cryptographic algorithm, and a unique numerical value, the hash value, is produced that identifies the contents of the file. If the contents are modified in any way, the value of the hash will also change significantly. Example algorithms used to produce hash values: the Message Digest-5 (MD5) algorithm and Secure Hash Algorithm-1 (SHA1).

The term "integrity check" as used herein refers to the checking for accuracy and consistency of system related files, data, etc. It may be performed using checking tools that can detect whether any critical system files have been changed, thus enabling the system administrator to look for unauthorized alteration of the system. For example, data integrity corresponds to the quality of data in the databases and to the level by which users examine data quality, integrity, and reliability. Data integrity checks verify that the data in the database is accurate, and functions as expected within a given application.

The term "alarm" as used herein refers to a trigger when a component in a system or the system fails or does not perform as expected. The system may enter an alarm state when a certain event occurs. An alarm indication signal is a visual signal to indicate the alarm state. For example, when the system detects a cyber security threat, a system administrator may be alerted via sound alarm, a message, a glowing LED, a pop-up window, etc. The system reports an alarm indication signal may downstream from a detecting device, to prevent adverse situations or cascading effects.

The term "in communication with" as used herein, refers to any coupling, connection, or interaction using electrical signals to exchange information or data, using any system, hardware, software, protocol, or format, regardless of whether the exchange occurs wirelessly or over a wired connection.

As used herein, the term "cryptographic protocol" is also known as security protocol or encryption protocol. It is an abstract or concrete protocol that performs a security-related function and applies cryptographic methods often as sequences of cryptographic primitives. A protocol describes how the algorithms should be used. A sufficiently detailed protocol includes details about data structures and representations, at which point it can be used to implement multiple, interoperable versions of a program. Cryptographic protocols are widely used for secure application-level data transport. A cryptographic protocol usually incorporates at least some of these aspects: key agreement or establishment, entity authentication, symmetric encryption, and message authentication material construction, secured application-level data transport, non-repudiation methods, secret sharing methods, and secure multi-party computation. Hashing algorithms may be used to verify the integrity of data. Secure Socket Layer (SSL) and Transport Layer Security (TLS), the successor to SSL, are cryptographic protocols that may be used by networking switches to secure data communications over a network.

As used herein, the term "network" may include the Internet, a local area network, a wide area network, or combinations thereof. The network may include one or more networks or communication systems, such as the Internet, the telephone system, satellite networks, cable television networks, and various other private and public networks. In addition, the connections may include wired connections (such as wires, cables, fiber optic lines, etc.), wireless connections, or combinations thereof. Furthermore, although not shown, other computers, systems, devices, and networks may also be connected to the network. Network refers to any set of devices or subsystems connected by links joining (directly or indirectly) a set of terminal nodes sharing resources located on or provided by network nodes. The computers use common communication protocols over digital interconnections to communicate with each other. For example, subsystems may comprise the cloud. Cloud refers to servers that are accessed over the Internet, and the software and databases that run on those servers.

The problem in today's cars is that there is no way to know if a child, rear facing, is having a medical issue, such as choking, high fever, low vital signs. The medical issue may give a particular health and wellness data of the occupant. There needs to be a system that can monitor and provide suggestions when the system detects a health issue.

In cars, there needs to be a system to detect car seats and external seats such as a child car seat and a pet car seat when placed inside the vehicle. The system once detecting the seat may detect the condition of the seat inside the car and the condition of the occupant. The system may generate alerts if the system detects any abnormality in the condition of the seat and the occupant.

An embodiment relates to a system that is configured to be a component of a vehicle. The system comprises a sensor, an image sensor, a display, a connector, a communication module, and a processor. The processor is configured to detect a vehicle seat in the vehicle, establish a secured connection with the vehicle seat through the connector, receive a first data from the sensor and a second data from the image sensor through the connector; the first data and the second data being indicative of information gathered regarding at least one parameter related to at least one of a condition of the vehicle seat, a health and wellness of an occupant of the vehicle, and the connector being configured to facilitate gathering of the information, to encode the first data and the second data by identifying protected health information for transmission of a secure data message using a protocol, and to transmit the first data and the second data in real time via the communication module to an application installed in a central server; thereon, the application being configured to facilitate receipt of the data from the central server.

In an embodiment of the system, the vehicle seat comprises at least one of a car seat, a child car seat, and a pet car seat. In an embodiment of the system, the vehicle seat comprises at least one of a front facing car seat, rear facing car seat and a booster seat.

In an embodiment of the system, the system comprises a plurality of sensors in the vehicle. In an embodiment of the system, the sensor comprises at least one of a seat belt sensor, a position sensor, a pressure sensor, a liquid detection sensor, weight sensor, an infrared sensor, an optical sensor, a moisture sensor, a temperature sensor, and an audio sensor.

In an embodiment of the system, the image sensor comprises an infrared image sensor, and a thermal image sensor. In an embodiment of the system, the image sensor is rotatable at an angle to get an image. In an embodiment of the system, the system comprises a plurality of image sensors. The sensor for monitoring the health data comprises at least one of a heart rate sensor, a temperature sensor, and a blood pressure sensor.

In an embodiment of the system, the first data of the vehicle seat further comprises data related to the vehicle seat position. The first data comprises at least one of a first position of the vehicle seat, a second position of the occupant on the vehicle seat, a weight of the occupant, a height of the occupant, and a pressure on the seat belt. The second data comprises a first image of the vehicle seat's position, a second image of a second position of the occupant on the vehicle seat, and a third image of a size of the vehicle seat according to the height and weight of the occupant.

In an embodiment of the system, the connector comprises at least one of a wired or a wireless connector.

In an embodiment of the system, the system displays a condition of the vehicle seat in real time on a display. In an embodiment of the system, the system displays the condition of the vehicle seat on a vehicle infotainment system. In an embodiment of the system, the system displays the condition of the vehicle seat on a screen of a mobile device having an application.

In an embodiment of the system, the processor is configured to send a start signal to the vehicle seat through the connector and receive an acknowledgement signal from the vehicle seat via the connector to detect the vehicle seat in the vehicle.

In an embodiment of the system, the processor is configured to receive a signal at the communication module from the vehicle seat, to automatically determine if the signal originates from inside the vehicle, and if the signal does not originate from inside the vehicle, to reject the signal, if the signal originates from inside the vehicle, to communicatively connect the communication module to the vehicle seat and receive a message from the vehicle seat.

In an embodiment of the system, the communication module is enabled for at least one of vehicle-to-infrastructure communication, and vehicle-to-everything communication. The vehicle-to-infrastructure communication comprises dedicated short range communication.

In an embodiment of the system, the system displays a condition of the occupant on a display. In an embodiment of the system, the system displays the condition of the occupant on a vehicle infotainment system. In an embodiment, the system displays the condition of the occupant on a display of a mobile device.

FIG. 1 shows a block diagram of various components of a system for communicating health data of an occupant of the vehicle seat according to an embodiment. The system 100 may comprise a processor 102. In an embodiment, the processor 102 can include a plurality of processors. The system 100 may comprise different modules or subsystems, as shown in FIG. 1, which are communicatively coupled, such as vehicle seat detection module 104, data collection module 106, data encoding module 108, data transmission module 110 and communication module 120. In an embodiment, all the modules may be configured into a single module or may comprise separate modules.

In an embodiment, the communication module is enabled for at least one of a vehicle-to-vehicle communication, vehicle-to-infrastructure communication, and vehicle-to-everything communication. The vehicle-to-vehicle communication comprises dedicated short range communication.

The vehicle seat detection module may detect a vehicle seat inside a vehicle. The vehicle may be a car. The vehicle seat may comprise at least one of a normal car seat, a child car seat, and a pet car seat. The vehicle seat comprises at least one of a front facing car seat, rear facing car seat and a booster seat. The vehicle seat is connected to the processor 102 through a connector. The connector may be a wired or a wireless connector. Wired connector may comprise an ethernet, Local area network (LAN), Recommended Standard 232 (RS232), Universal serial Bus (USB), Universal Asynchronous Receive Transmit UART or a controller area network (CAN) connection. A wireless connection may comprise a pair of trans receivers, near field communication, Bluetooth, or Wi-Fi connection. The vehicle seat may comprise a sensor and a camera. The sensor and the camera may detect a condition of the vehicle seat. In an embodiment, the sensor and the camera may detect a condition of the occupant.

When an external car seat is connected into the vehicle such as a child car seat or a pet car seat, the vehicle control system detects external seat. The vehicle seat detection module detects a vehicle seat by the by exchanging handshaking signals to the vehicle seat through the connector. The processor 102 sends a start signal through the connector in order to detect a vehicle seat. If there is a vehicle seat attached at the other end of the connector, the processor 102 may receive an acknowledgement signal from the vehicle seat. Upon receiving the acknowledgement signal, the processor 102 establishes a secured connection with the vehicle seat. The processor 102 may receive a signal at the communication module from the vehicle seat. The processor 102 may further automatically determine if the signal originates from inside the vehicle. If the signal does not originate from inside the vehicle, then the processor 102 is configured to reject the signal. If the signal originates from inside the vehicle, the processor 102 communicatively connects the communication module to the vehicle seat. Then the processor 102 is configured to receive a message from the vehicle seat. Then the processor 102 verifies that the message originated from inside the vehicle. The system analyses and studies the signals that are received by the connector to identify the origin location of the signal. As such, the communication transceivers can create a geo-fence (i.e., a virtual perimeter for a real-world geographic area) around the vehicle that allows the communication system to determine whether received signals are currently originating inside the vehicle.

In an embodiment, the connector includes one or more BLUETOOTH™ transceivers to connect to the vehicle seat and the processor 102. The BLUETOOTH™ transceiver may be paired with a vehicle seat. The BLUETOOTH™ transceiver may conduct communications using the BLUETOOTH™ protocol with the vehicle seat. Information received from and/or sent to the vehicle seat may originate from the communication module.

The connector may also include other communication components that can communicate with different protocols.

For example, the connector may communicate using an 802.11, 802.11G, or other wireless LAN protocol. The wireless LAN router/antenna may communicate with the vehicle seat and the processor 102. Other types of communication devices or components may include an Ethernet LAN. The Ethernet LAN may include one or more hard-wired ports that may be connected within the vehicle seat. There may be other types of protocols or systems used to communicate with the communication system. The components within the communication system may be hardware and/or software and may operate as understood in the art as associated with these communication protocols.

In an embodiment, the system may be operable to interface with a single type of communication component to provide those signals to a processor 102. The processor 102 may be operable to analyze signal characteristics, relay messages, or do other types of processing received from the vehicle seat. The processor 102 can receive signal data from the vehicle seat through the connector. This data may include timestamps, signal attenuation characteristics, Doppler shift characteristics, and other types of characteristics about the signal. The processor 102 analyzes the signal data to determine the location of the source of the signal. This location determination may then be used to determine whether the vehicle seat is provided access to send data to the processor 102.

If the system grants access, the vehicle seat detection module may provide an address to the vehicle seat to provide for inter-device communication or communication from the vehicle to the vehicle seat. The processor 102 may also store data about the signal, the vehicle seat associated with the signal, the user associated with the signal, or other data, in a signal data database. The database may be any type of data structure or data-storage system, for example, an object-oriented database, flat file database, or other types of databases. The data may include any data received and/or processed by the processor 102 and used to identify the source location of the signals. The processor 102 accesses, stores, or manages information in the database.

In an embodiment, the system comprises a universal bus for the health monitoring system. Generally, the method starts with a start operation and ends with an end operation. The method can include more or fewer steps and can arrange the order of the steps differently. The method can be executed as a set of computer-executable instructions executed by a computer system and encoded or stored on a computer readable medium. Hereinafter, the method shall be explained with reference to the systems, components, modules, software, data structures, user interfaces, etc.

The processor 102 may receive a signal from the vehicle seat. One of the receivers of the connector receives the signal, which may include a BLUETOOTH™ transceiver, an 802.11 transceiver, or some other wired receiver. The signal may then be transferred to the processor 102 through the connector.

Further, the processor 102, through the vehicle seat detection module, may determine if the signal originated from inside the vehicle. Various analyses may be performed on the signal or on signal information contained in the signal. If the signal is determined to originate outside the vehicle, the method may proceed where the processor 102 may reject the receipt of the signal. If the signal is determined to have originated from inside the vehicle, the method can proceed, where the vehicle system may make a connection to the vehicle seat through the connector and the processor 102.

The processor 102 may provide an Internet Protocol (IP) address or other type of access such that signals coming from the vehicle seat thereafter are not rejected. Other types of wireless or wired connections may also be made. If the connection is with a BLUETOOTH™ capable vehicle seat, the vehicle system may pair the vehicle seat with a BLUETOOTH™ transceiver. The vehicle system may make several pairings with the processor 102 as there may be two or more BLUETOOTH™ transceivers available. Upon making the connection or pairing, the vehicle system can provide access to the communication bus, such that signals to and from vehicle seat are relayed to the processor 102 of the vehicle system, which may be accessed by the vehicle seat sending the signals. In this way, a communication bus is established through wireless or wired connections.

Figure 2A:
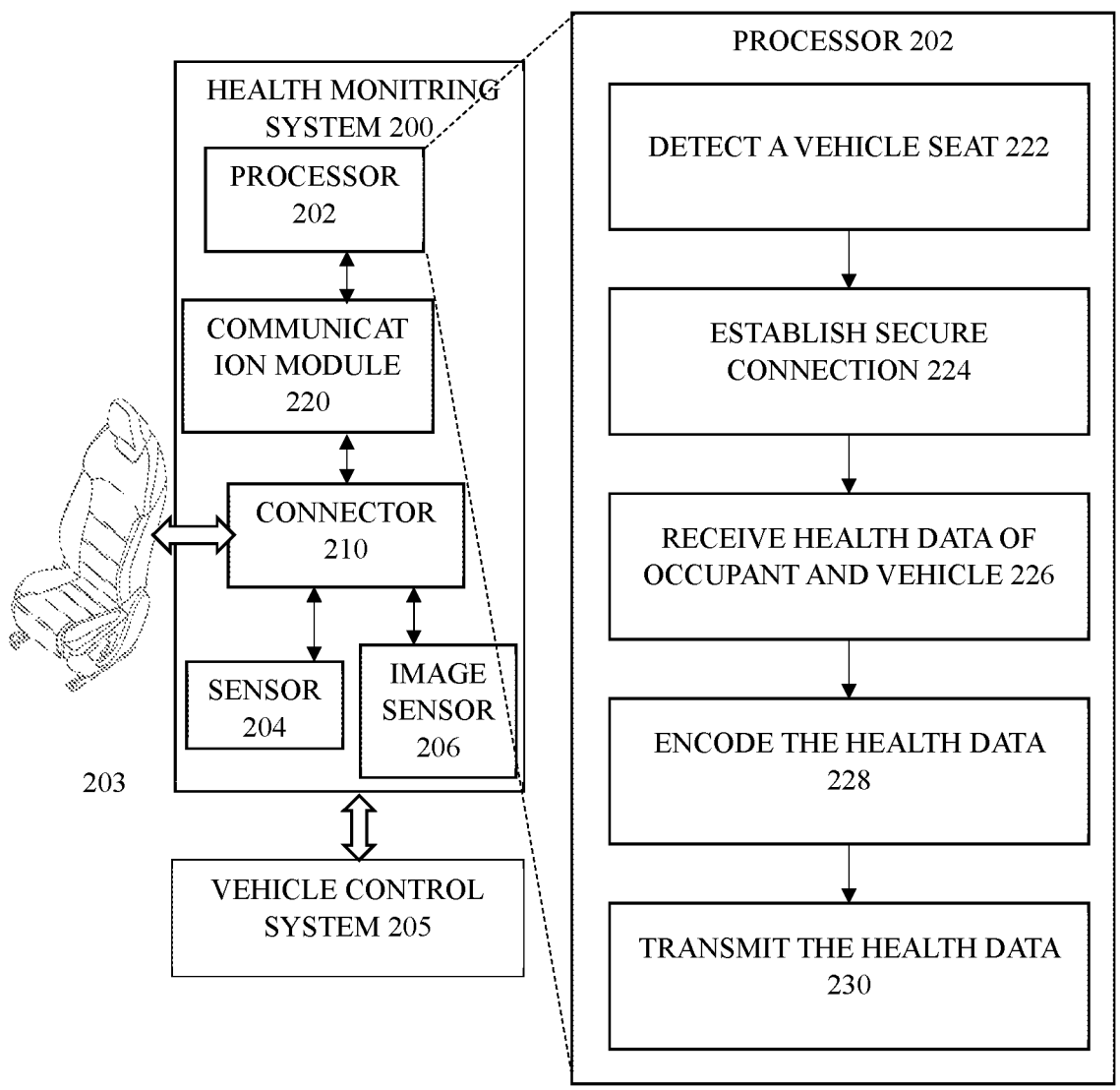
FIG. 2A shows a block diagram for a system to monitor health data in one embodiment.

FIG. 2A shows a block diagram for a system to monitor health data in one embodiment. In an embodiment, the processor 202 may also analyze location information. Beyond the signal characteristics, the processor 202 may receive information from sensors 204 to determine a location of the vehicle seat. Further, the system analyzes the sensor data. Sensor data may include such things as determining if there are occupants and the number of occupants within a vehicle. For example, if an optical sensor can view a vehicle seat within its field of vision and/or if an electromagnetic field sensor determines that there is Electro Magnetic Field (EMF) radiation emanating from a location in the vehicle, then the processor 202 can determine that that signal is originating inside a vehicle.

Once the vehicle control system establishes communication with the vehicle seat, the vehicle seat may transmit signals related to the occupant's state of health. FIG. 2A shows a system to detect a health risk. The system comprises a sensor 204, an image sensor 206, and a processor 202. The processor 202 receives data of vehicle seat 203 and health of an occupant from the image sensor 206 and the sensor 204 through the connector 210. The system to monitor health data communicates with the vehicle seat and the vehicle control system 205 through the communication module 220 via the connector 210.

An embodiment relates to a system, wherein a system is configured to be a component of a vehicle. The system comprises a sensor 204, an image sensor 206, a connector 210, a communication module and a processor 202. The processor 202 is configured to detect a vehicle seat in the vehicle via the connector 210, establish a secure connection with the vehicle seat through the connector 210, receive a first data of the vehicle from the sensor 204, receive a second data from the image sensor 206, process the first data and the second data, and notify a condition of an occupant through the communication module. The vehicle seat comprises at least one of a normal car seat, a child car seat and a pet car seat. The vehicle seat comprises at least one of a front facing car seat, rear facing car seat and a booster seat. The system comprises a plurality of sensors in the vehicle. The sensor 204 comprises at least one of a seat belt sensor, a position sensor, a pressure sensor, a liquid detection sensor, weight sensor, an infrared sensor, an optical sensor, a comfort detection sensor, a moisture sensor, a temperature sensor, and an audio sensor. The image sensor 206 comprises an infrared image sensor, and a thermal image sensor. The sensor comprises at least one of a heart rate sensor, a temperature sensor, a blood pressure sensor, a blood presence sensor, and a blood composition sensor. The connector 210 comprises at least one of a wired or a wireless connector.

In an embodiment, the second data comprises an image of the vehicle seat's position, a second position of the occupant on the vehicle seat, and a size of the vehicle seat according to the height and weight of the occupant. The first data comprises at least one of a first position of the vehicle seat, a second position of the occupant on the vehicle seat, a weight of the occupant, a height of the occupant, and a pressure on the seat belt.

The processor 202 is configured to perform:

The system detects a vehicle seat, at step 222. A start signal is sent from a vehicle control system to the vehicle seat. If the vehicle seat is connected to the vehicle control system through a connector, an acknowledgement is received from the vehicle seat.

Upon receiving the acknowledgement from the vehicle seat, a secure connection is established between the vehicle seat and the vehicle control system, at step 224.

The vehicle control system receives data of the vehicle seat and a health data of the occupant of the vehicle seat, at step 226. The first data comprises at least one of a first position of the vehicle seat, a second position of the occupant on the vehicle seat, a weight of the occupant, a height of the occupant, and a pressure on the seat belt. The second data comprises a first image of the vehicle seat's position, a second image of a second position of the occupant on the vehicle seat.

The received data is then encoded by identifying protected health information for transmission of a secure data message using a protocol similar to the HL7 protocol, at step 228.

At step 230, the encoded message is then transmitted to various recipients such as a medical facility, a vehicle infotainment system, emergency contact and to nearby devices in case of a high urgency condition. In an embodiment, the transmission is in real time via the communication module to an application installed in a central server, thereon, the application is configured to receive the data from the central server.

The occupant's state of health may be determined through image or video processing of the occupant's face and body. For example, the heartbeat of a human can be measured with video processing of the green channel for a red, green, blue (RGB) image sensor. In other examples, the occupant monitoring system may detect choking, coughing, sneezing, and sweating through similar video processing methodologies. Using combinations of these information streams, a sophisticated software algorithm may make predictions and suggest an emergency, a severity, and a possible suggestion to address the emergency situation. Using machine learning and video processing, an occupant's weight trends and organ failure (e.g., kidney failure) may be determined through changes in the skin color (blotchiness, droopiness, darkness). The facial expression feature is measured by picking up an image of the face of the occupant by the charge coupled device (CCD) image sensor 206, or the like, installed in the vehicle, pointed directly at the face of the occupant, and measuring the facial expression features of the occupant from the image data using the image processing technique. The image sensor 206 may be installed on the interior side of the roof of the vehicle, which can have more than one degree of freedom to monitor the occupant from different angles. In an embodiment, there may be a plurality of image sensor 206s monitoring the occupant from different angles. The image sensor 206 detects a conscious state of the occupant, and the position of the occupant.

In an embodiment, it is a system for detecting if a vehicle occupant is experiencing a problematic health situation, which may be an emergency situation, and responding to those situations. In the system, sensors in a vehicle monitor, record, and/or detect physiological characteristics of an occupant of the vehicle. Additionally, environmental sensors monitor, record, and/or detect environmental characteristics of the vehicle itself. By detecting the physiological characteristics of the vehicle occupant, receiving physiological characteristic measurements, and using machine learning, the system can determine a baseline for each physiological characteristic corresponding to a specific vehicle occupant (e.g., a driver of the vehicle). The system can then compare newly received physiological characteristic measurements with the baseline for that particular physiological characteristic to determine whether the newly received physiological characteristic measurement is not within the limits of the baseline.

In some embodiments, occupant health and wellness data may include biophysical data of the occupant. In some embodiments, biophysical data of the occupant may be collected or otherwise monitored through one or more sensors, such as sensors implementable in a vehicle. Sensors may be located at various locations in or on the vehicle, in the car seats, in the child car seats, in the belts, on the steering wheel, mirrors, etc. In some embodiments, sensors may be in contact with, or worn by, the occupant to monitor or collect biophysical data. For example, a sensor 204 may be a heart rate sensor embedded in a seatbelt of the vehicle and configured to provide a heart rate reading of the heart rate of the occupant as biophysical data when the seatbelt is engaged with or worn by the driver. As another example, a sensor may be a blood pressure sensor disposed on an armrest of a car seat of the vehicle and configured to provide a blood pressure reading of the blood pressure of the occupant when the occupant places his or her arm on the armrest. Likewise, sensor 204 may include a thermometer, a respiratory rate monitor, a blood glucose monitor, or the like, to provide biophysical data of the occupant, such as a body temperature reading, a respiration reading, a blood glucose reading, or the like. In some embodiments, sensor 204 may include a video image sensor 206 or an infrared image sensor to capture video(s) and/or image(s) of the occupant and provide imagery data indicative of a body movement, an eye movement, or a facial distortion of the occupant as biophysical data. Using facial detection or other image processing techniques, a processor 202 may analyze the video(s) or image(s) and accordingly determine the emergency situation and its severity. For example, a sensor may include a video image sensor 206 and a processor 202 may analyze a video received from the video image sensor 206 and find that the occupant may have passed out in the vehicle seat when there is no occupant movement for a determined time threshold. The processor 202 may determine this condition to be very likely an emergency related to the health of the occupant, at which the emergency severity may be given a scale of 1-10, where 10 being very severe or life threatening.

In some embodiments, occupant health and wellness data may also include a medical history of the occupant, and/or a set of emergency-triggering thresholds of the occupant. Medical history may include information on one or more pre-existing medical condition(s) of the occupant, such as hypertension, asthma, or diabetes for example. The system transmits the medical history of the driver from a remote location, such as a cloud server of a medical service provider and received as other data through a communication device thereof. Alternatively, medical history of the occupant may be readily stored in memory of the health monitoring system. The processor 202 may analyze the medical history of the occupant while determining emergency severity. For example, the processor 202 may analyze medical history and find that the occupant is a diabetic, and thus may monitor a blood glucose reading of biophysical data received from a blood glucose sensor among sensor 204. In some embodiments, occupant wellness data of the occupant may include a set of emergency-triggering thresholds associated with the specific occupant, which may be provided by a medical doctor or medical service provider. For example, in the case of the diabetic occupant, the set of emergency-triggering thresholds may include a "life-threatening" low-bound blood glucose threshold of 80 mg/dl (milligram per deciliter), and a "non-life-threatening" low-bound blood glucose threshold of 100 mg/dl, as dictated by a medical service provider. In this example, the processor 202 may determine that there is no potential emergency incident should the blood glucose sensor report a reading higher than 100 mg/dl. Moreover, the processor 202 may determine that there is a potential emergency incident of "life-threatening" severity should the blood glucose sensor report a reading lower than 80 mg/dl. Furthermore, the processor 202 may determine that there is a potential emergency incident of "less-than-life-threatening" severity should the blood glucose sensor report a reading between 80 mg/dl and 100 mg/dl.

In still other embodiments, sensor 204 in the car determines where particular passengers are sitting or located. Sensor 204 can include seat sensor, weight sensor on seats, spring sensors on/in seats, heat sensors on/in seats, motion sensors on/in seats, switches, image sensor 206, heat detectors, or combinations of two or more thereof. The sensor comprises at least one of a seat belt sensor, a position sensor, a pressure sensor, a liquid detection sensor, weight sensor, an infrared sensor, an optical sensor, a comfort detection sensor, a moisture sensor, a temperature sensor, and an audio sensor. The first data of the vehicle seat further comprises data related to the vehicle seat position and if the vehicle seat is secured in the right position. The second data comprises an image of the vehicle seat's position and a size of the vehicle seat according to the height and weight of the occupant. The first data comprises at least one of a first position of the vehicle seat, a second position of the occupant on the vehicle seat, a weight of the occupant, a height of the occupant, and a pressure on the seat belt. In case the size of vehicle seat is not matching the height of the occupant, the system generates an alert for change of vehicle seat. The system checks a vehicle seat position and if the vehicle seat is not in proper position, the system generates an alert for fixing the vehicle seat position. A seat belt pressure sensor checks if the seat belt is fastened properly. In case of a loose seat belt or improper connection of seat belt, the system generates an alert to tighten, or to readjust the connection to, the seat belt. In an embodiment the vehicle control system may send signals to tighten the seat belt automatically. In case the occupant is not sitting properly in the vehicle seat, the system generates the alert that the occupant might fall, and the position of the occupant is not proper.

In some embodiments, the processor 202s may determine emergency severity based on a correlation among occupant health and wellness data, vehicle motion data, driver wellness data and/or driver distraction or distress data. The vehicle motion data may include various motion parameters of the vehicle, such as a speed of the vehicle, a moving direction of the vehicle, and/or a distance between the vehicle and a nearby object. The one or more motion detectors positioned in or on the vehicle collects or monitors the motion data of the vehicle. The motion detectors may include one or more of a speedometer, a global positioning device, a video image sensor 206, and a proximity sensor.

An embodiment relates to a system, wherein a system is configured to be a component of a vehicle. The system comprises a sensor, an image sensor, a display, a connector 210, a communication module, and a processor 202. The processor 202 is configured to detect a vehicle seat in the vehicle, establish a secured connection with the vehicle seat through the connector 210, receive a first data from the sensor and a second data from the image sensor and a third data from a wearable device through the connector 210; the first data, the second data and the third data being indicative of information gathered regarding at least one parameter related to at least one of a condition of the vehicle seat, a health and wellness of an occupant, and the connector 210 being configured to facilitate gathering of the information, to encode the first data and the second data and the third data by identifying protected health information for transmission of a secure data message using a protocol, and to transmit the received first data, second data and the third data in real time via the communication module to an application installed in a central server; thereon, the application being configured to facilitate receipt of the data from the central server.

In an embodiment of the system, the sensor comprises at least one of a seat belt sensor, a position sensor, a pressure sensor, a liquid detection sensor, weight sensor, an infrared sensor, an optical sensor, a moisture sensor, a temperature sensor, and an audio sensor.

In an embodiment of the system, the wearable device for monitoring the health data comprises at least one of a heart rate sensor, a temperature sensor, and a blood pressure sensor.

In an embodiment of the system, the first data comprises at least one of a first position of the vehicle seat, a second position of the occupant on the vehicle seat, a weight of the occupant, a height of the occupant, and a pressure on the seat belt.

In an embodiment of the system, the second data comprises a first image of the vehicle seat's position, a second image of a second position of the occupant on the vehicle seat, and a third image of a size of the vehicle seat according to the height and weight of the occupant.

In an embodiment of the system, the first data of the vehicle seat further comprises data related to the vehicle seat position.

In an embodiment of the system, the third data comprises at least one of a health and wellness data of the occupant comprising a heart rate, a blood pressure, a skin color, conscious state of the occupant and temperature of the occupant.

In an embodiment of the system, the secure data message generated using the protocol comprises: a vehicle information, a location of the vehicle, an information related to occupant, a health parameter, a seating detail of the occupant, a pre-health condition detail of the occupant, an allergy detail of the occupant, an emergency contact detail, other occupants of the vehicle, and the type of medical emergency detected.

Figure 2B:
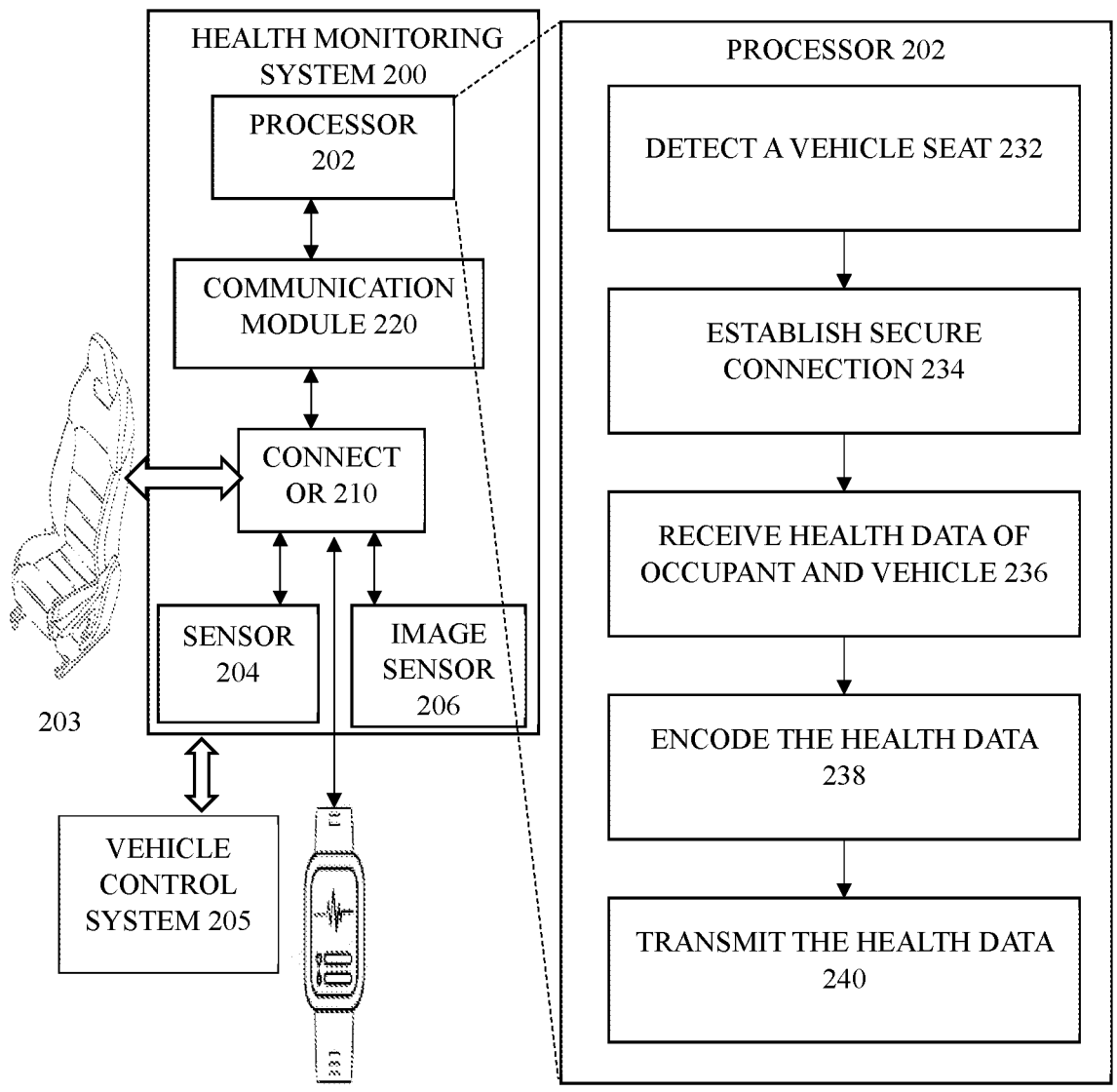
FIG. 2B shows a block diagram for a system to monitor health data in another embodiment.

FIG. 2B shows a block diagram for a system to monitor health data with a wearable device, in an embodiment. The system comprises a sensor 204, an image sensor 206, a wearable device 208 and a processor 202. The processor 202 receives data of vehicle seat 203 and health of an occupant from the image sensor 206 and the sensor 204 and the wearable device through the connector 210. The system to monitor health data communicates with the vehicle seat and the vehicle control system 205 through the communication module 220 via the connector 210.

According to another aspect, a system to monitor health data of vehicle occupants includes one or more wearable devices each associated with one or more vehicle occupants and a vehicle including one or more vehicle systems, sensor 204 and a processor 202, the processor 202 operably connected for computer communication to the one or more wearable devices. The system includes a data collecting module where the processor 202 receives health and wellness data in the form of physiological data associated with the one or more vehicle occupants from at least one of the wearable devices and the sensor 204. The system includes a trigger event module for when the processor 202 detects a trigger event based on at least one of the health and wellness data and vehicle data. The vehicle data is received from the one or more vehicle control system of the vehicle. The system includes a vehicle control module of the processor 202 that controls one or more vehicle systems of the vehicle to provide an indication of the health state according to the priority level and a location of the one or more vehicle occupants.

As mentioned above, and as shown in FIG. 2B, the system includes one or more wearable devices 208, each associated with one or more vehicle occupants. The system also includes a vehicle seat with sensor 204. The vehicle also includes the processor 202. The data collecting module of the processor 202 receives physiological data associated with the one or more vehicle occupants from at least one of the wearable devices and the sensor 204.

Processor 202 is configured to perform:

The system detects a vehicle seat, at step 232. A start signal is sent from a vehicle control system to the vehicle seat. If the vehicle seat is connected to the vehicle control system through a connector, an acknowledgement is received from the vehicle seat.

Upon receiving the acknowledgement from the vehicle seat, a secure connection is established between the vehicle seat and the vehicle control system, at step 234.

The vehicle control system receives data of the vehicle seat and a health data of the occupant of the vehicle seat, at step 236. The first data comprises at least one of a first position of the vehicle seat, a second position of the occupant on the vehicle seat, a weight of the occupant, a height of the occupant, and a pressure on the seat belt. The second data comprises a first image of the vehicle seat's position, a second image of a second position of the occupant on the vehicle seat, and a third image of a size of the vehicle seat according to the height and weight of the occupant. The first data of the vehicle seat further comprises data related to the vehicle seat position and if the vehicle seat is secured in the right position. The system is configured to receive a third data from a wearable device. The third data comprises at least one of a health and wellness data of the occupant comprising a heart rate, a blood pressure, a skin color, conscious state of the occupant and temperature of the occupant.

The received data is then encoded by identifying protected health information for transmission of a secure data message using a protocol similar to the HL7 protocol, at step 238.

At step 240, the encoded message is then transmitted to various recipients such as a medical facility, a vehicle infotainment system, emergency contact and to nearby devices in case of a high urgency condition. In an embodiment, the transmission is in real time via the communication module to an application installed in a central server, thereon, the application is configured to receive the data from the central server.

Physiological data can include, but is not limited to, heart information, such as, heart rate, heart rate pattern, blood pressure, oxygen content, among others. Physiological data can also include brain information such as, electroencephalogram (EEG) measurements, functional near infrared spectroscopy (fNIRS), functional magnetic resonance imaging (fMRI), among others. Physiological data can also include digestion information, respiration rate information, salivation information, perspiration information, pupil dilation information, body temperature, muscle strain, as well as other kinds of information related to the autonomic nervous system or other biological systems of the vehicle occupant. In some embodiments, physiological data can also include behavioral data, for example, mouth movements, facial movements, facial recognition, head movements, body movements, hand postures, hand placement, body posture, gesture recognition, among others.

Health and wellness data can also include recognition data (e.g., biometric identification) used to identify the vehicle occupant. For example, recognition data can include a predetermined heart rate pattern associated with a vehicle occupant, eye scan data associated with a vehicle occupant, fingerprint data associated with a vehicle occupant, among other types of recognition data. It is appreciated that the recognition data and other types of physiological data can be stored at various locations (e.g., the disk, a memory integrated with the wearable devices, the medical database, the data collection module 106) and accessed by the processor 202.

The processor 202 can receive and/or access the health and wellness data from different sources. In one embodiment, the data collection module 106 receives the health and wellness data from at least one of the wearable devices 208 and the vehicle. For example, the wearable devices 208 can include sensors for sensing and determining various parameters of a user, for example, location, motion, and physiological parameters, among others. In one embodiment, the sensors include biosensors for sensing health and wellness data and other data associated with the body and biological systems of the vehicle occupant. Additionally, it is appreciated that some physiological data can be sensed and/or determined by the one or more wearable devices 208 using gesture tracking and/or recognition implemented by the wearable devices 208.

Further, the system may sense and determine health and wellness data of one or more vehicle occupants. For example, sensor 204 may include one or more bio-monitoring sensors, heart rate sensors, blood pressure sensors, oxygen content sensors, respiratory sensors, perspiration sensors, imaging sensors to sense eye movement, pupil dilation, gestures, as well as any other kinds of sensors for monitoring one or more vehicle occupants. It is understood that the sensors 204 of the system 200 are disposed in any location of a vehicle connected to the vehicle control system through a wired connector or a wireless connector. For example, sensors can be disposed in a steering wheel, seat, armrest, or other component to detect physiological data associated with the one or more vehicle occupants.

It is understood that physiological data can be obtained from both the wearable devices 208 and the sensor 204. Further, the physiological data from both the wearable devices 208 and/or the sensor 204 be received in real time or stored in the data collection module 106 and aggregated at the processor 202, and/or a central server accessed through the network through the communication module, for example, the medical database. It is understood that the wearable devices 208 and/or the sensor 204 can obtain other types of data associated with the user by accessing local or remotely stored data or data through a network connection.

For example, the wearable devices 208 may include data on other inputs a vehicle occupant encounters on a daily basis.

The system 200 may include security features. The security features can include data encryption using any of a variety of security protocols, e.g., Hypertext Transfer Protocol HTTPS (HTTP secure), etc., and/or can include user authentication. User authentication can allow aspects of the system 200 to be available to a particular user based on the identity of the user and/or the location from which the user is accessing the system. To that end, each user can have a unique username, password, and/or other security credentials to facilitate access to the system 200. The received security parameter information can be checked against a database of authorized users to determine whether the user is authorized and to what extent the user is permitted to interact with the system, view information stored in the system, and so forth. Exemplary examples of parties who can be permitted to access the system 200 include occupants, potential occupants, significant others of occupants or potential occupants, friends of occupants or potential occupants, family members of occupants or potential occupants, doctors, nurses, medical assistants, insurers, home care staff, and hospital administrators.

Figure 3A:
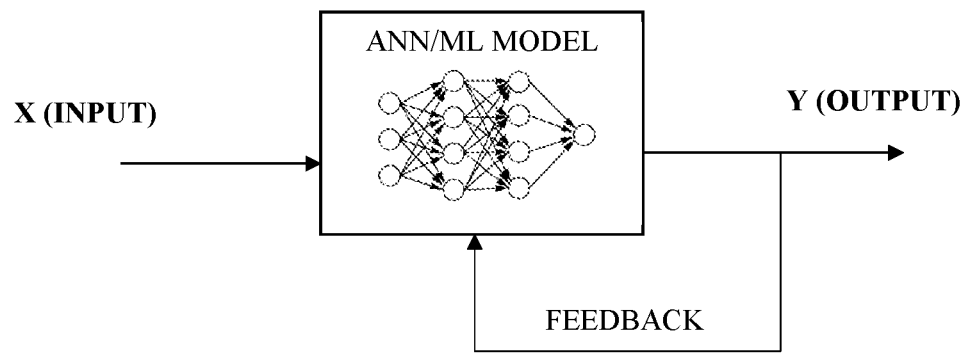
FIG. 3A shows a structure of the neural network/machine learning model with a feedback loop.

FIG. 3A shows a structure of the neural network/machine learning model with a feedback loop. Artificial neural networks (ANNs) model comprises an input layer, one or more hidden layers, and an output layer. Each node, or artificial neuron, connects to another and has an associated weight and threshold. If the output of any individual node is above the specified threshold value, that node is activated, sending data to the next layer of the network. Otherwise, no data is passed to the next layer of the network. A machine learning model or an ANN model may be trained on a set of data to take a request in the form of input data, make a prediction on that input data, and then provide a response. The model may learn from the data. Learning can be supervised learning and/or unsupervised learning and may be based on different scenarios and with different datasets. Supervised learning comprises logic using at least one of a decision tree, logistic regression, support vector machines. Unsupervised learning comprises logic using at least one of a k-means clustering, a hierarchical clustering, a hidden Markov model, and an apriori algorithm. The output layer may predict or detect a health issue and the severity of the health issue based on the input data.

In an embodiment, ANN's may be a Deep-Neural Network (DNN), which is a multilayer tandem neural network comprising Artificial Neural Networks (ANN), Convolution Neural Networks (CNN) and Recurrent Neural Networks (RNN) that can recognize features from inputs, do an expert review, and perform actions that require predictions, creative thinking, and analytics. In an embodiment, ANNs may be Recurrent Neural Network (RNN), which is a type of Artificial Neural Networks (ANN), which uses sequential data or time series data. Deep learning algorithms are commonly used for ordinal or temporal problems, such as language translation, Natural Language Processing (NLP), speech recognition, and image recognition, etc. Like feedforward and convolutional neural networks (CNNs), recurrent neural networks utilize training data to learn. They are distinguished by their "memory" as they take information from prior input via a feedback loop to influence the current input and output. An output from the output layer in a neural network model is fed back to the model through the feedback. The variations of weights in the hidden layer(s) will be adjusted to fit the expected outputs better while training the model. This will allow the model to provide results with far fewer mistakes.

The neural network is featured with the feedback loop to adjust the system output dynamically as it learns from the new data. In machine learning, backpropagation and feedback loops are used to train an AI model and continuously improve it upon usage. As the incoming data that the model receives increases, there are more opportunities for the model to learn from the data. The feedback loops, or backpropagation algorithms, identify inconsistencies and feed the corrected information back into the model as an input.

Even though the AI/ML model is trained well, with large sets of labeled data and concepts, after a while, the models' performance may decline while adding new, unlabeled input due to many reasons which include, but not limited to, concept drift, recall precision degradation due to drifting away from true positives, and data drift over time. A feedback loop to the model keeps the AI results accurate and ensures that the model maintains its performance and improvement, even when new unlabeled data is assimilated. A feedback loop refers to the process by which an AI model's predicted output is reused to train new versions of the model.

Initially, when the AI/ML model is trained, a few labeled samples comprising both positive and negative examples of the concepts (for e.g., health issues) are used that are meant for the model to learn. Afterward, the model is tested using unlabeled data. By using, for example, deep learning and neural networks, the model can then make predictions on whether the desired concept/s (for e.g., detection of a health issue) are in unlabeled images. Each image is given a probability score where higher scores represent a higher level of confidence in the models' predictions. Where a model gives an image a high probability score, it is auto labeled with the predicted concept. However, in the cases where the model returns a low probability score, this input may be sent to a controller (may be a human moderator) which verifies and, as necessary, corrects the result. The human moderator may be used only in exception cases. The feedback loop feeds labeled data, auto-labeled or controller-verified, back to the model dynamically and is used as training data so that the system can improve its predictions in real-time and dynamically.

Figure 3B:
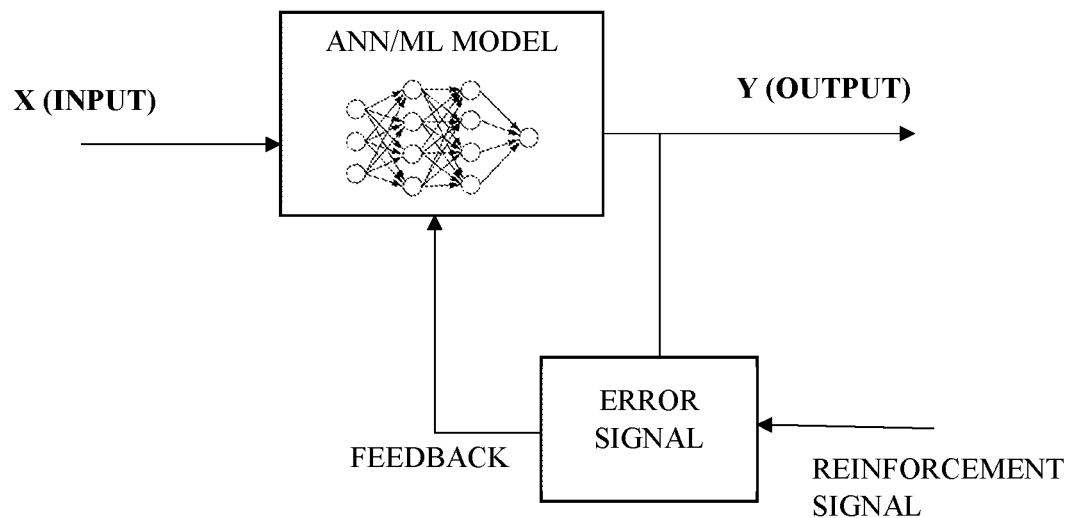
FIG. 3B shows a structure of the neural network/machine learning model with reinforcement learning.

FIG. 3B shows a structure of the neural network/machine learning model with reinforcement learning. The network receives feedback from authorized networked environments. Though the system is similar to supervised learning, the feedback obtained in this case is evaluative not instructive, which means there is no teacher as in supervised learning. After receiving the feedback, the network performs adjustments of the weights to get better predictions in the future. Machine learning techniques, like deep learning, allow models to take labeled training data and learn to recognize those concepts in subsequent data and images. The model may be fed with new data for testing, hence by feeding the model with data it has already predicted over, the training gets reinforced. If the machine learning model has a feedback loop, the learning is further reinforced with a reward for each true positive of the output of the system. Feedback loops ensure that AI results do not stagnate. By incorporating a feedback loop, the model output keeps improving dynamically and over usage/time.

Figure 3C:
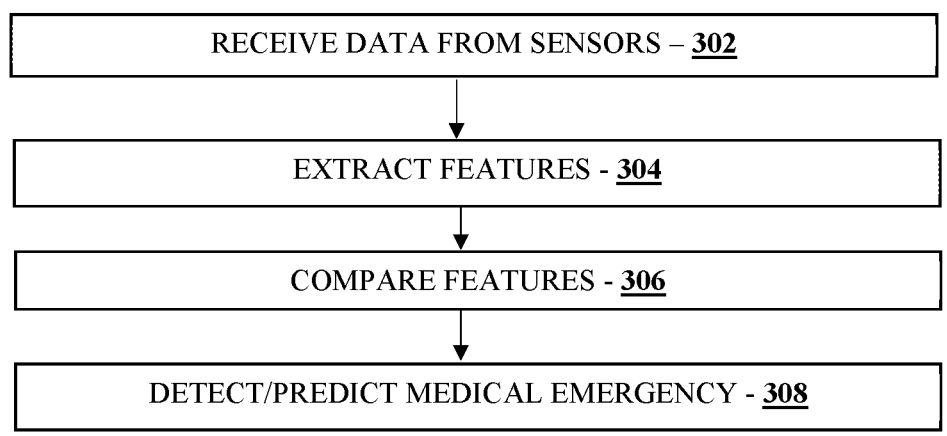
FIG. 3C shows a flowchart for detecting or predicting medical emergency from the sensor data according to an embodiment.

FIG. 3C shows a flowchart for detecting or predicting medical emergency from the sensor data according to an embodiment. According to an embodiment, the emergency detection module comprises the components of an apparatus and the system to detect health and wellness data of the occupant. The components may each be adapted to measure, track, and/or monitor the occupant by using one or more of the sensors 302 which may comprise camera, microphone, pressure sensors, occupancy sensors, health sensors such as heart rate sensor, blood pressure (BP) sensor, temperature sensor, etc. The data may come from other sources such as a mobile device, a health or fitness tracker, etc. In some embodiments, the system may extract features from the data using machine learning or artificial intelligence algorithm, such features for example may include, but are not limited to, facial expression, body posture, a voice print, body position and/or motion, vitals—heart rate, respiration rate, body temperature, blood pressure, perspiration, skin color, lip color, comfort level, in-vehicle noises, occupant noises, seat occupancy, grip pressure, allergic reaction, etc. as shown at step 304. Occupant noises may include a noise made prior to, during, or after the emergency event. A seat occupancy may determine where the occupant is seated, whether the occupant is a child and whether the child is in a child car seat, etc., and a grip pressure may be measured by the force sensors in the car seat, the armrests, or in the belts of the car seat. The processor 202 may be enabled to extract a height of the occupant based on the height his head reaches on the seat, the leg resting position, and a posture from the camera. Facial features include eye, mouth, lips, facial muscle, skin, shape of the face, etc. Once the features are extracted using image processing algorithms and artificial intelligence, the system uses a pre-trained artificial intelligence/machine learning (AI/ML) model to compare the features at step 306. The system, based on the match of features, may predict, or detect an emergency 308. In an embodiment, the system can predict or detect health emergency related to, for example, choking, breathing issue, fever, stroke, heart attack, asthma, seizure, epilepsy, diarrhea, cough, rash, vomiting, loss of consciousness, colic, nosebleed, bleeding, neurological disorder, etc. Example: When a child is experiencing a seizure, some of the symptoms could be body spasms and shaking (a "fit"), loss of awareness or unusual sensations, stiffness or twitching of part of the body, such as an arm or hand, smacking lips, rubbing hands, making random noises, moving arms around, picking at clothes or fiddling with objects, chewing, swallowing, staring blankly into space. By combining the image classification and features recognition algorithm, the health emergency can be predicted as a possible seizure. In an embodiment, the system is designed to achieve artificial intelligence (AI) via a model based on predetermined rules, also referred to as rule-based AI system. For example, if the face is drooping (identify from image sensor), arm is numb/weak (identify from image or arm pressure via pressure sensor), speech is slurred (identify via a microphone recording) then provide an emergency alert and indicate that the emergency alert is for a possible stroke, with a severity score or scale of 10.

The vehicle control system may also communicate with one or more sensors 302, which are either associated with the vehicle seat or communicate with the vehicle seat. Vehicle sensors 302 may include one or more sensors for providing information to the vehicle control system that determine or provide information about the environment in which the vehicle is operating. Embodiments of these sensors may be as described in conjunction with FIG. 3C. non-vehicle sensors may be any type of sensor that isn't currently associated with the vehicle. For example, non-vehicle sensors can be sensors in a traffic system operated by a third party that provides data to the health monitoring system. Further, the non-vehicle sensor can be other types of sensors which provide information about the distant environment or other information about the vehicle or the environment. These non-vehicle sensors may be operated by third parties but provide information to the health monitoring system. Examples of information that may be used by the health monitoring system may include weather tracking data, user health tracking data, vehicle maintenance data, or other types of data, which may provide environmental or other data to the health monitoring system.

In an embodiment, FIG. 3C shows a set of sensors or vehicle sensor 302 associated with the vehicle. The vehicle includes, among many other components common to vehicles, wheels, a power source (such as an engine, motor, or energy storage system (e.g., battery or capacitive energy storage system)), a manual or automatic transmission, a manual or automatic transmission gear controller, a power controller (such as a throttle), a vehicle control system, the display device, a braking system, a steering wheel, a power source activation/deactivation switch (e.g., an ignition), an occupant seating system, a wireless signal receiver to receive wireless signals from signal sources such as roadside beacons and other electronic roadside devices, and a satellite positioning system receiver (e.g., a Global Positioning System ("GPS") (US), GLONASS (Russia), Galileo positioning system (EU), Compass navigation system (China), and Regional Navigational Satellite System (India) receiver).

The vehicle includes a number of sensors in wireless or wired communication with the vehicle control system and/or display device to collect sensed information regarding the vehicle state, configuration, and/or operation. Exemplary sensors include wheel state sensor to sense one or more of vehicle speed, acceleration, deceleration, wheel rotation, wheel speed (e.g., wheel revolutions-per-minute), wheel slip, and the like, a power source energy output sensor to sense a power output of the power source by measuring one or more of current engine speed (e.g., revolutions-per-minute), energy input and/or output (e.g., voltage, current, fuel consumption, and torque) (e.g., turbine speed sensor, input speed sensor, crankshaft position sensor, manifold absolute pressure sensor, mass flow sensor, and the like), and the like, a switch state sensor to determine a current activation or deactivation state of the power source activation/deactivation switch, a transmission setting sensor to determine a current setting of the transmission (e.g., gear selection or setting), a gear controller sensor to determine a current setting of the gear controller, a power controller sensor to determine a current setting of the power controller, a brake sensor to determine a current state (braking or non-braking) of the braking system, a seating system sensor to determine a seat setting and current weight of seated occupant, if any, in a selected seat of the seating system, exterior and interior sound receivers (e.g., a microphone and other type of acoustic-to-electric transducer or sensor) to receive and convert sound waves into an equivalent analog or digital signal. Examples of other sensors (not shown) that may be employed include safety system state sensors to determine a current state of a health monitoring system (e.g., air bag setting (deployed or undeployed) and/or seat belt setting (engaged or not engaged)), light setting sensor (e.g., current headlight, emergency light, brake light, parking light, fog light, interior or passenger compartment light, and/or tail light state (on or off)), brake control (e.g., pedal) setting sensor, accelerator pedal setting or angle sensor, clutch pedal setting sensor, emergency brake pedal setting sensor, door setting (e.g., open, closed, locked or unlocked)

sensor, engine temperature sensor, passenger compartment or cabin temperature sensor, window setting (open or closed) sensor, one or more cameras or other imaging sensors (which commonly convert an optical image into an electronic signal but may include other devices for detection objects such as an electromagnetic radiation emitter/receiver that emits electromagnetic radiation and receives electromagnetic waves reflected by the object) to sense objects, such as other vehicles and pedestrians and optionally determine the distance, trajectory and speed of such objects, in the vicinity or path of the vehicle, odometer reading sensor, trip mileage reading sensor, wind speed sensor, radar transmitter/receiver output, brake wear sensor, steering/torque sensor, oxygen sensor, ambient lighting sensor, vision system sensor, ranging sensor, parking sensor, heating, venting, and air conditioning (HVAC) sensor, water sensor, air-fuel ratio meter, blind spot monitor, hall effect sensor, microphone, radio frequency (RF) sensor, infrared (IR) sensor, vehicle control system sensors, wireless network sensor (e.g., Wi-Fi and/or BLUETOOTH™ sensor), cellular data sensor, and other sensors known to those of skill in the vehicle art.

In the depicted vehicle embodiment, the various sensors are in communication with the display device and vehicle control system via signal carrier network. As noted, the signal carrier network can be a network of signal conductors, a wireless network (e.g., a radio frequency, microwave, or infrared communication system using a communications protocol, such as Wi-Fi), or a combination thereof.

Other sensors may be included and positioned in the interior space of the vehicle. Generally, these interior sensors obtain data about the health of the driver and/or passenger(s), data about the safety of the driver and/or passenger(s), and/or data about the comfort of the driver and/or passenger(s). The health data sensors can include sensors in the steering wheel that can measure various health telemetry for the person (e.g., heart rate, temperature, blood pressure, blood presence, blood composition, etc.). Sensors in the seats may also provide for health telemetry (e.g., presence of liquid, weight, weight shifts, etc.). Infrared sensors could detect a person's temperature; optical sensors can determine a person's position and whether the person has become unconscious. Other health sensors are possible and included herein.

Safety sensors can measure whether the person is acting safely. Optical sensors can determine a person's position and focus. If the person stops looking at the road ahead, the optical sensor can detect the lack of focus. Sensors in the seats may detect if a person is leaning forward or may be injured by a seat belt in a collision. Other sensors can detect that the driver has at least one hand on a steering wheel. Other safety sensors are possible and contemplated as if included herein.

Comfort sensors can collect information about a person's comfort. Temperature sensors may detect a temperature of the interior cabin. Moisture sensors can determine relative humidity of the interior cabin. Audio sensors can detect loud sounds or other distractions of the interior cabin and from devices (connected to earplugs). Audio sensors may also receive input from a person through voice data. Other comfort sensors are possible and contemplated as if included herein.

In an embodiment of the system, the secure data message generated using the protocol comprises: a vehicle information, a location of the vehicle, an information related to an occupant, a health parameter, a seating detail of the occupant, a pre-health condition detail of the occupant, an allergy detail of the occupant, an emergency contact detail, other occupants of the vehicle, and the type of medical emergency detected.

In an embodiment of the system, the system is not tied to a particular data format or communication protocol, enabling the system to be customized to the data formats and network protocols of an installation. The system comprises a data format and communication protocol translator module as a part of the data encoding module to convert data files and communications protocols to a common format and protocol. The protocol is one of a hospital transmission protocol, related patient monitoring protocol, and a standard HIT protocol based on the Health Level 7 (HL7) standard.

An embodiment relates to a method comprising detecting a vehicle seat in the vehicle; establishing a secured connection with the vehicle seat through the connector; receive a first data from the sensor and a second data from the image sensor through the connector, the first data and the second data being indicative of information gathered regarding at least one parameter related to at least one of a condition of the vehicle seat, a health and wellness of an occupant of the vehicle, and the connector being configured to facilitate gathering of the information; encoding the first data and the second data by identifying protected health information for transmission of a secure data message using a protocol; and transmitting the first data and the second data in real time via the communication module to an application installed in a central server, thereon, the application being configured to facilitate receipt of the data from the central server.

An embodiment relates to a non-transitory computer storage medium storing a sequence of instructions, which when executed by a processor, causes detecting a vehicle seat in the vehicle; establishing a secured connection with the vehicle seat through the connector, receive a first data from the sensor and a second data from the image sensor through the connector, the first data and the second data being indicative of information gathered regarding at least one parameter related to at least one of a condition of the vehicle seat, a health and wellness of an occupant of the vehicle, and the connector being configured to facilitate gathering of the information; encoding the first data and the second data by identifying protected health information for transmission of a secure data message using a protocol; and transmitting the first data and the second data in real time via the communication module to an application installed in a central server thereon, the application being configured to facilitate receipt of the data from the central server.

In an embodiment of the system, the transmission to the application occurs automatically in response to the receipt of the first data and the second data at the central server. An embodiment relates to a method comprising detecting a vehicle seat in the vehicle; establishing a secured connection with the vehicle seat through the connector; receive a first data from the sensor, a second data from the image sensor and a third data from a wearable device through the connector, the first data, the second data and the third data being indicative of information gathered regarding at least one parameter related to at least one of a condition of the vehicle seat, a health and wellness of a patient, and the connector being configured to facilitate gathering of the information; encoding the first data, the second data and the third data by identifying protected health information for transmission of a secure data message using a protocol; and transmitting the received the first data, second data and the third data in real time via communication module to an application installed in a central server, thereon, the application being configured to facilitate receipt of the data from the central server.

An embodiment relates to non-transitory computer storage medium storing a sequence of instructions, which when executed by a processor, causes detecting a vehicle seat in the vehicle; establishing a secure connection with the vehicle seat through the connector; receive a first data from the sensor, a second data from the image sensor and a third data from a wearable device through the connector, the first data, the second data and the third data being indicative of information gathered regarding at least one parameter related to at least one of a condition of the vehicle seat, a health and wellness of a patient, and the connector being configured to facilitate gathering of the information; encoding the first data, the second data and the third data by identifying protected health information for transmission of a secure data message using a protocol; and transmitting the received first data, second data and the third data in real time via a communication module to an application installed in a central server, thereon, the application being configured to facilitate receipt of the data from the central server.

The transmission to the application occurs in response to a request received at the central server from the application requesting data gathered by at least one sensor.

Once the data related to the vehicle and the data related to the health and wellness of the occupant is gathered by the sensor, the sensors transmit the data to the processor. The processor then is further configured to identify the data and encode the data in an encoded format using a protocol. The data is identified using protected health information protocol of Health Insurance Portability and Accountability Act (HIPAA). In the United States of America (USA), protected health information is considered to be individually identifiable information relating to the past, present, or future health status of an individual that is created, collected, or transmitted, or maintained by a HIPAA-covered entity in relation to the provision of healthcare, payment for healthcare services, or use in healthcare operations (PHI healthcare business uses).

Health information such as diagnoses, treatment information, medical test results, and prescription information are considered protected health information under HIPAA, as are national identification numbers and demographic information such as birth dates, gender, ethnicity, and contact and emergency contact information. Protected Health Information (PHI) relates to physical records, while ePHI is any PHI that is created, stored, transmitted, or received electronically.

PHI is any health information that can be tied to an individual which, under HIPAA means protected health information, includes one or more of the following 18 identifiers. If these identifiers are removed, the information is considered de-identified protected health information, which is not subject to the restrictions of the HIPAA Privacy Rule. Protected health information may comprise data having 1. Names (Full or last name and initial), 2. all geographical identifiers smaller than a state except for the initial three digits of a zip code if, according to the current publicly available data from the U.S. Bureau of the Census: the geographic unit formed by combining all zip codes with the same three initial digits contains more than 20,000 people; and the initial three digits of a zip code for all such geographic units containing 20,000 or fewer people is changed to 000, 3. dates (other than year) directly related to an individual, 4. phone numbers, 5. fax numbers, 6. email addresses, 7. social security numbers, 8. medical record numbers, 9. health insurance beneficiary numbers, 10. account numbers, 11. Certificate numbers, 12. license numbers, 13. vehicle identifiers (including serial numbers and license plate numbers), 14. device identifiers, 15. device serial numbers, 16. web uniform resource locators (URLs), 17. Internet Protocol (IP) address numbers, 18. biometric identifiers, including finger, retinal and voice prints, full face photographic images and any comparable images, any other unique identifying number, characteristic, or code except the unique code assigned by the investigator to code the data.

Multiple variants of data format may be expected from multiple devices, including sensors, image sensors and wearable devices. To address this challenge, the system may be customized upon installation to use the communication links that work with the particular devices installed in the hospital network. The various embodiments are not tied to a particular data format or communication protocol, enabling the processor to be customized to the data formats and network protocols of the installation. Alternatively, a data format and communication protocol translator module or server may be included within the system to convert data files and communications protocols to a common format and protocol.

Further, the processor processes the identified protected health information and the other data into the data encoding module. The data encoding module encodes the data into a particular protocol that can be transmitted to emergency medical facilities, emergency contacts and can be displayed on vehicle infotainment systems. The protocol used is a simple readable protocol that is understandable to any individual seeing the message.

One of the examples of the encoded formats is Health Level 7 (HL7) protocol. Health Level Seven or HL7 refers to a set of international standards for transfer of clinical and administrative data between software applications used by various healthcare providers. These standards focus on the application layer, which is "layer 7" in the OSI model. The HL7 standards are produced by Health Level Seven International, an international standards organization, and are adopted by other standards issuing bodies such as American National Standards Institute and International Organization for Standardization.

Hospitals and other healthcare provider organizations typically have many different computer systems used for everything from billing records to occupant tracking. All of these systems should communicate with each other (or "interface") when they receive new information, or when they wish to retrieve information, but not all do so.

HL7 International specifies a number of flexible standards, guidelines, and methodologies by which various healthcare systems can communicate with each other. Such guidelines or data standards are a set of rules that allow information to be shared and processed in a uniform and consistent manner. These data standards are meant to allow healthcare organizations to easily share clinical information. Theoretically, this ability to exchange information should help to minimize the tendency for medical care to be geographically isolated and highly variable. Encoding characters are special characters used to construct an HL7 message, defining how data is separated in an HL7 message. Below are the encoding characters: Field Separator (normally 1), Component Separator (normally ^), Subcomponent Separator (normally &), Field Repeat Separator (normally ~), Escape Character (normally \).

Encoding characters are defined dynamically in the MSH segment. The character immediately following the segment "MSH" is the first encoding character, which is the field separator. The rest of the encoding characters are defined in MSH-2, where the four characters in this field define the component separator, repetition separator, escape character, and subcomponent separator in that respective order.

In an HL7 message, sometimes the actual data in a field may contain an encoding character, which will require some data manipulation for the message to be sent correctly. For example, keep in mind that the escape character for the subcomponent separator is "&," data in a message may contain the following: "Occupant must rest & ice the knee." In this case, a system may treat the field in which this data is located as two subcomponents, although it really should be treated as a single field because the "&" is meant to mean "and" and not a subcomponent separator. HL7 Version 2 supports two forms of message encoding, a custom delimiter-based encoding, and an XML encoding. HL7 chose the original delimiter-based encoding to reduce the size of messages as much as possible. For example, if you compare a data structure in which delimiters separate elements to a structure that positions each element in a fixed set of positions, the delimiter-based structure is far more economical if a) messages do not contain some elements, and b) some elements do not fill all the space allowed. The only overhead in delimiter-based structures is the delimiters themselves.

HL7 messages are used to transfer electronic data between disparate healthcare systems, each sending information about a particular event such as an occupant admission. HL7 messages are in human-readable (ASCII) format, though they may require some effort to interpret. This section describes the contents of an HL7 message and how an HL7 message is organized. An HL7 message consists of one or more segments. Each segment is displayed on a different line of text. A carriage return character (\r, which is 0D in hexadecimal) separates one segment from another. Each segment consists of one or more composites, also known as fields. A pipe (|) character is used to separate one composite from another. If a composite contains other composites, these sub-composites (or sub-fields) are normally separated by caret (^) characters. For example, the occupant information to be encoded may be displayed as "OCP-INF" as the header for the occupant information. The header is then separated by a pipe (|) followed by the information as JOHN^DOE|AGE|WEIGHT|GENDER-|HEIGHT|ADDRESS. Here, each of the segment is separated by a pipe (|), and parts within the segment are separated by caret (^) such as JOHN^DOE. Here JOHN^DOE is the name of the occupant. The occupant information is displayed as OCP-INF|JOHN^DOE|AGE|WEIGHT-|GENDER|HEIGHT|ADDRESS.

For example, as shown in FIG. 4, each of the data received is given a header that has six characters separated by a dash (-) such as "XXX-YYY," for example occupant information is encoded as "OCP-INF". Vehicle location may have the header as "VEH-LOC," vehicle details may have the header as "VEH-DTL," event type/emergency type may have the header "EMG-TYP," health parameters may have the header as "HLT-PMT," occupant seating details may have the header as "OCP-SDT," occupant pre-health condition details may have the header as "OCP-PHC," occupant allergy details may have the header as "OCP-ALD," emergency contact details may have the header as "EMG-CNT," other occupants of the vehicle may have the header as "OTR-DTL". Here, each of the segments is separated by a pipe (|), and parts within the segment are separated by a caret (^), such as JOHN^DOE. Here JOHN^DOE is the name of the occupant. The occupant information is displayed as OCP-INF|JOHN^DOE|AGE|WEIGHT|GENDER|HEIGHT|ADDRESS.

Another example of medical data encoding and transmission protocol is CEN ISO/IEEE 11073* International organization for standardization which enables the communication between medical devices and external information systems. This standard provides plug-and-play interoperability between devices and facilitates the efficient exchange of data acquired at the point of care in all care environments. Institute of Electrical and Electronics Engineers IEEE 802.11 a/b/g/n are standards for implementing a wireless local area network (WLAN) in 2.4 GHz and 5 GHz frequency bands, utilizing the same basic protocol.

Another example for a medical transfer protocol is CEN/TC 251. The CEN Technical Committee 251, within the European Committee for Standardization (CEN), is a technical decision-making body in the field of Health Information and Communications Technology (ICT) in the European Union. The goal is to achieve compatibility and interoperability between independent systems and to enable modularity in Electronic Health Record systems.

Workgroups establish requirements for structured health information in order to support clinical and administrative procedures with technical methods to support interoperable systems. In addition, they establish requirements regarding safety, security, and quality. Yet another example is Integrating the Healthcare Enterprise (IHE). Integrating the Healthcare Enterprise IHE is an initiative by healthcare professionals and industry to improve the way computer systems in healthcare share information. IHE promotes the coordinated use of established standards such as Digital Imaging and Communications in Medicine (DICOM) and HL7 to address specific clinical needs in support of optimal occupant care. Systems developed in accordance with IHE communicate with one another better, are easier to implement, and enable care providers to use information more effectively.

For still another example, the system can include causing the central server to request an aggregated occupant data record and to combine the requested aggregated occupant data record, with identifying PHI information, for transmission of a secure data message using the HL7 protocol to an electronic medical record (EMR) system, on behalf of the occupant. The aggregated occupant data record can be requested in real time by an explicit electronic data request, in the form of an HL7 message, received by the server from the EMR system. The combining can be triggered automatically as a periodic update as part of an electronic order, received as an HL7 message from the EMR system, and can be scheduled by the central server as a function of a care path directive of the occupant.

Figure 5:
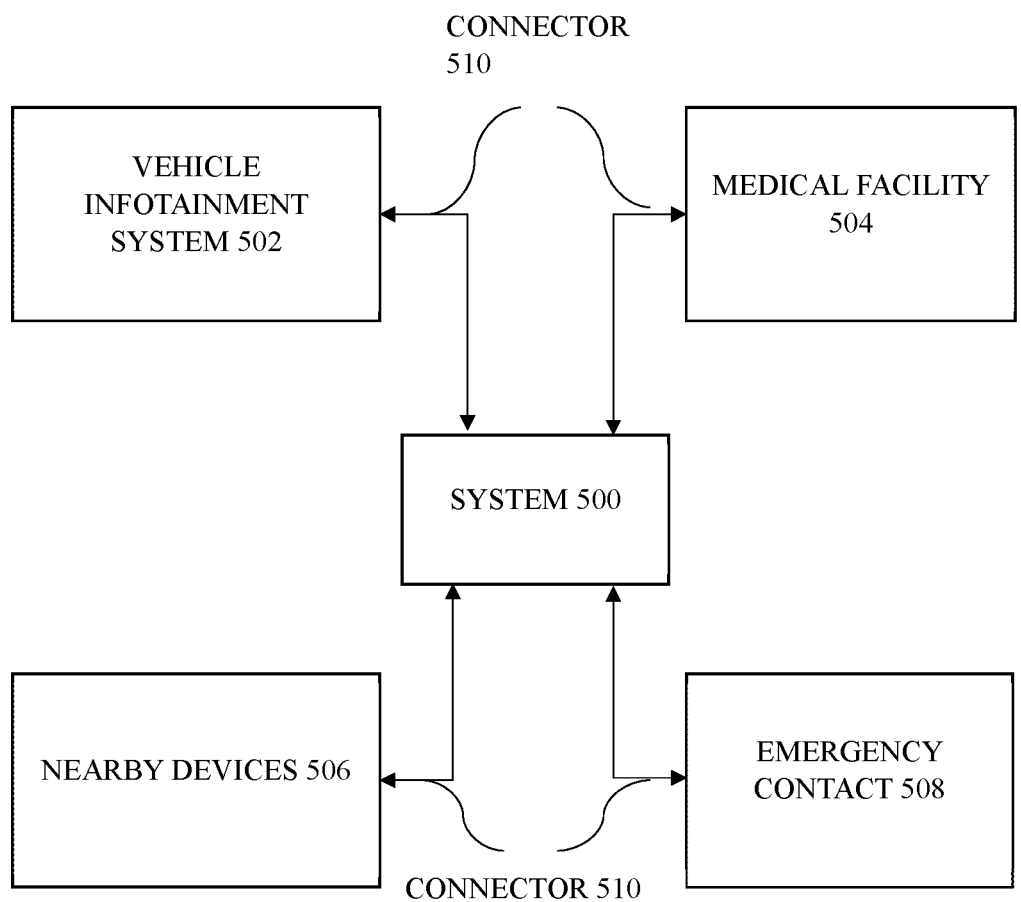
FIG. 5 shows the network of the system communicating to various devices or facilities in one embodiment.

FIG. 5 shows the transmission of the encoded data to various devices from the system 500. FIG. 5 shows transmission of data to the vehicle infotainment system 502, medical facility 504, nearby devices 506 and emergency contacts 508. A connector 510 transmits the data through a secure computer server platform (server) from the system 500. The server may provide storage of received data in a file or database and can use protocols such as HTTP and HTTPS to communicate with the devices having vehicle infotainment system 502, medical facility 504, nearby devices 506 and emergency contacts 508. The Server can implement a data retrieval system using, for example, web based protocols such as HTTP and HTTPS to implement a display system or a statistical analysis system of data received. The Server may comprise a processor such as an Intel or Advanced Micro Devices, Inc. (AMD) processor that executes x86 instructions or an Oracle processor that executes Scalable Processor Architecture (SPARC) instructions, a computer bus that enables the processor to communicate with other components of the Server, where such communication may include communications across a network or communications channel such as a parallel or serial communication channel used to communicate with disk drives (using for example a serial advanced technology attachment (SATA) or Small Computer System Interface (SCSI) channel, or a virtualized communication channel such as iSCSI across a communication network), or a keyboard (using for example a PS/2 or USB communication channel), or display (using for example a Video Graphics Array (VGA), Digital Visual Interface (DVI), or High-Definition Multimedia Interface (HDMI) communication channel), or memory to store a program that directs the execution of the Server and stores data received from or transmitted to another device, a network interface or other communications interface that enables communication with another device such as one or more mobile devices, wearable devices, or wireless or wired access devices or other servers or computers used either for the same or similar purposes as disclosed herein. The health monitoring system may be used for different purposes such as within a clinic or hospital setting for individuals with disease records, to support medical procedures or treatments, or by occupant medical treatment records, or by an association formed for the benefit of either individuals diagnosed with a disease, medical or clinical practitioners or staff, or by one or more researchers, enabling the exchange of information between the Server and other servers or computers to support collaborative activities, a storage device such as a hard disk drive (HDD), a solid state disk drive, or a memory card such as a Secure Digital (SD) card, or a network-accessible storage device (NAS) or other storage device that is used for long-term or persistent storage of the program and data, and an interface to allow administration of the Server by another computer or a human operator, the interface being either at least a keyboard and display device, and optionally a pointing device such as a mouse or a touch pad, or a virtual interface such as a Lights Out Manager or an implementation of the Virtual Network Computing (VNC) or other remote desktop protocol that emulates at least a keyboard and display device using another device such as a second computer that can communicate with the Server using a network. If the server uses a database to store data rather than files stored within its filesystem, a database software such as My Structured Query Language MySQL or Oracle may be used and included in the Server. Communication protocols such as HTTP, HTTPS, or other protocols using XML, can be implemented using web server and/or business-to-business communications software such as Apache, Tomcat, Jakarta EE (J2EE), or Java Beans. The combination of the Server and the one or more mobile devices, wearable devices, or wireless or wired access devices enable the monitored or unmonitored measurements in either the home or a clinical environment.

In an embodiment, the encoded message may be transmitted to an ambulance, a home, a hospital, a hospice, a nursing home, a testing center, an emergency response location (e.g., an emergency room or an intensive cardiac care unit), an outlying medical office, a secondary care center, a senior care center, a physical therapy center, or another facility where occupant data is to be received or captured. For example, the data transmission module may exchange data and commands with the devices using wireless data links transmitted via Internet protocols over a cellular network.

In an embodiment, the system may transmit the occupant's medical data, including vital data and any other medical data regarding the occupant, to a messaging server. In an embodiment, the computing device may transmit the medical data over a wireless network, such as a cellular data network or a Wi-Fi local area network. In an embodiment, the messaging server may exchange information with the computing device using Internet protocols or by using other texting formats (e.g., Short Message Services (SMS) messaging). In an embodiment, the system may utilize encryption techniques during transmission of the occupant's medical and testing data. In another embodiment, the computing device may simultaneously or exclusively transmit the occupant's medical data to a hospital data server, a web server, and/or any other server used for delivering occupant medical data.

In an embodiment, the system may utilize a communication protocol which provides guidelines for scheduling transmissions of a particular urgency level. For example, the protocol may direct the system to initiate SMS message transmissions through a communication server within a few minutes of detecting a low level urgency condition. The protocol may have different time constraints based on the urgency level. For example, a higher level urgency condition may require repeat transmissions every several minutes until a choking condition ceases to exist or until help or assistance is received.

In an embodiment, the protocol also may define the device to which the message is transmitted. For example, in low emergency conditions or no emergency conditions, the message is transmitted only to the vehicle infotainment system 502 where the message is displayed on the display of the vehicle infotainment system 502. In high emergency conditions such as choking, or unconsciousness of the occupant, the system may transmit the message to every device that is the vehicle infotainment system 502, medical facility 504, nearby devices 506, and emergency contacts 508. Here the message is transmitted to nearby devices and vehicles too, so in case a nearby vehicle is willing to help, the nearby vehicle or occupant may communicate with, and may help, the particular vehicle experiencing a medical emergency.

In an embodiment, the protocol contains response time constraints (i.e., expected response times). For example, the protocol may require a medical facility 504 to respond to high level urgency transmissions within a particular amount of time. If responses are not received according to protocol time constraints, the system may define further actions and/or transmissions that may escalate the urgency level. For example, if the communications server does not receive a response transmission from a medium level urgency communication within a certain time period, the system may increase the urgency level (i.e., the medium level may become a high level urgency) and perform actions appropriate for the increased urgency level. The protocol may also define rules for scheduling subsequent transmissions to alternative recipients. For example, the protocol may instruct the system to send a to a second medical facility 504 if a first medical facility 504 does not respond to a transmission.

In an embodiment, the system may define the role of various recipients based on the characteristics of the occupant's medical condition (e.g., unconsciousness condition). The system may use the defined roles to schedule transmissions, and to generate the content of alerts or instructions within transmissions. For example, the system may request that a cardiologist on call, at the time of a heart pain or low heartbeat event, should provide an acknowledgement of the message via his device. As another example, the system may request, simultaneously, a second opinion. In another embodiment, the system may prioritize potential recipients.

For example, the data table may indicate that cardiology personnel should be contacted for confirmation of a high emergency event before transmissions are sent to a concerned team personnel in a medical facility 504.

In an embodiment, the system may insert additional content to deliver to the transmission recipients based on the urgency level. In an embodiment, the system may construct a description of factors that it employed to determine the urgency level. For example, the system may create text that briefly recites the factors which contributed to a low level urgency label for the current medical condition.

FIG. 6A shows an example emergency message and content of the message that may be used for broadcasting or communicating with the vehicle infotainment system, medical facility, nearby devices, and emergency contacts according to an embodiment. In an embodiment, the message is similar to HL7 protocol according to the protocol described above in FIG. 4. Upon displaying the message on any display, the system removes the message header "XXX-YYY" and decoded in its full form for proper understanding of the message. In an embodiment, the message to the vehicle infotainment system, the medical facility, nearby devices, and emergency contacts in case of a low urgency condition, comprises a message comprising vehicle information, occupant information and the medical condition of the occupant. Vehicle information may comprise, vehicle make, vehicle type such as a car, truck etc., vehicle number, vehicle owner, vehicle color, vehicle chassis id etc. The message includes information on emergencies due to medical issues. FIG. 6A shows a sample emergency message to the vehicle infotainment system where the fields comprise an event type or emergency type, a vehicle location, and an occupant's information. In case of a low urgency condition or a no urgency condition a message may comprise vehicle information, occupant information, and the medical condition of the occupant. In cases where the urgency condition is medium to high, a second message is transmitted as shown in FIG. 6B. A decoder of the location message installed in the vehicle may produce a graphic of the locations as shown in FIG. 6A on an infotainment system.

FIG. 6B shows an example emergency message and content of the message that may be used for broadcasting or communicating with a medical facility according to an embodiment. In an embodiment, the message protocol is similar to HL7 protocol according to the protocol described above in FIG. 4. Upon displaying the message on any display, the system may remove the message header "XXX-YYY" and decodes the message in its full form for proper understanding of the message. In an embodiment, the message to a first responder comprises the alert signal and a message. The alert signal includes information on emergencies due to medical issues. In an embodiment, the system broadcasts the message to more than one medical facility. In an embodiment, the system broadcasts the message to a nearest medical facility first. A sample emergency message to the nearby facility is shown in FIG. 6B where the fields comprise an event type or emergency type, occupant information, health parameters (from one or more sensors in the vehicle, including wearable devices), vehicle details, occupant seating details, occupant pre-health condition details, occupant allergy details, and emergency contact details. Vehicle details may further comprise type of vehicle, seating capacity, etc. Vehicle details may comprise, vehicle make, vehicle type such as a car, truck etc., vehicle number, vehicle owner, vehicle color, vehicle chassis id etc. Occupant pre-health condition details can be either user provided details recorded in the vehicle system or medical service provider data from a cloud server. In an embodiment, the vehicle can collect the data, upon user's permission, and load the details in the vehicle system. In an embodiment, the system can provide encrypted details for security reasons. In an embodiment, the system can send a message to the third party, for example an insurer, to share the occupant's health related details to the medical center. In an embodiment, the system sends an encoded hyperlink that can provide access to the occupant's health records. A decoder of a medical facility, upon additional authentication via a password or a pin, can access the medical records. In an embodiment, the password or pin is sent in a separate message followed by the main message. In an embodiment, one or more portions of the message comprising medical records or medical data are encrypted.

The system may include security features. The security features can include data encryption using any of a variety of security protocols, e.g., HTTPS (HTTP secure), etc., and/or can include user authentication. User authentication can allow aspects of the system to be available to a particular user based on the identity of the user and/or the location from which the user is accessing the system. To that end, each user can have a unique username, password, and/or other security credentials to facilitate access to the system. The system checks the received security parameter information against a database of authorized users to determine whether the user is authorized and to what extent the user is permitted to interact with the system, view information stored in the system, and so forth. Examples of parties who can be permitted to access the system include occupants, potential occupants, significant others of occupants or potential occupants, friends of occupants or potential occupants, family members of occupants or potential occupants, doctors, nurses, medical assistants, appropriate bots, insurers, home care staff, and hospital administrators.

Figure 7:
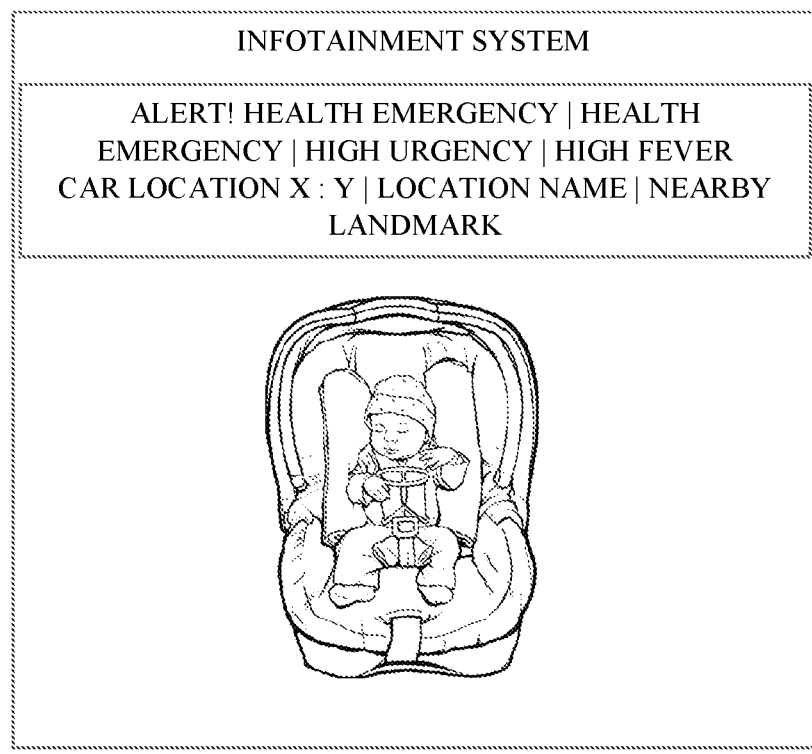
FIG. 7 shows a communication message that is displayed on a nearby vehicle on an infotainment system of the nearby vehicle which includes a graphic that is generated according to an embodiment.

FIG. 7 shows a broadcast message or a communication message displayed in an infotainment system which includes a graphic that is generated according to an embodiment. When the vehicle infotainment system, nearby devices, and medical facilities receive an emergency alert signal, the system, upon identifying such a message, may identify the location of the vehicle, the message in a graphical format for better understanding. The message may have an image of the vehicle seat and the occupant in the vehicle experiencing an emergency.

Figure 8:
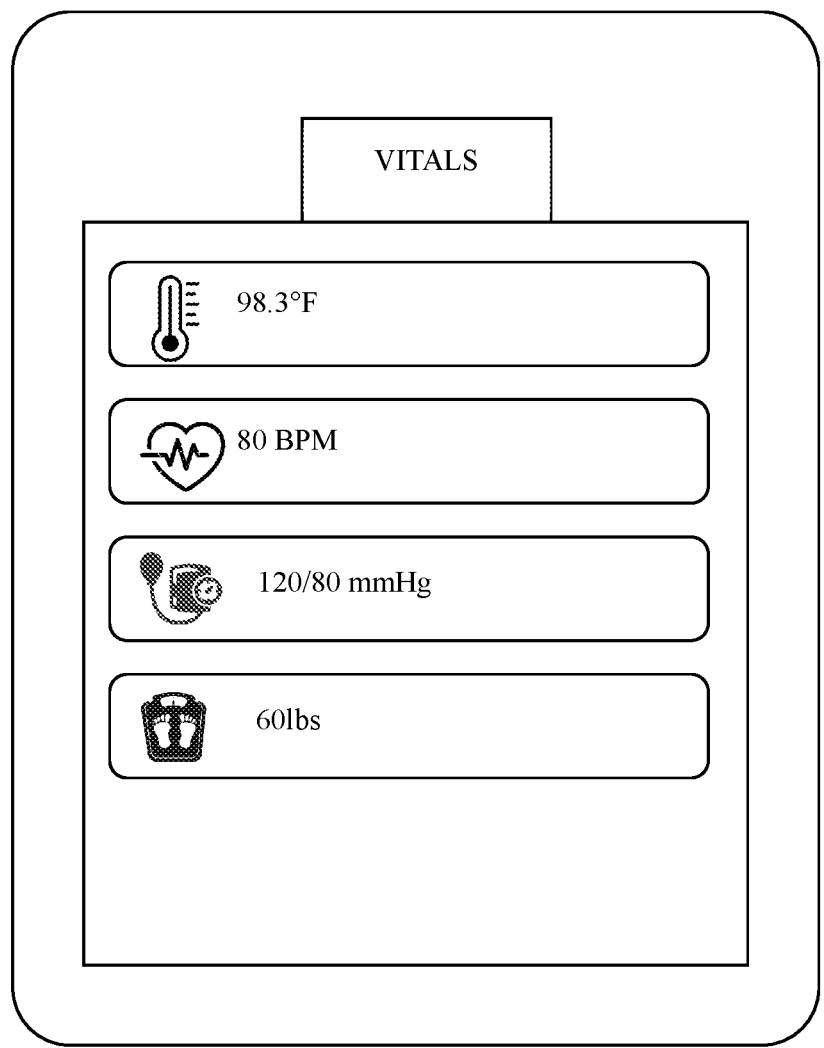
FIG. 8 shows a communication message that is displayed on a mobile device or an application according to one embodiment.

FIG. 8 shows a broadcast message or a communication message displayed on a display of a mobile device. The mobile device may have an application that comprises the system for health monitoring. The application may decode the message received by the mobile device. A decoder of a mobile device, upon additional authentication via a password or a pin, can access the medical records. In an embodiment, the password or pin is sent in a separate message followed by the main message. The decoder may decode the message and convert it into a message to be displayed on the display of the mobile device. In an embodiment, one or more portions of the message comprising medical records or medical data are encrypted. The system decodes the message in the application and then displayed on the display of the mobile device. The system converts the message into a user-friendly graphical user interface as shown in FIG. 8.

Figure 9:
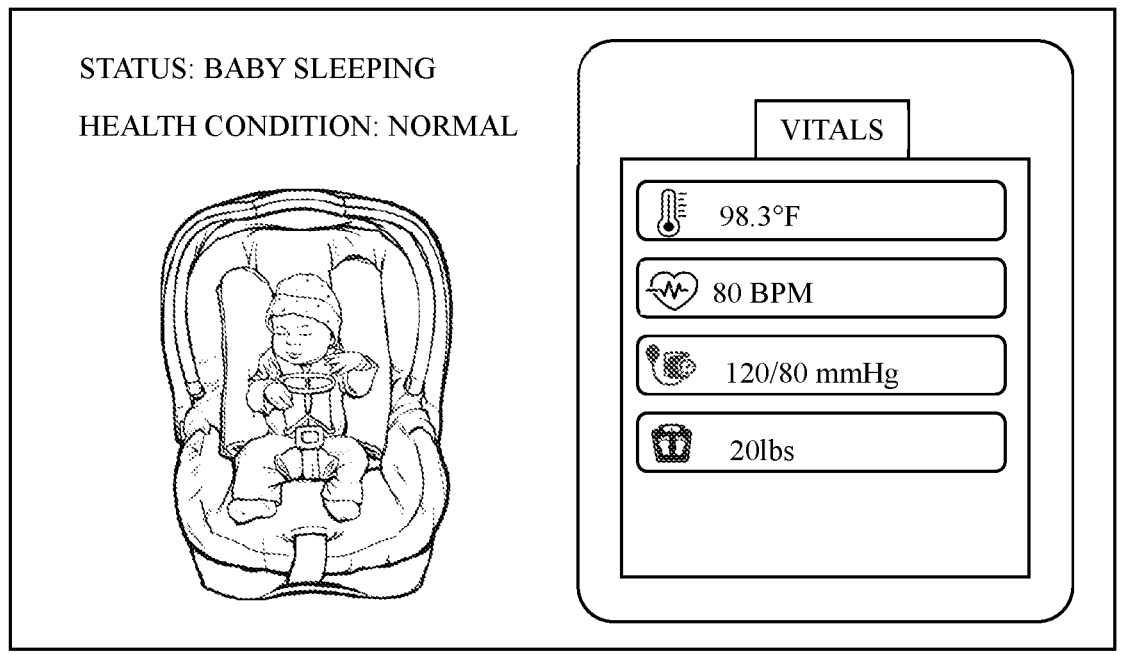
FIG. 9 shows a communication message that is displayed on the vehicle on an infotainment system of the vehicle which includes a graphic that is generated according to an embodiment.

FIG. 9 shows a broadcast message or a communication message that is displayed on a display of a vehicle infotainment system. The vehicle infotainment system may have an application that comprises the system for health monitoring. The application may decode the message received by the vehicle infotainment system. A decoder in the vehicle infotainment system, upon additional authentication via a password or a pin, can access the medical records. The decoder in the application may decode the message and convert the message into a displayable format on a display of the vehicle infotainment system. In an embodiment, the password or pin is sent in a separate message followed by the main message. In an embodiment, one or more portions of the message comprising medical records or medical data are encrypted. The message is decoded in the application and then displayed on the display of the mobile device.

In an embodiment, icons on a graphical user interface (GUI) or display of the infotainment system of a computer system are re-arranged based on a priority score of the content of the message. The processor tracks the messages that need to be displayed at a given time and generates a priority score, wherein the priority score is determined based on the action that needs to be taken by the user, the time available before the user input is needed, content of the message to be displayed, criticality of the user's input/action that needs to be taken, the sequence of the message or messages that need to be displayed and executed, and the safety of the overall scenario. For example, in case of a health emergency, the messages in queue for displaying could be an emergency signal, type of emergency, intimation that an alert is provided to the nearby vehicles, instructing a path for the driver to pull over, calling the emergency services, etc. In all these messages that need a driver's attention, a priority score is provided based on the actions that need to be taken by the user, the time available for the user to receive the displayed message and react with an action, the content of the message, criticality of the user's input/action, sequence of the messages that need to be executed, and safety of the overall scenario. Considering the above example, the message that intimates the user/driver that an alert has been provided to nearby vehicles may be of lower priority as compared to instructing the path for the driver to pull over. Therefore, the pull over directions for the path message takes priority and takes such a place on the display (example, center of the display) which can grab the users' attention immediately. The priority of the messages are evaluated dynamically as the situation is evolving and thus the display icons, positions, and sizes of the text or icon on the display are changed in real time and dynamically. In an embodiment, more than one message is displayed and highlighted as per the situation and the user's actions. Further, while pulling over, if an unsafe scenario is found for example, a car is changing lanes which may obstruct the user's vehicle, the message dynamically changes and warns the driver about the developing scenario.

Figure 10A:
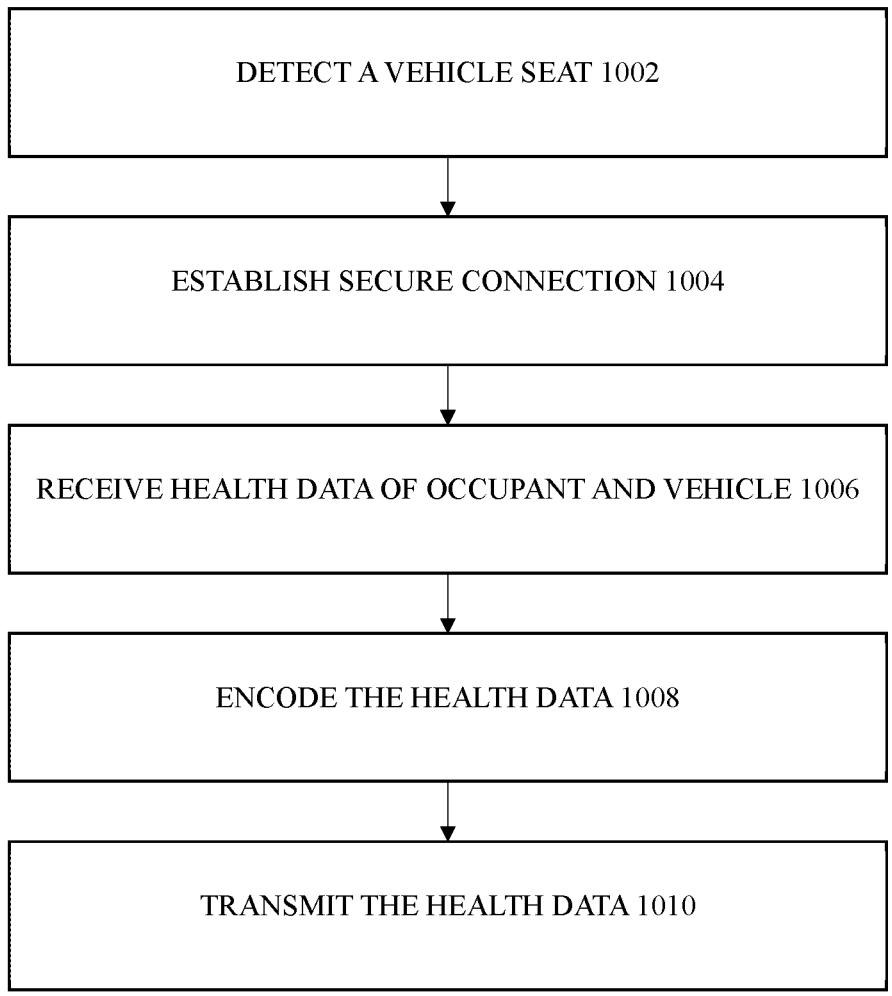
FIG. 10A shows a flowchart of the method to monitor and transmit the health data.

FIG. 10A shows a method to communicatively connect a car seat to retrieve health data according to one embodiment.

The system detects a vehicle seat, at step 1002. A start signal is sent from a vehicle control system to the vehicle seat. If the vehicle seat is connected to the vehicle control system through a connector, an acknowledgement is received from the vehicle seat.

Upon receiving the acknowledgement from the vehicle seat, a secure connection is established between the vehicle seat and the vehicle control system, at step 1004.

The vehicle control system receives data of the vehicle seat and a health data of the occupant of the vehicle seat, at step 1006. The first data comprises at least one of a first position of the vehicle seat, a second position of the occupant on the vehicle seat, a weight of the occupant, a height of the occupant, and a pressure on the seat belt. The second data comprises a first image of the vehicle seat's position, a second image of a second position of the occupant on the vehicle seat.

The received data is then encoded by identifying protected health information for transmission of a secure data message using a protocol similar to the HL7 protocol, at step 1008.

At step 1010, the encoded message is then transmitted to various recipients such as a medical facility, a vehicle infotainment system, emergency contact and to nearby devices in case of a high urgency condition. In an embodiment, the transmission is in real time via the communication module to an application installed in a central server, thereon, the application is configured to receive the data from the central server.

Figure 10B:
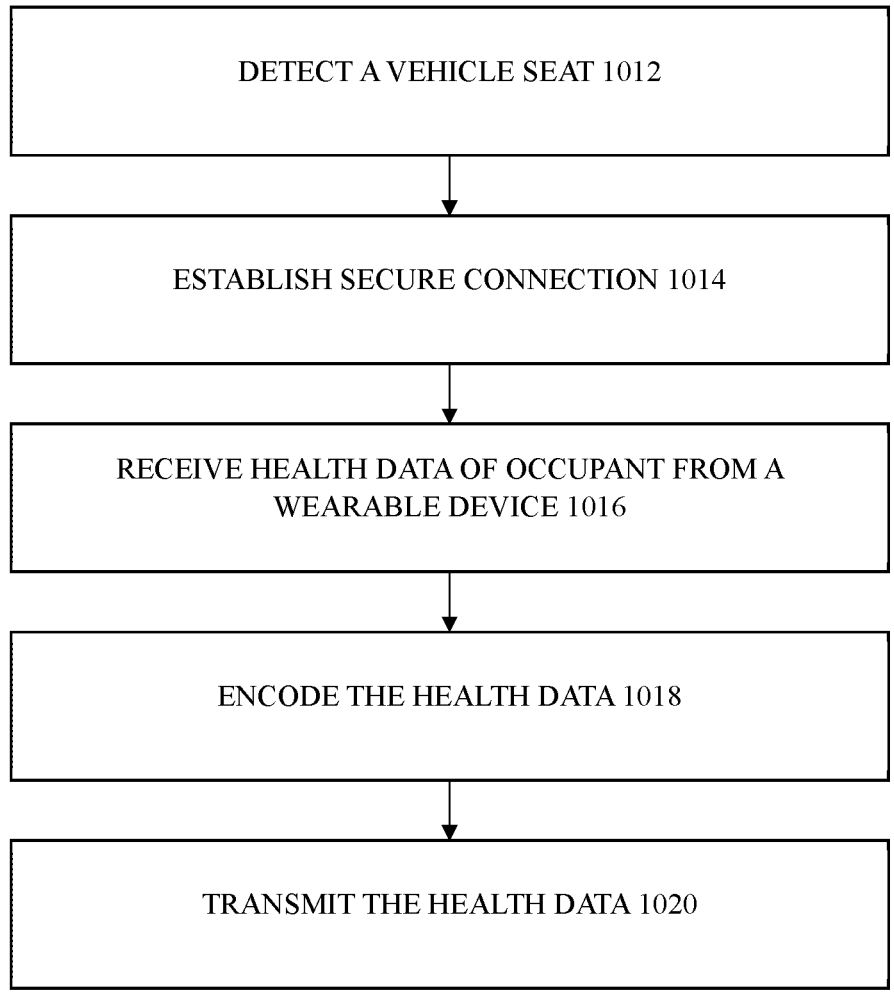
FIG. 10B shows a flowchart of the method to monitor and transmit the health data received from a wearable device according to one embodiment.

FIG. 10B shows a method to communicatively connect a car seat to retrieve health data according to another embodiment.

The system detects a vehicle seat, at step 1012. A start signal is sent from a vehicle control system to the vehicle seat. If the vehicle seat is connected to the vehicle control system through a connector, an acknowledgement is received from the vehicle seat.

Upon receiving the acknowledgement from the vehicle seat, a secure connection is established between the vehicle seat and the vehicle control system, at step 1014.

The vehicle control system receives data of the vehicle seat and a health data of the occupant of the vehicle seat, at step 1016. The first data comprises at least one of a first position of the vehicle seat, a second position of the occupant on the vehicle seat, a weight of the occupant, a height of the occupant, and a pressure on the seat belt. The second data comprises a first image of the vehicle seat's position, a second image of a second position of the occupant on the vehicle seat, and a third image of a size of the vehicle seat according to the height and weight of the occupant. The first data of the vehicle seat further comprises data related to the vehicle seat position and if the vehicle seat is secured in the right position. The system is configured to receive a third data from a wearable device. The third data comprises at least one of a health and wellness data of the occupant comprising a heart rate, a blood pressure, a skin color, conscious state of the occupant and temperature of the occupant.

The received data is then encoded by identifying protected health information for transmission of a secure data message using a protocol similar to the HL7 protocol, at step 1018.

At step 1020, the encoded message is then transmitted to various recipients such as a medical facility, a vehicle infotainment system, emergency contact and to nearby devices in case of a high urgency condition. In an embodiment, the transmission is in real time via the communication module to an application installed in a central server, thereon, the application is configured to receive the data from the central server.

In an embodiment, the system further comprises a cyber security module wherein the cyber security module comprises an information security management module providing isolation between the communication module and servers.

In an embodiment, the information security management module is operable to, receive data from the communication module, exchange a security key at a start of the communication between the communication module and the server, receive the security key from the server, authenticate an identity of the server by verifying the security key, analyze the security key for a potential cyber security threat, negotiate an encryption key between the communication module and the server, encrypt the data; and transmit the encrypted data to the server when no cyber security threat is detected.

In an embodiment, the information security management module is operable to exchange a security key at a start of the communication between the communication module and the server, receive the security key from the server, authenticate an identity of the server by verifying the security key, analyze the security key for a potential cyber security threat, negotiate an encryption key between the system and the server, receive encrypted data from the server, decrypt the encrypted data, perform an integrity check of the decrypted data and transmit the decrypted data to the communication module when no cyber security threat is detected.

In an embodiment, the system may comprise a cyber security module.

In one aspect, a secure communication management (SCM) computer device for providing secure data connections is provided. The SCM computer device includes a processor in communication with memory. The processor is programmed to receive, from a first device, a first data message. The first data message is in a standardized data format. The processor is also programmed to analyze the first data message for potential cyber security threats. If the determination is that the first data message does not contain a cyber security threat, the processor is further programmed to convert the first data message into a first data format associated with the vehicle environment and transmit the converted first data message to the vehicle system using a first communication protocol associated with the vehicle system.

According to an embodiment, secure authentication for data transmissions comprises, provisioning a hardware-based security engine (HSE) located in communications system, said HSE having been manufactured in a secure environment and certified in said secure environment as part of an approved network; performing asynchronous authentication, validation and encryption of data using said HSE, storing user permissions data and connection status data in an access control list used to define allowable data communications paths of said approved network, enabling communications of the communications system with other computing system subjects to said access control list, performing asynchronous validation and encryption of data using security engine including identifying a user device (UD) that incorporates credentials embodied in hardware using a hardware-based module provisioned with one or more security aspects for securing the system, wherein security aspects comprising said hardware-based module communicating with a user of said user device and said HSE.

Figure 11A:
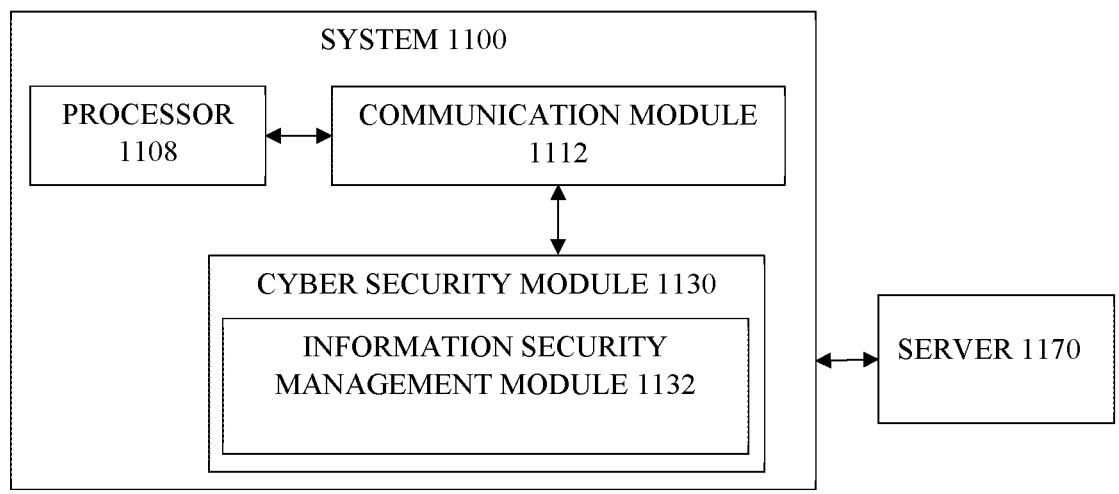
FIG. 11A shows a block diagram of the cyber security module in view of the system and server.

In an embodiment, FIG. 11A shows the block diagram of the cyber security module. The communication of data between the system 1100 and the server 1170 through the communication module 1112 is first verified by the information security management module 1132 before being transmitted from the system to the server or from the server to the system. The information security management module is operable to analyze the data for potential cyber security threats, to encrypt the data when no cyber security threat is detected, and to transmit the data encrypted to the system or the server.

Figure 11B:
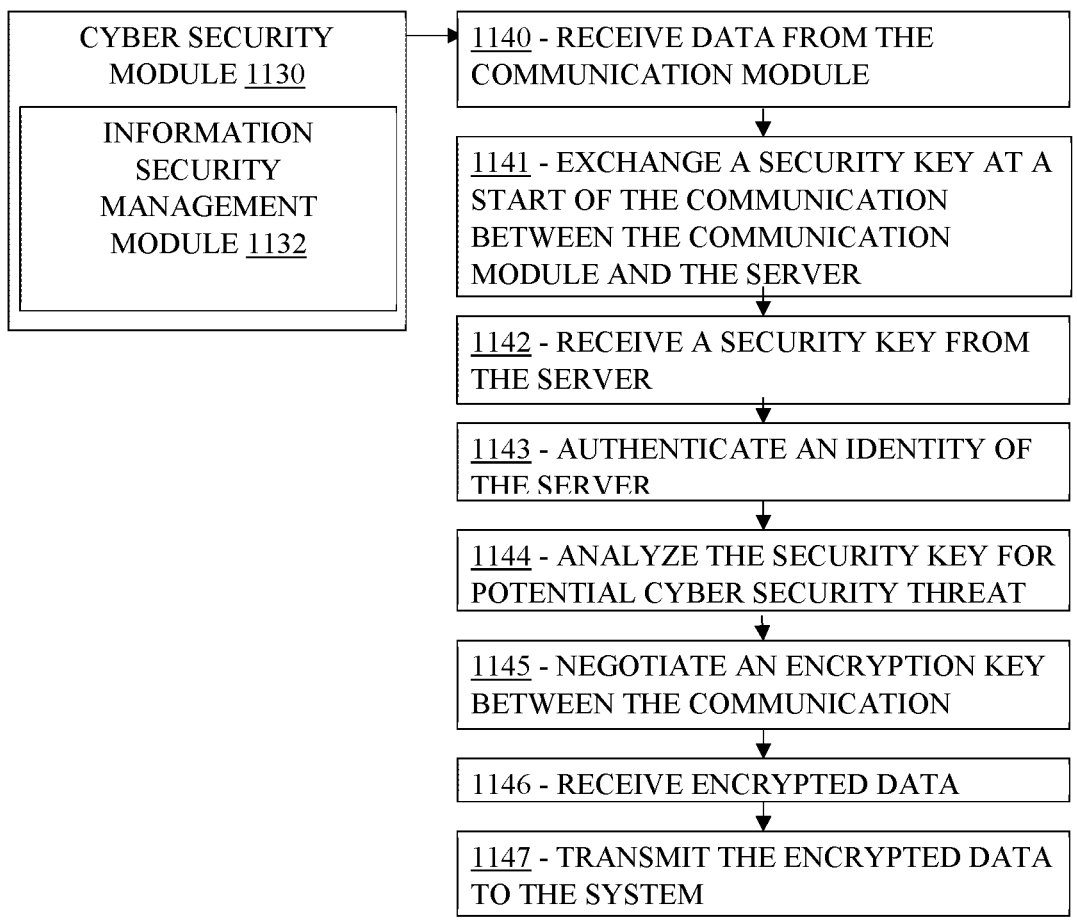
FIG. 11B shows an embodiment of the cyber security module.

In an embodiment, the cyber security module further comprises an information security management module providing isolation between the system and the server. FIG. 11B shows the flowchart of securing the data through the cyber security module 1130. At step 1140, the information security management module is operable to receive data from the communication module. At step 1141, the information security management module exchanges a security key at a start of the communication between the communication module and the server. At step 1142, the information security management module receives a security key from the server. At step 1143, the information security management module authenticates an identity of the server by verifying the security key. At step 1144, the information security management module analyzes the security key for potential cyber security threats. At step 1145, the information security management module negotiates an encryption key between the communication module and the server. At step 1146, the information security management module receives the encrypted data. At step 1147, the information security management module transmits the encrypted data to the server when no cyber security threat is detected.

Figure 11C:
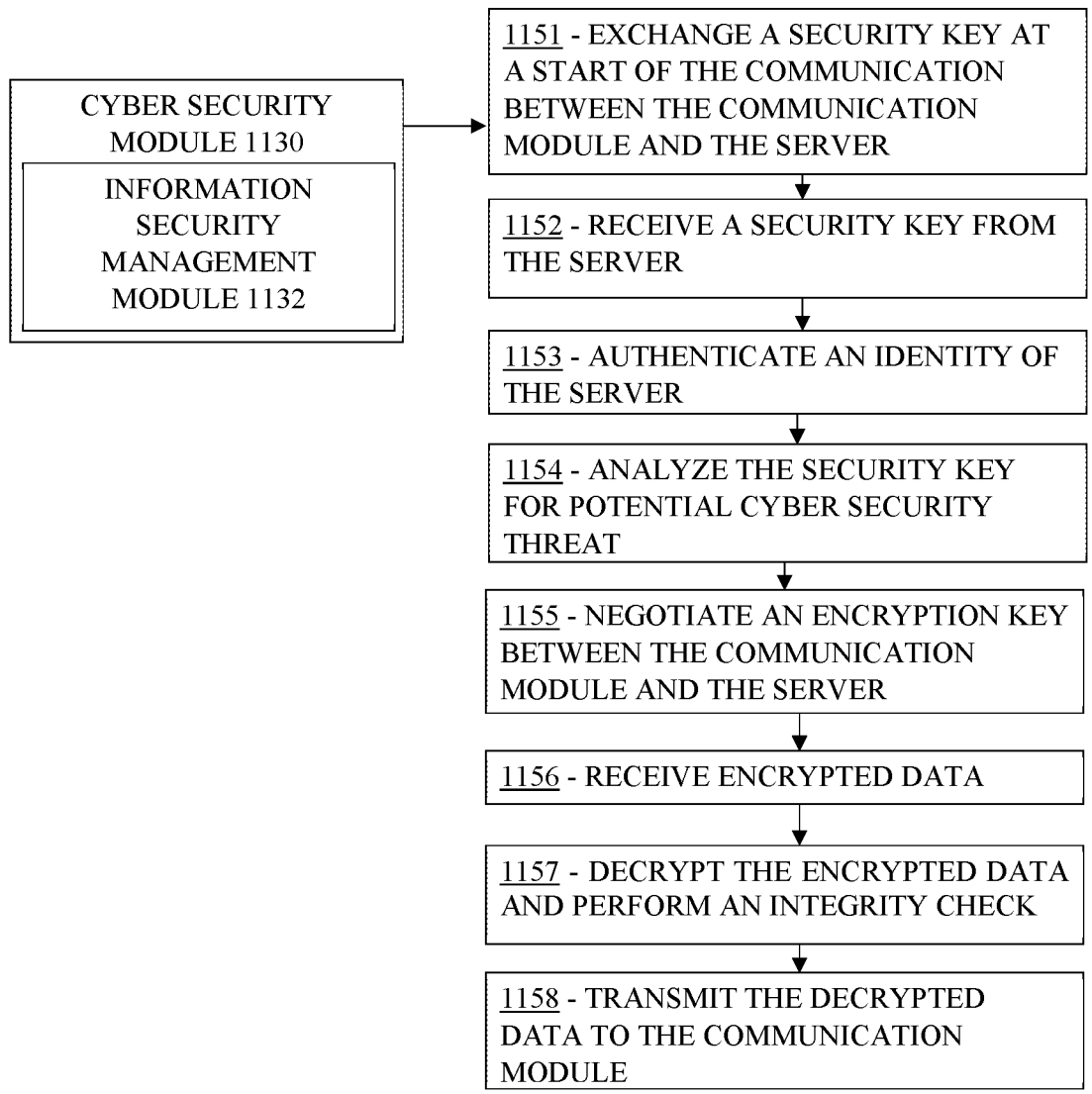
FIG. 11C shows another embodiment of the cyber security module.

In an embodiment, FIG. 11C shows the flowchart of securing the data through the cyber security module 1130. At step 1151, the information security management module is operable to: exchange a security key at a start of the communication between the communication module and the server. At step 1152, the information security management module receives a security key from the server. At step 1153, the information security management module authenticates an identity of the server by verifying the security key. At step 1154, the information security management module analyzes the security key for potential cyber security threats. At step 1155, the information security management module negotiates an encryption key between the communication module and the server. At step 1156, the information security management module receives encrypted data. At step 1157, the information security management module decrypts the encrypted data, and performs an integrity check of the decrypted data. At step 1158, the information security management module transmits the decrypted data to the communication module when no cyber security threat is detected.

In an embodiment, the integrity check is a hash-signature verification using a Secure Hash Algorithm 256 (SHA256) or a similar method.

In an embodiment, the information security management module is configured to perform asynchronous authentication and validation of the communication between the communication module and the server.

In an embodiment, the information security management module is configured to raise an alarm if a cyber security threat is detected. In an embodiment, the information security management module is configured to discard the encrypted data received if the integrity check of the encrypted data fails.

In an embodiment, the information security management module is configured to check the integrity of the decrypted data by checking accuracy, consistency, and any possible data loss during the communication through the communication module.

In an embodiment, the server is physically isolated from the system through the information security management module. When the system communicates with the server as shown in FIG. 11A, identity authentication is first carried out on the system and the server. The system is responsible for communicating/exchanging a public key of the system and a signature of the public key with the server. The public key of the system and the signature of the public key are sent to the information security management module. The information security management module decrypts the signature and verifies whether the decrypted public key is consistent with the received original public key or not. If the decrypted public key is verified, the identity authentication is passed. Similarly, the system and the server carry out identity authentication on the information security management module. After the identity authentication is passed on to the information security management module, the two communication parties, the system, and the server, negotiate an encryption key and an integrity check key for data communication of the two communication parties through the authenticated asymmetric key. A session ID number is transmitted in the identity authentication process, so that the key needs to be bound with the session ID number; when the system sends data to the outside, the information security gateway receives the data through the communication module, performs integrity authentication on the data, then encrypts the data through a negotiated secret key, and finally transmits the data to the server through the communication module. When the information security management module receives data through the communication module, the data is decrypted first, integrity verification is carried out on the data after decryption, and if verification is passed, the data is sent out through the communication module; otherwise, the data is discarded.

In an embodiment, the identity authentication is realized by adopting an asymmetric key with a signature.

In an embodiment, the signature is realized by a pair of asymmetric keys which are trusted by the information security management module and the system, wherein the private key is used for signing the identities of the two communication parties, and the public key is used for verifying that the identities of the two communication parties are signed. Signing identity comprises a public and a private key pair. In other words, signing identity is referred to as the common name of the certificates which are installed in the user's machine.

In an embodiment, both communication parties need to authenticate their own identities through a pair of asymmetric keys, and a task in charge of communication with the information security management module of the system is identified by a unique pair of asymmetric keys.

In an embodiment, the dynamic negotiation key is encrypted by adopting an Rivest-Shamir-Adleman (RSA) encryption algorithm. RSA is a public-key cryptosystem that is widely used for secure data transmission. The negotiated keys include a data encryption key and a data integrity check key.

In an embodiment, the data encryption method is a Triple Data Encryption Algorithm (3DES) encryption algorithm. The integrity check algorithm is a Hash-based Message Authentication Code (HMAC-MD5-128) algorithm. When data is output, the integrity check calculation is carried out on the data, the calculated Message Authentication Code (MAC) value is added with the header of the value data message, then the data (including the MAC of the header) is encrypted by using a 3DES algorithm, the header information of a security layer is added after the data is encrypted, and then the data is sent to the next layer for processing. In an embodiment the next layer refers to a transport layer in the Transmission Control Protocol/Internet Protocol (TCP/IP) model.

The information security management module ensures the safety, reliability, and confidentiality of the communication between the system and the server through the identity authentication when the communication between the two communication parties starts the data encryption and data integrity authentication. The method is particularly suitable for an embedded platform which has less resources and is not connected with a Public Key Infrastructure (PKI) system and can ensure that the safety of the data on the server cannot be compromised by a hacker attack under the condition of the Internet by ensuring the safety and reliability of the communication between the system and the server.

Figure 12A:
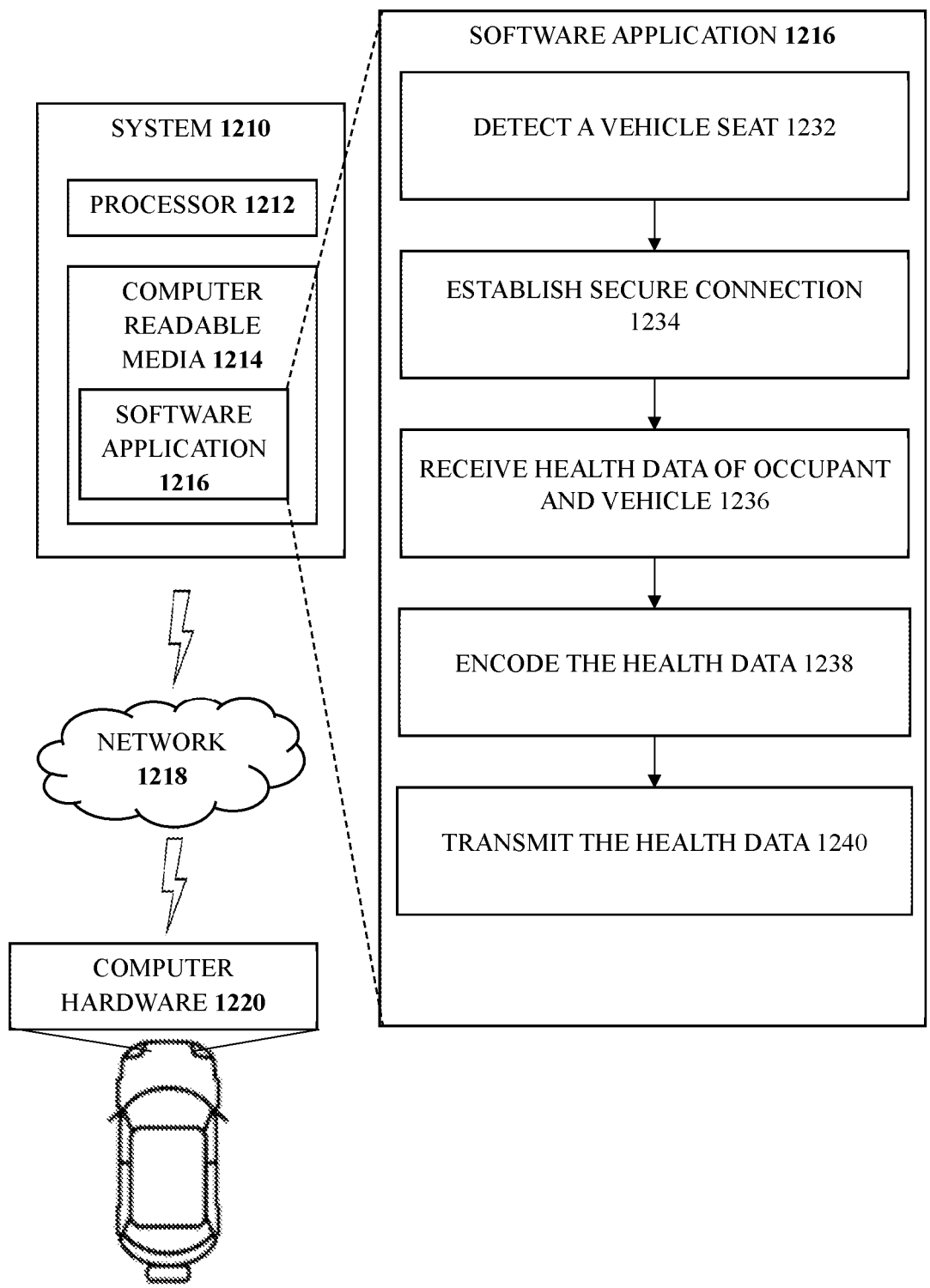
FIG. 12A shows a system for installation of software code for communicatively connecting a car seat to retrieve health data according to an embodiment.

FIG. 12A shows a system for installation of software code for communicatively connecting a car seat to retrieve health data according to an embodiment. The system 1210 comprises a processor 1212 and a computer readable media 1214. The computer readable media 1214 is a non-transitory storage media comprising a software application 1216. The system 1210 is in communication with computer hardware 1220 of the vehicle through a network 1218 via a communication module in the system. The system 1210 is configured for installing a software application 1216, via a software installation package provided over a computer network 1218, onto the computing hardware 1220 associated with the vehicle. The software application comprises a set of instructions executable by a computing hardware and stored in a non-transitory storage medium that, when executed, cause the computing hardware to implement operations comprising step described below:

At step 1232, the system detects a vehicle seat. A vehicle control system sends a start signal to the vehicle seat. The system receives an acknowledgement signal from the vehicle seat if the vehicle seat is connected to the vehicle control system through a connector.

At step 1234, the system establishes a secured connection between the vehicle seat and the vehicle control system, on receiving the acknowledgement from the vehicle seat.

At step 1236, the vehicle control system receives data of the vehicle seat and a health data of the occupant of the vehicle seat. The first data comprises at least one of a first position of the vehicle seat, a second position of the occupant on the vehicle seat, a weight of the occupant, a height of the occupant, and a pressure on the seat belt. The second data comprises a first image of the vehicle seat's position, a second image of a second position of the occupant on the vehicle seat, and a third image of a size of the vehicle seat according to the height and weight of the occupant. The first data of the vehicle seat further comprises data related to the vehicle seat position and if the vehicle seat is secured in the right position.

At step 1238, the system encodes the received data by identifying protected health information for transmission of a secure data message using a protocol similar to the HL7 protocol.

At step 1240, the encoded message is then transmitted to various recipients such as a medical facility, a vehicle infotainment system, emergency contact, and to nearby devices in case of a high urgency condition. In an embodiment, the transmission is in real time via the communication module to an application installed in a central server, thereon, the application configured to receive the data from the central server.

Figure 12B:
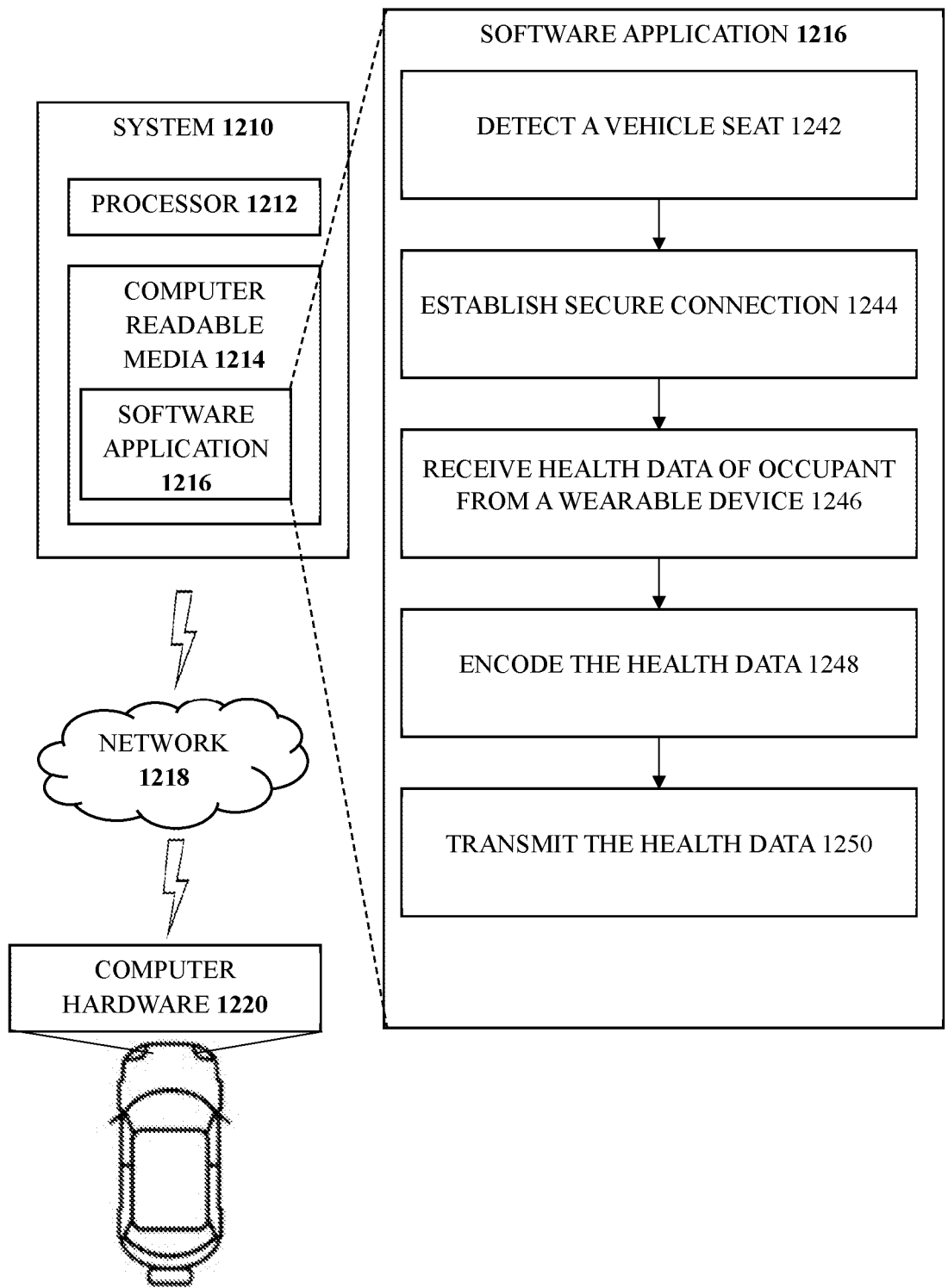
FIG. 12B shows a system for installation of software code for communicatively connecting a car seat to retrieve health data according to another embodiment.

FIG. 12B shows a system for installation of software code for communicatively connecting a car seat to retrieve health data according to an embodiment. The system 1210 comprises a processor 1212 and a computer readable media 1214. The computer readable media 1214 is a non-transitory storage media comprising a software application 1216. The system 1210 is in communication with computer hardware 1220 of the vehicle through a network 1218 via a communication module in the system. The system 1210 is configured for installing a software application 1216, via a software installation package provided over a computer network 1218, onto the computing hardware 1220 associated with the vehicle. The software application comprises a set of instructions executable by a computing hardware and stored in a non-transitory storage medium that, when executed, cause the computing hardware to implement operations comprising step described below:

At step 1242, the system detects a vehicle seat. A vehicle control system sends a start signal to the vehicle seat. The system receives an acknowledgement signal from the vehicle seat if the vehicle seat is connected to the vehicle control system through a connector.

At step 1244, the system establishes a secured connection between the vehicle seat and the vehicle control system, on receiving the acknowledgement from the vehicle seat.

At step 1246, the vehicle control system receives data of the vehicle seat and a health data of the occupant of the vehicle seat. The first data comprises at least one of a first position of the vehicle seat, a second position of the occupant on the vehicle seat, a weight of the occupant, a height of the occupant, and a pressure on the seat belt. The second data comprises a first image of the vehicle seat's position, a second image of a second position of the occupant on the vehicle seat, and a third image of a size of the vehicle seat according to the height and weight of the occupant. The first data of the vehicle seat further comprises data related to the vehicle seat position and if the vehicle seat is secured in the right position. In an embodiment the vehicle control system receives a third data from a wearable device. The third data comprises at least one of a health and wellness data of the occupant comprising a heart rate, a blood pressure, a skin color, conscious state of the occupant and temperature of the occupant.

At step 1248, the system encodes the received data by identifying protected health information for transmission of a secure data message using a protocol similar to the HL7 protocol.

At step 1250, the encoded message is then transmitted to various recipients such as a medical facility, a vehicle infotainment system, emergency contact, and to nearby devices in case of a high urgency condition. In an embodiment, the transmission is in real time via the communication module to an application installed in a central server, thereon, the application configured to receive the data from the central server.

Figure 13A:
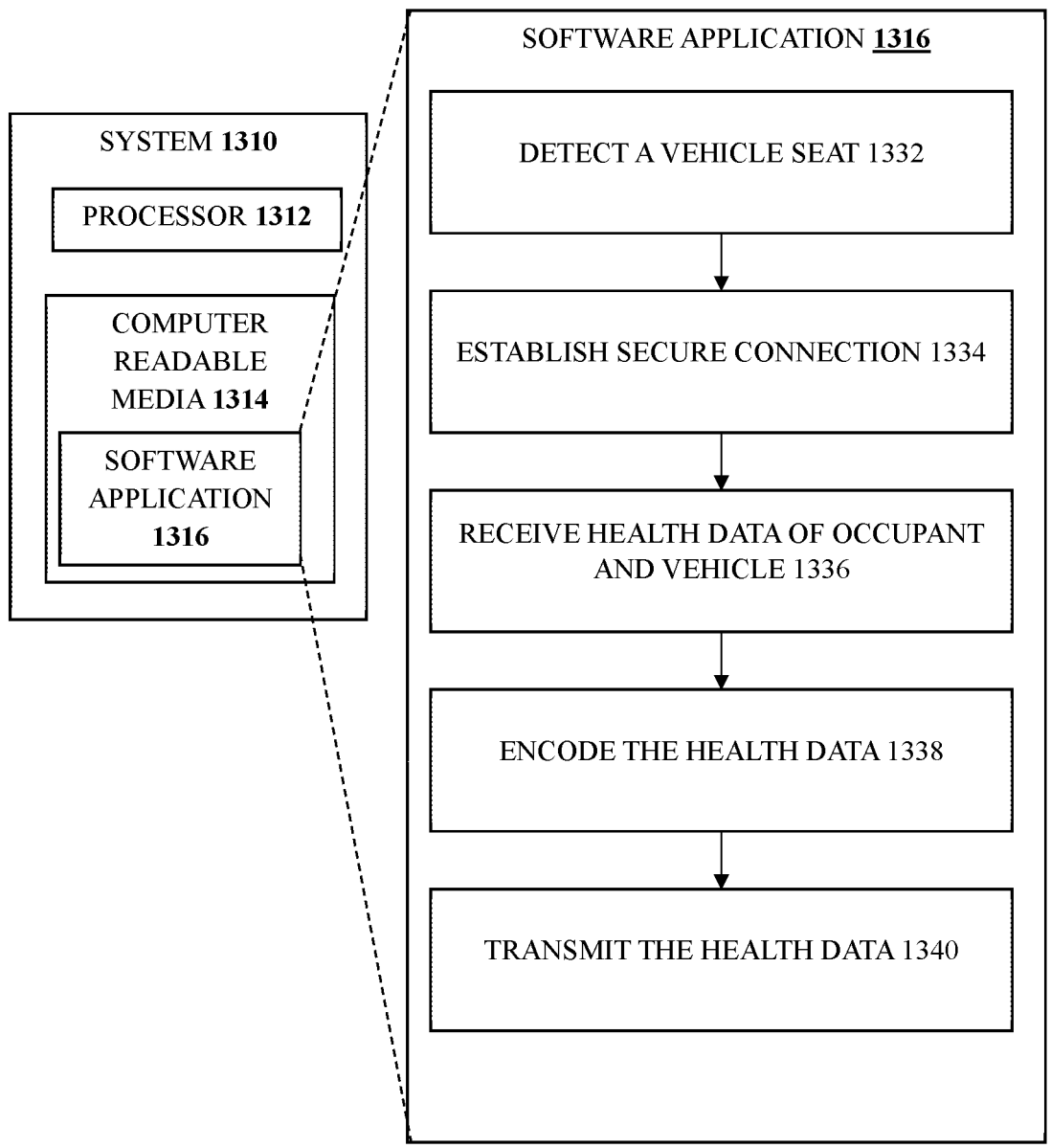
FIG. 13A shows the system with a non-transitory storage medium with the software code for communicatively connecting a car seat to retrieve health data according to an embodiment.

FIG. 13A shows the system with a non-transitory storage medium with the software code for communicatively connecting a car seat to retrieve health data according to an embodiment. The system 1310 comprises a processor 1312 and a computer readable media 1314. The computer readable media 1314 is a non-transitory storage media comprising a software application 1316. The non-transitory medium executes the instructions as described herein:

In an embodiment, at step 1332, the software application executes an instruction for detecting a vehicle seat. A vehicle control system sends a start signal to the vehicle seat. The system receives an acknowledgement signal from the vehicle seat if the vehicle seat is connected to the vehicle control system through a connector.

At step 1334, the software application executes an instruction for establishing a secured connection between the vehicle seat and the vehicle control system, on receiving the acknowledgement from the vehicle seat.

At step 1336, the software application executes an instruction for the vehicle control system to receive data of the vehicle seat and a health data of the occupant of the vehicle seat. The first data comprises at least one of a first position of the vehicle seat, a second position of the occupant on the vehicle seat, a weight of the occupant, a height of the occupant, and a pressure on the seat belt. The second data comprises a first image of the vehicle seat's position, a second image of a second position of the occupant on the vehicle seat, and a third image of a size of the vehicle seat according to the height and weight of the occupant. The first data of the vehicle seat further comprises data related to the vehicle seat position and if the vehicle seat is secured in the right position.

At step 1338, the software application executes an instruction for encodes the received data by identifying protected health information for transmission of a secure data message using a protocol similar to the HL7 protocol.

At step 1340, the software application executes an instruction for transmitting to various recipients such as a medical facility, a vehicle infotainment system, emergency contact and also to nearby devices in case of a high urgency condition. In an embodiment, the transmission is in real time via the communication module to an application installed in a central server, thereon, the application being configured to facilitate receipt of the data from the central server.

Figure 13B:
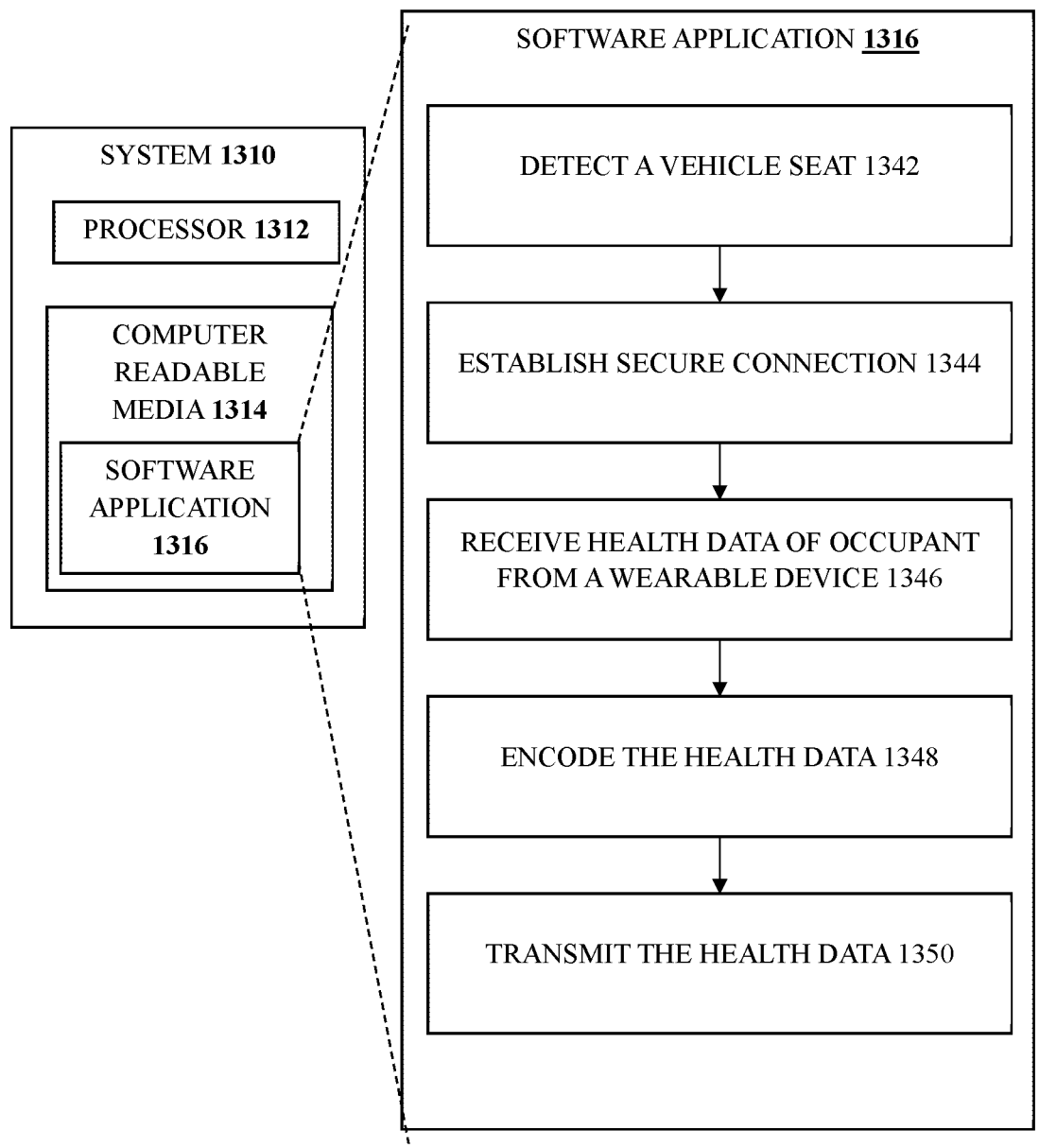
FIG. 13B shows the system with a non-transitory storage medium with the software code for communicatively connecting a car seat to retrieve health data according to another embodiment.

FIG. 13B shows the system with a non-transitory storage medium with the software code for communicatively connecting a car seat to retrieve health data according to an embodiment. The system 1310 comprises a processor 1312 and a computer readable media 1314. The computer readable media 1314 is a non-transitory storage media comprising a software application 1316. The non-transitory medium executes the instructions as described herein:

In an embodiment, at step 1342, the software application executes an instruction for detecting a vehicle seat. A vehicle control system sends a start signal to the vehicle seat. The system receives an acknowledgement signal from the vehicle seat if the vehicle seat is connected to the vehicle control system through a connector.

At step 1344, the software application executes an instruction for establishing a secured connection between the vehicle seat and the vehicle control system, on receiving the acknowledgement from the vehicle seat.

At step 1346, the software application executes an instruction for the vehicle control system to receive data of the vehicle seat and a health data of the occupant of the vehicle seat. The first data comprises at least one of a first position of the vehicle seat, a second position of the occupant on the vehicle seat, a weight of the occupant, a height of the occupant, and a pressure on the seat belt. The second data comprises a first image of the vehicle seat's position, a second image of a second position of the occupant on the vehicle seat, and a third image of a size of the vehicle seat according to the height and weight of the occupant. The first data of the vehicle seat further comprises data related to the vehicle seat position and if the vehicle seat is secured in the right position. In an embodiment the vehicle control system receives a third data from a wearable device. The third data comprises at least one of a health and wellness data of the occupant comprising a heart rate, a blood pressure, a skin color, conscious state of the occupant and temperature of the occupant.

At step 1348, the software application executes an instruction for encodes the received data by identifying protected health information for transmission of a secure data message using a protocol similar to the HL7 protocol.

At step 1350, the software application executes an instruction for transmitting to various recipients such as a medical facility, a vehicle infotainment system, emergency contact and also to nearby devices in case of a high urgency condition. In an embodiment, the transmission is in real time via the communication module to an application installed in a central server, thereon, the application being configured to facilitate receipt of the data from the central server.

Figure 14:
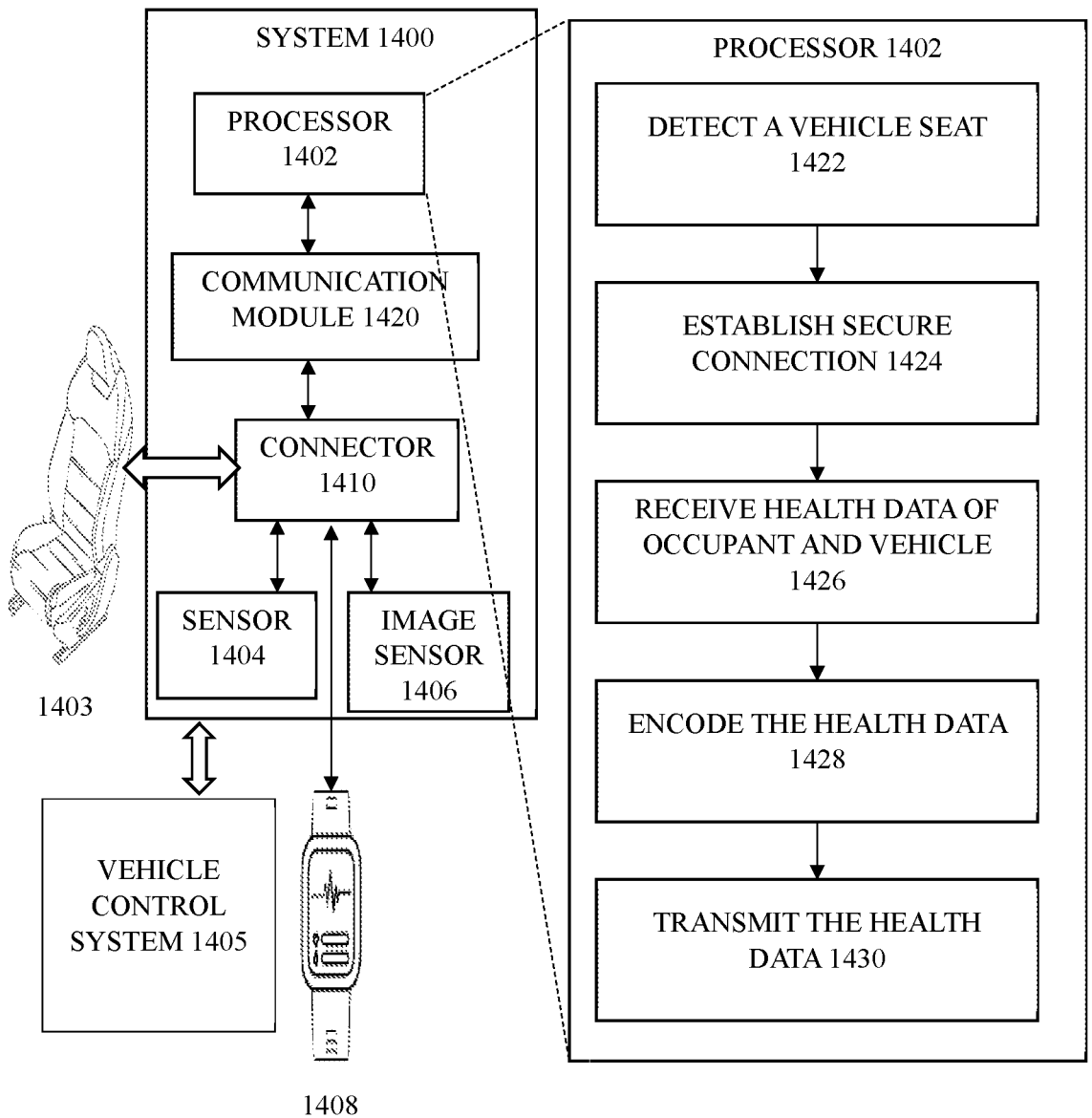
FIG. 14 shows a block diagram for a system to monitor health data in one embodiment.

FIG. 14 shows a block diagram for a system to monitor health data with a wearable device, in an embodiment. The system comprises a sensor 1404, an image sensor 1406, a wearable device 1408 and a processor 1402. The processor 1402 receives data of vehicle seat 1403 and health of an occupant from the image sensor 1406 and the sensor 1404 and the wearable device through the connector 1410. The system to monitor health data communicates with the vehicle seat and the vehicle control system 1405 through the communication module 1420 via the connector 1410.

Processor 1402 is configured to perform:

The system detects a vehicle seat, at step 1422. A start signal is sent from a vehicle control system to the vehicle seat. If the vehicle seat is connected to the vehicle control system through a connector, an acknowledgement is received from the vehicle seat.

Upon receiving the acknowledgement from the vehicle seat, a secure connection is established between the vehicle seat and the vehicle control system, at step 1424.

The vehicle control system receives data of the vehicle seat and a health data of the occupant of the vehicle seat, at step 1426. The first data comprises at least one of a first position of the vehicle seat, a second position of the occupant on the vehicle seat, a weight of the occupant, a height of the occupant, and a pressure on the seat belt. The second data comprises a first image of the vehicle seat's position, a second image of a second position of the occupant on the vehicle seat, and a third image of a size of the vehicle seat according to the height and weight of the occupant. The first data of the vehicle seat further comprises data related to the vehicle seat position and if the vehicle seat is secured in the right position. The system is configured to receive a third data from a wearable device. The third data comprises at least one of a health and wellness data of the occupant comprising a heart rate, a blood pressure, a skin color, conscious state of the occupant and temperature of the occupant.

The received data is then encoded by identifying protected health information for transmission of a secure data message using a protocol similar to the HL7 protocol, at step 1428.

At step 1430, the encoded message is then transmitted to various recipients such as a medical facility, a vehicle infotainment system, emergency contact and to nearby devices in case of a high urgency condition. In an embodiment, the transmission is in real time via the communication module to an application installed in a central server, thereon, the application is configured to receive the data from the central server.

The embodiments described herein can be directed to one or more of a system, a method, an apparatus, and/or a computer program product at any possible technical detail level of integration. The computer program product can include a computer readable storage medium (or media) having computer readable program instructions thereon for causing a processor to carry out aspects of the one or more embodiments described herein. The computer readable storage medium can be a tangible device that can retain and store instructions for use by an instruction execution device. For example, the computer readable storage medium can be, but is not limited to, an electronic storage device, a magnetic storage device, an optical storage device, an electromagnetic storage device, a superconducting storage device, and/or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon and/or any suitable combination of the foregoing. A computer readable storage medium, as used herein, does not construe transitory signals per se, such as radio waves and/or other freely propagating electromagnetic waves, electromagnetic waves propagating through a waveguide and/or other transmission media (e.g., light pulses passing through a fiber-optic cable), and/or electrical signals transmitted through a wire.

The descriptions of the one or more embodiments are for purposes of illustration but are not exhaustive or limiting to the embodiments described herein. Many modifications and variations will be apparent to those of ordinary skill in the art without departing from the scope and spirit of the described embodiments. The terminology used herein best explains the principles of the embodiments, the practical application and/or technical improvement over technologies found in the marketplace, and/or to enable others of ordinary skill in the art to understand the embodiments described herein.

The present invention is embodied in other specific forms without departing from its spirit or characteristics. The described embodiments are to be considered in all respects only as illustrative and not restrictive. The scope of the invention is, therefore, indicated by the appended claims rather than by the foregoing description. All variations which come within the meaning and range of equivalency of the claims are to be embraced within their scope.

What is claimed is:

1. A system, wherein the system is configured to be a component of a vehicle;
wherein the system comprising:
a sensor;
an image sensor;
a connector;
a communication module; and
a processor; and
wherein the processor is configured to:
detect a vehicle seat in the vehicle;
establish a secured connection with the vehicle seat through the connector;
receive a first data from the sensor and a second data from the image sensor through the connector, the first data and the second data being indicative of an information gathered regarding at least one parameter related to at least one of a condition of the vehicle seat, a health and wellness of an occupant of the vehicle, and the connector being configured to facilitate gathering of the information;
encode the first data and the second data by identifying protected health information for transmission of a secure data message using a protocol; and
transmit the first data and the second data in real time via the communication module to an application installed in a central server thereon, the application being configured to facilitate receipt of the first data and the second data from the central server, and
wherein the secure data message generated using the protocol comprises: a vehicle information, a location of the vehicle, an information related to the occupant, a health parameter, a seating detail of the occupant, a pre-health condition detail of the occupant, an allergy detail of the occupant, an emergency contact detail, other occupants of the vehicle, and a type of medical emergency detected.

2. The system of claim 1, wherein the vehicle seat comprises at least one of a car seat, a child car seat, and a pet car seat.

3. The system of claim 2, wherein the sensor comprises at least one of a seat belt sensor, a position sensor, a pressure sensor, a liquid detection sensor, weight sensor, an infrared sensor, an optical sensor, a moisture sensor, a vehicle temperature sensor, and an audio sensor.

4. The system of claim 1, wherein the system comprises a plurality of sensors in the vehicle.

5. The system of claim 1, wherein the image sensor comprises an infrared image sensor, and a thermal image sensor; and wherein the image sensor is rotatable at an angle to get an image.

6. The system of claim 1, wherein the system comprises a plurality of image sensors.

7. The system of claim 1, wherein the sensor comprises at least one of a heart rate sensor, a temperature sensor, and a blood pressure sensor.

8. The system of claim 1, wherein the processor is configured to receive a third data from a wearable device through the connector; and wherein the wearable device comprises at least one of a heart rate sensor, a temperature sensor, and a blood pressure sensor.

9. The system of claim 8, wherein the transmission to the application occurs automatically in response to the receipt of the first data, the second data and the third data at the central server.

10. The system of claim 1, wherein the system is configured to be customized to a data format and a network protocol of an installation.

11. The system of claim 10, wherein the system comprises the data format and a communication protocol translator module to convert data files and the communication protocol to a common format and a common communication protocol.

12. The system of claim 1, wherein the protocol is one of a hospital transmission protocol, related patient monitoring protocol, and a standard Health Information Technology (HIT) protocol based on a Health Level 7 (HL7) protocol.

13. The system of claim 1, wherein the transmission to the application occurs in response to a request received at the central server by a vehicle infotainment system, and a mobile device requesting data gathered by the sensor; and wherein the mobile device belongs to at least one of a medical facility provider, an emergency contact, and a nearby vehicle owner.

14. A method comprising:
detecting a vehicle seat in a vehicle;
establishing a secure connection with the vehicle seat through a connector;
receiving a first data from a sensor and a second data from an image sensor through the connector, the first data and the second data being indicative of an information gathered regarding at least one parameter related to at least one of a condition of the vehicle seat, a health and wellness of an occupant of the vehicle, and the connector being configured to facilitate gathering of the information;
encoding the first data and the second data by identifying protected health information for transmission of a secure data message using a protocol; and
transmitting the first data and the second data in real time via a communication module to an application installed in a central server thereon, the application being configured to facilitate receipt of the first data and the second data from the central server,
wherein the secure data message generated using the protocol comprises: a vehicle information, a location of the vehicle, an information related to the occupant, a health parameter, a seating detail of the occupant, a pre-health condition detail of the occupant, an allergy detail of the occupant, an emergency contact detail, other occupants of the vehicle, and a type of medical emergency detected.

15. The method of claim 14, wherein the first data comprises at least one of a first position of the vehicle seat, a second position of the occupant on the vehicle seat, a weight of the occupant, a height of the occupant, and a pressure on a seat belt.

16. The method of claim 14, wherein the second data comprises a first image of a vehicle seat position, a second image of a second position of the occupant on the vehicle seat, and a third image of a size of the vehicle seat according to a height and a weight of the occupant.

17. The method of claim 14, wherein the method further comprises receiving a third data from a wearable device; and wherein the third data comprises at least one of the health and wellness data of the occupant comprising a heart rate, a blood pressure, a skin color, conscious state of the occupant and a temperature of the occupant.

18. The method of claim 14, wherein the condition of the vehicle seat and the health and wellness of the occupant is displayed on a display of a vehicle infotainment system, and a mobile device; and wherein the mobile device belongs to at least one of a medical facility provider, an emergency contact, and a nearby vehicle owner.

19. A non-transitory computer storage medium storing a sequence of instructions, which when executed by a processor, causes:
detecting a vehicle seat in a vehicle;
establishing a secure connection with the vehicle seat through a connector;
receiving a first data from a sensor and a second data from an image sensor through the connector, the first data and the second data being indicative of an information gathered regarding at least one parameter related to at least one of a condition of the vehicle seat, a health and wellness of an occupant of the vehicle, and the connector being configured to facilitate gathering of the information;
encoding the first data and the second data by identifying protected health information for transmission of a secure data message using a protocol; and
transmitting the first data and the second data in real time via a communication module to an application installed in a central server thereon, the application being configured to facilitate receipt of the first data and the second data from the central server,
wherein the secure data message generated using the protocol comprises: a vehicle information, a location of the vehicle, an information related to the occupant, a health parameter, a seating detail of the occupant, a pre-health condition detail of the occupant, an allergy detail of the occupant, an emergency contact detail, other occupants of the vehicle, and a type of medical emergency detected.

* * * * *